(12) United States Patent
Deschamps et al.

(10) Patent No.: US 10,329,574 B2
(45) Date of Patent: Jun. 25, 2019

(54) METHODS FOR THE IDENTIFICATION OF VARIANT RECOGNITION SITES FOR RARE-CUTTING ENGINEERED DOUBLE-STRAND-BREAK-INDUCING AGENTS AND COMPOSITIONS AND USES THEREOF

(71) Applicants: E. I. DU PONT DE NEMOURS AND COMPANY, Wilmington, DE (US); PIONEER HI-BRED INTERNATIONAL, INC., Johnston, IA (US)

(72) Inventors: Stephane Deschamps, Hockessin, DE (US); James English, San Ramon, CA (US); Zhongsen Li, Hockessin, DE (US); Victor Llaca, Newark, DE (US); Joshua K. Young, Johnston, IA (US)

(73) Assignees: E I DU PONT DE NEMOURS AND COMPANY, Wilmington, DE (US); PIONEER HI-BRED INTERNATIONAL, INC. IA (US)

( * ) Notice: Subject to any disclaimer, the term of this patent is extended or adjusted under 35 U.S.C. 154(b) by 495 days.

(21) Appl. No.: 14/775,777

(22) PCT Filed: Mar. 10, 2014

(86) PCT No.: PCT/US2014/022500
§ 371 (c)(1),
(2) Date: Sep. 14, 2015

(87) PCT Pub. No.: WO2014/164466
PCT Pub. Date: Oct. 9, 2014

(65) Prior Publication Data
US 2016/0032297 A1 Feb. 4, 2016

Related U.S. Application Data

(60) Provisional application No. 61/777,238, filed on Mar. 12, 2013.

(51) Int. Cl.
*C12N 15/82* (2006.01)
*C12N 9/22* (2006.01)
*C12Q 1/6811* (2018.01)

(52) U.S. Cl.
CPC ........... *C12N 15/8213* (2013.01); *C12N 9/22* (2013.01); *C12N 15/8241* (2013.01); *C12Q 1/6811* (2013.01)

(58) Field of Classification Search
CPC .............................. C12Q 1/6811; C12N 9/22; C12N 15/8213; C12N 15/8241
See application file for complete search history.

(56) References Cited

U.S. PATENT DOCUMENTS

| | | | |
|---|---|---|---|
| 2009/0133152 A1 | 5/2009 | Lyznik et al. | |
| 2011/0113509 A1* | 5/2011 | Jantz ....................... | C12N 9/22 800/278 |
| 2011/0165679 A1 | 7/2011 | Gordon-Kamm et al. | |

FOREIGN PATENT DOCUMENTS

| WO | 2003/078619 A1 | 9/2003 |
|---|---|---|
| WO | 2004/031346 A2 | 4/2004 |
| WO | 2005/105989 A1 | 11/2005 |
| WO | 2006/097784 A1 | 9/2006 |
| WO | 2006/097853 A1 | 9/2006 |
| WO | 2006/097854 A1 | 9/2006 |
| WO | 2009/006297 A2 | 1/2009 |
| WO | 2012/129373 A2 | 9/2012 |
| WO | 2013/006745 A2 | 1/2013 |

OTHER PUBLICATIONS

Patrick Chames et al., In vivo selection of engineered homing endonucleases using double-strand break induced homologous recombination, Nucleic Acids Research, 2005. vol. 33, No. 20 e178.
Zhilei Chen et al, A highly sensitive selection method for directed evolution of homing endonucleases, Nucleic Acids Research, 2005. vol. 33, No. 18, e154.
Brett S. Chevalier et al., Homing endonucleases: structural and functional insight into the catalysts of intron/intein mobility, Nucleic Acids Research, 2001, vol. 29, No. 18, pp. 3757-3774.
Brett S. Chevalier et al., Design, Activity, and Structure of a Highly Specific Artificial Endonuclease, Molecular Cell, Oct. 2002, pp. 895-905, vol. 10.
Franz Dürrenberger et al., Characterization of the cleavage site and the recognition sequence of the I-CreI DNA endonuclease encoded by the chloroplast ribosomal intron of *Chlamydomonas reinhardtii*, Mol. Gen. Genet, 1993, pp. 409-414, vol. 236.
Jean-Charles Epinat et al., A novel engineered meganuclease induces homologus recombination in yeast and mammalian cells, Nucleic Acids Research, 2003, pp. 2952-2962, vol. 31, No. 11.
Giedrius Gasiunas et al., Cas9-crRNA ribonucleoprotein complex mediates specific DNA cleavage for adaptive immunity in bacteria, PNAS, Sep. 4, 2012, E2579-E2586.
Frederick S. Gimble et al., Assessing the Plasticity of DNA Target Site Recognition of the PI-ScelI Homing Endonuclease Using a Bacterial Two-hybrid Selection System, J. Mol. Biol., 2003, pp. 993-1008, vol. 334.
Sylvestre Grizot et al., Context dependence between subdomains in the DNA binding interface of the I-CreI homing endonuclease, Nucleic Acids Research, Apr. 10, 2011, pp. 6124-6136, vol. 39, No. 14.
Mathias Gruen et al, An in vivo selection system for homing endonuclease activity, Nucleic Acids Research, 2002, vol. 30, No. 7, e29.

(Continued)

*Primary Examiner* — Antonio Galisteo Gonzalez

(57) ABSTRACT

Methods for the identification of variant recognition sites for rare cutting engineered double strand break inducing agents and compositions thereof are provided. Further provided are nucleic acid constructs, yeast, plants, plant cells, explants, seeds and grain having the of variant recognition sites. Various methods of identifying variant recognition sites with increased substrate activity for a rare cutting engineered double strand break inducing agents are provided.

6 Claims, 17 Drawing Sheets

Figure 2:
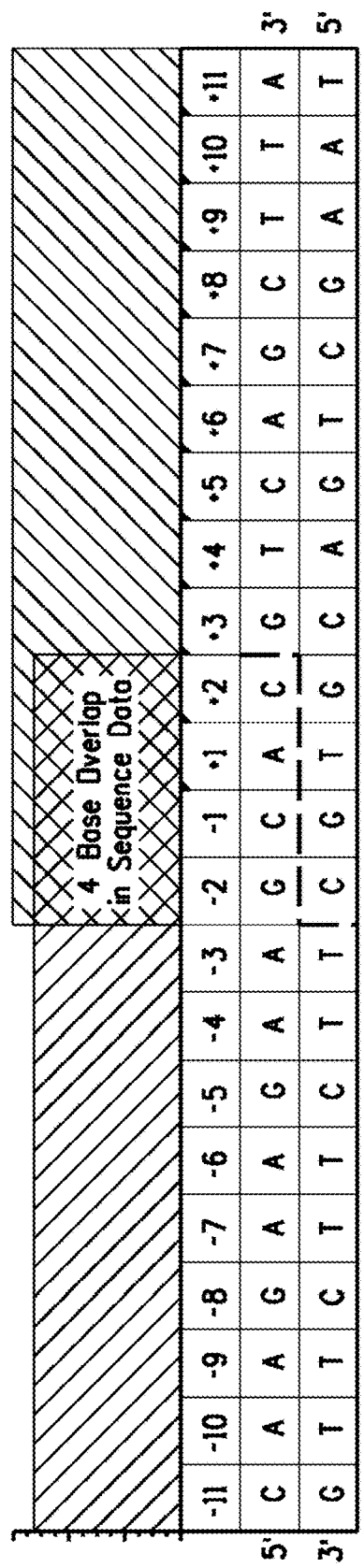

Specification includes a Sequence Listing.

(56) References Cited

OTHER PUBLICATIONS

Martin Jinek et al., A Programmable Dual-RNA-Guided DNA Endonuclease in Adaptive Bacterial Immunity, Science, Aug. 17, 2012, pp. 816-821, vol. 337.
Melissa S. Jurica et al., DNA Recognition and Cleavage by the LAGLIDADGE Homing Endonuclease I-CreI, Molecular Cell, Oct. 1998, pp. 469-476, vol. 2.
M. S. Jurica et al., Homing endonucleases: structure, function and evolution, Cell Mol. Life Sci, 1999, pp. 1304-1326, vol. 55.
Ben Langmead et al., Ultrafast and memory-efficient alignment of short DNA sequences to the human genome, Genome Biol, 2009, 10:R25.
Ting Li et al., TAL nucleases (TALNs): hybrid proteins composed of TAL effectors and FokI DNA-cleavage domain, Nucleic Acids Research, 2011, pp. 359-372, vol. 39, No. 1.
Patrick Lucas et al., Rapid evolution of the DNA-binding site in LAGLIDADG homing endonucleases, Nucleic Acids Research, 2001, pp. 960-969, vol. 29, No. 4.
Rafael Molina et al., Non-specific protein-DNA interactions control I-CreI target binding and cleavage, Nucleic Acids Research, 2012, pp. 6936-6945, vol. 40, No. 14.
Carmen M. Moure et al., Crystal structure of the intein homing endonuclease PI-SceI bound to its recognition sequence, Nature Structural Biology, Oct. 2002, p. 764, vol. 9, No. 10.
Laura E. Rosen et al., Homing endonuclease I-CreI derivatives with novel DNA target specificities, Nucleic Acids Research, 2006, pp. 4791-4800, vol. 34, No. 17.
Lenny M. Seligman et al., Mutations altering the cleavage specificity of a homing endonuclease, Nucleic Acids Research, 2002, pp. 3870-3879, vol. 30, No. 7.
Jeff Smith et al., Requirements for double-strand cleavage by chimeric restriction enzymes with zinc finger DNA-recognition domains, Nucleic Acids Research, 2000, pp. 3361-3369, vol. 28, No. 17.
Julianne Smith et al., A combinatorial approach to create artificial homing endonucleases cleaving chosen sequences, Nucleic Acids Research, 2006, vol. 34, No. 22, e149.
Barry L. Stoddard, Homing endonuclease structure and function, Quarterly Reviews of Biophysics, 2006, pp. 49-95, vol. 38.
Django Sussman et al., Isolation and Characterization of New Homing Endonuclease Specificities at Individual Target Site Positions, J. Mol. Biol, 2004, pp. 31-41, vol. 342.
Andrew J. Thompson et al., Cleavage and recognition pattern of a double-strand-specific endonuclease (I-CreI) encoded by the chloroplast 23S rRNA intron of Chlamydomonas reinhardtii.
Umut Y. Ulge et al., Comprehensive computational design of mCreI homing endonuclease cleavage specificity for genome engineering, Nucleic Acids Research, 2011, pp. 4330-4339, vol. 39, No. 10.
N. Guhan et al., Structural and Functional Characteristics of Homing Endonucleases, Critical Reviews in Biochemistry and Molecular Biology, 2003, pp. 199-248, vol. 38, No. 3.
International Search Report and Written Opinion—PCT/US2014/022500—dated Jul. 16, 2014.

\* cited by examiner

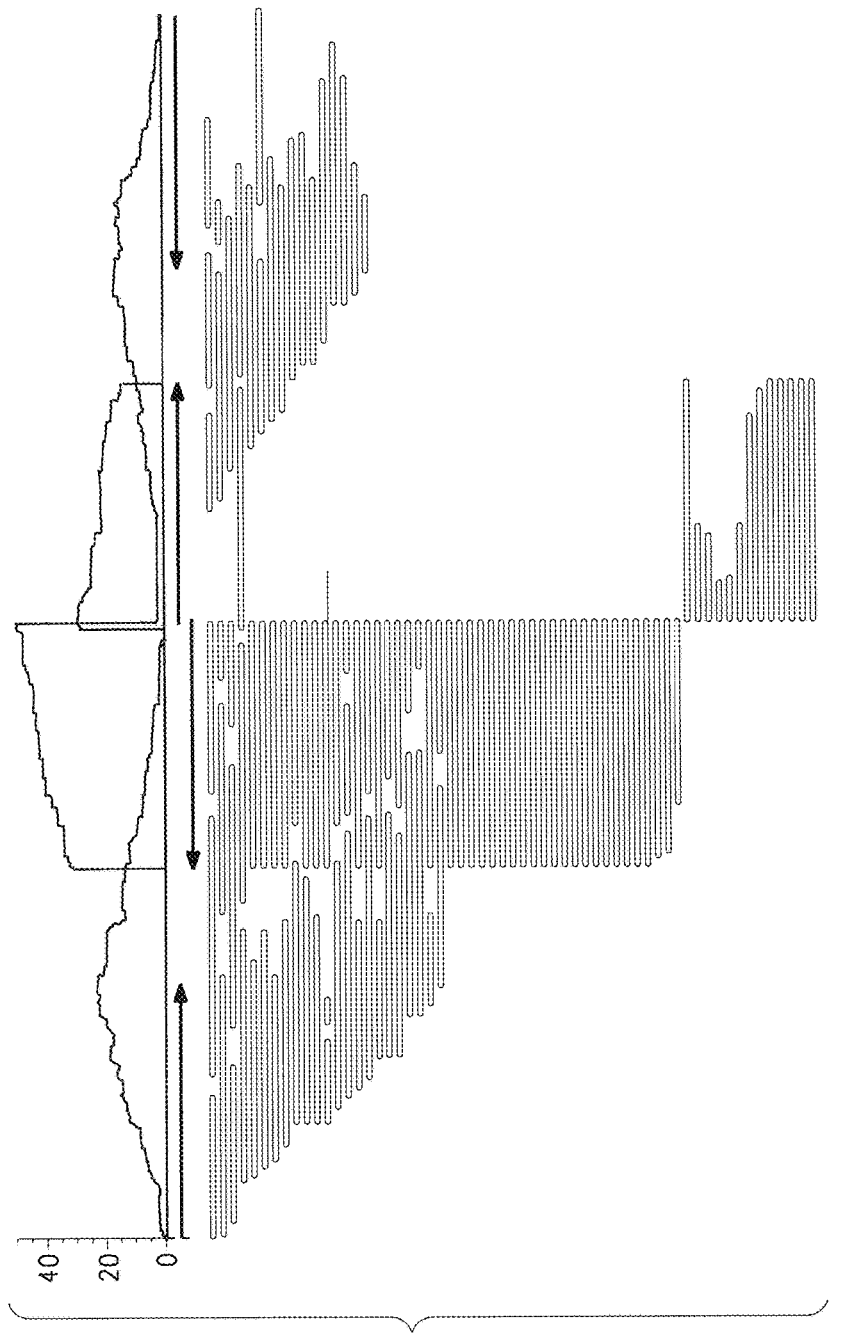
FIG. 1A
FIG. 1B

FIG. 3A

22bp Recognition Site

| % DNA Base Composition | -11 | -10 | -9 | -8 | -7 | -6 | -5 | -4 | -3 | -2 | -1 | +1 | +2 | +3 | +4 | +5 | +6 | +7 | +8 | +9 | +10 | +11 |
|---|---|---|---|---|---|---|---|---|---|---|---|---|---|---|---|---|---|---|---|---|---|---|
| %G | 10% | 3% | 17% | 23% | 7% | 7% | 0% | 0% | 0% | 50% | 23% | 0% | 0% | 87% | 3% | 37% | 7% | 90% | 3% | 97% | 3% | 27% |
| %C | 50% | 7% | 30% | 27% | 67% | 40% | 93% | 0% | 100% | 0% | 3% | 43% | 67% | 10% | 20% | 10% | 63% | 3% | 13% | 0% | 10% | 0% |
| %T | 17% | 63% | 17% | 23% | 7% | 47% | 7% | 87% | 0% | 37% | 10% | 57% | 23% | 0% | 70% | 0% | 20% | 0% | 80% | 3% | 87% | 7% |
| %A | 23% | 27% | 37% | 27% | 20% | 7% | 0% | 13% | 0% | 13% | 63% | 0% | 10% | 3% | 7% | 53% | 10% | 7% | 3% | 0% | 0% | 67% |
| Intended Recognition Site | A | T | A | T | A | C | C | T | C | A | C | A | C | G | T | A | C | G | C | G | T | A |

FIG. 3B

22bp Recognition Site

| % DNA Base Composition | -11 | -10 | -9 | -8 | -7 | -6 | -5 | -4 | -3 | -2 | -1 | +1 | +2 | +3 | +4 | +5 | +6 | +7 | +8 | +9 | +10 | +11 |
|---|---|---|---|---|---|---|---|---|---|---|---|---|---|---|---|---|---|---|---|---|---|---|
| %G | 5% | 11% | 9% | 39% | 2% | 15% | 79% | 2% | 7% | 75% | 4% | 30% | 5% | 96% | 2% | 2% | 12% | 39% | 51% | 15% | 4% | 36% |
| %C | 59% | 2% | 1% | 9% | 51% | 2% | 6% | 1% | 9% | 3% | 26% | 3% | 3% | 0% | 4% | 90% | 4% | 5% | 8% | 7% | 12% | 16% |
| %A | 4% | 86% | 89% | 36% | 43% | 77% | 1% | 71% | 46% | 7% | 67% | 48% | 3% | 3% | 37% | 8% | 82% | 7% | 29% | 10% | 9% | 36% |
| %T | 32% | 1% | 2% | 17% | 4% | 6% | 14% | 26% | 38% | 15% | 3% | 17% | 39% | 1% | 57% | 0% | 2% | 49% | 12% | 68% | 75% | 12% |
| Intended Recognition Site | C | A | A | A | C | A | A | A | T | T | C | A | C | G | T | C | A | G | A | T | T | T |

| Lig3-4 Meganuclease Intended Recognition Site | -11 | -10 | -9 | -8 | -7 | -6 | -5 | -4 | -3 | -2 | -1 | +1 | +2 | +3 | +4 | +5 | +6 | +7 | +8 | +9 | +10 | +11 |
|---|---|---|---|---|---|---|---|---|---|---|---|---|---|---|---|---|---|---|---|---|---|---|
| -11C | A | T | A | T | A | C | C | T | C | A | C | A | C | G | T | A | C | G | C | G | T | A |
| -7C | C | T | A | T | A | C | C | T | C | A | C | A | C | G | T | A | C | G | C | G | T | A |
| -2G | A | T | A | T | C | C | C | T | C | A | C | A | C | G | T | A | C | G | C | G | T | A |
| -1T | A | T | A | T | A | C | C | T | C | G | C | A | C | G | T | A | C | G | C | G | T | A |
| -8T | A | T | A | T | A | C | C | T | C | A | T | A | C | G | T | A | C | G | T | G | T | A |
| -7C, -8T | A | T | A | T | C | C | C | T | C | A | C | A | C | G | T | A | C | G | T | G | T | A |
| -11C, -7C, -2G, -1T, +8T | C | T | A | T | C | C | C | T | C | G | T | A | C | G | T | A | C | G | T | G | T | A |
| -11C, -7C, -1T, +8T | C | T | A | T | C | C | C | T | C | A | T | A | C | G | T | A | C | G | T | G | T | A |

FIG. 4A

FIG. 4B

| MHP14- Meganuclease Intended Recognition Site | -11 | -10 | -9 | -8 | -7 | -6 | -5 | -4 | -3 | -2 | -1 | +1 | +2 | +3 | +4 | +5 | +6 | +7 | +8 | +9 | +10 | +11 |
|---|---|---|---|---|---|---|---|---|---|---|---|---|---|---|---|---|---|---|---|---|---|---|
| -3A | C | A | A | A | C | A | G | A | [A] | T | C | A | C | G | T | C | A | G | A | T | T | T |
| -2G | C | A | A | A | C | A | G | A | T | [G] | C | A | C | G | T | C | A | G | A | T | T | T |
| -1T | C | A | A | A | C | A | G | A | T | T | [T] | A | C | G | T | C | A | G | A | T | T | T |
| +2A | C | A | A | A | C | A | G | A | T | T | C | A | [A] | G | T | C | A | G | A | T | T | T |
| -7T | C | A | A | A | [T] | A | G | A | T | T | C | A | C | G | T | C | A | G | A | T | T | T |
| +8G | C | A | A | A | C | A | G | A | T | T | C | A | C | G | T | C | A | G | [G] | T | T | T |
| +11G | C | A | A | A | C | A | G | A | T | T | C | A | C | G | T | C | A | G | A | T | T | [G] |
| +11A | C | A | A | A | C | A | G | A | T | T | C | A | C | G | T | C | A | G | A | T | T | [A] |
| -3A,-2G,-1T,+2A,+7T,+8G,+11G | C | A | A | A | C | A | G | A | [A] | [G] | [T] | A | [A] | G | T | C | A | [T] | [G] | T | T | [G] |
| -3A,-2G,-1T,+2A,+7T,+8G,+11A | C | A | A | A | C | A | G | A | [A] | [G] | [T] | A | [A] | G | T | C | A | [T] | [G] | T | T | [A] |
| -3A,-2G,-1T,+7T,+8G,+11G | C | A | A | A | C | A | G | A | [A] | [G] | [T] | A | C | G | T | C | A | [T] | [G] | T | T | [G] |
| -2G,-1T,+2A,+7T,+8G,+11G | C | A | A | A | C | A | G | A | T | [G] | [T] | A | [A] | G | T | C | A | [T] | [G] | T | T | [G] |
| -2G,-1T,+7T,+8G,+11G | C | A | A | A | C | A | G | A | T | [G] | [T] | A | C | G | T | C | A | [T] | [G] | T | T | [G] |

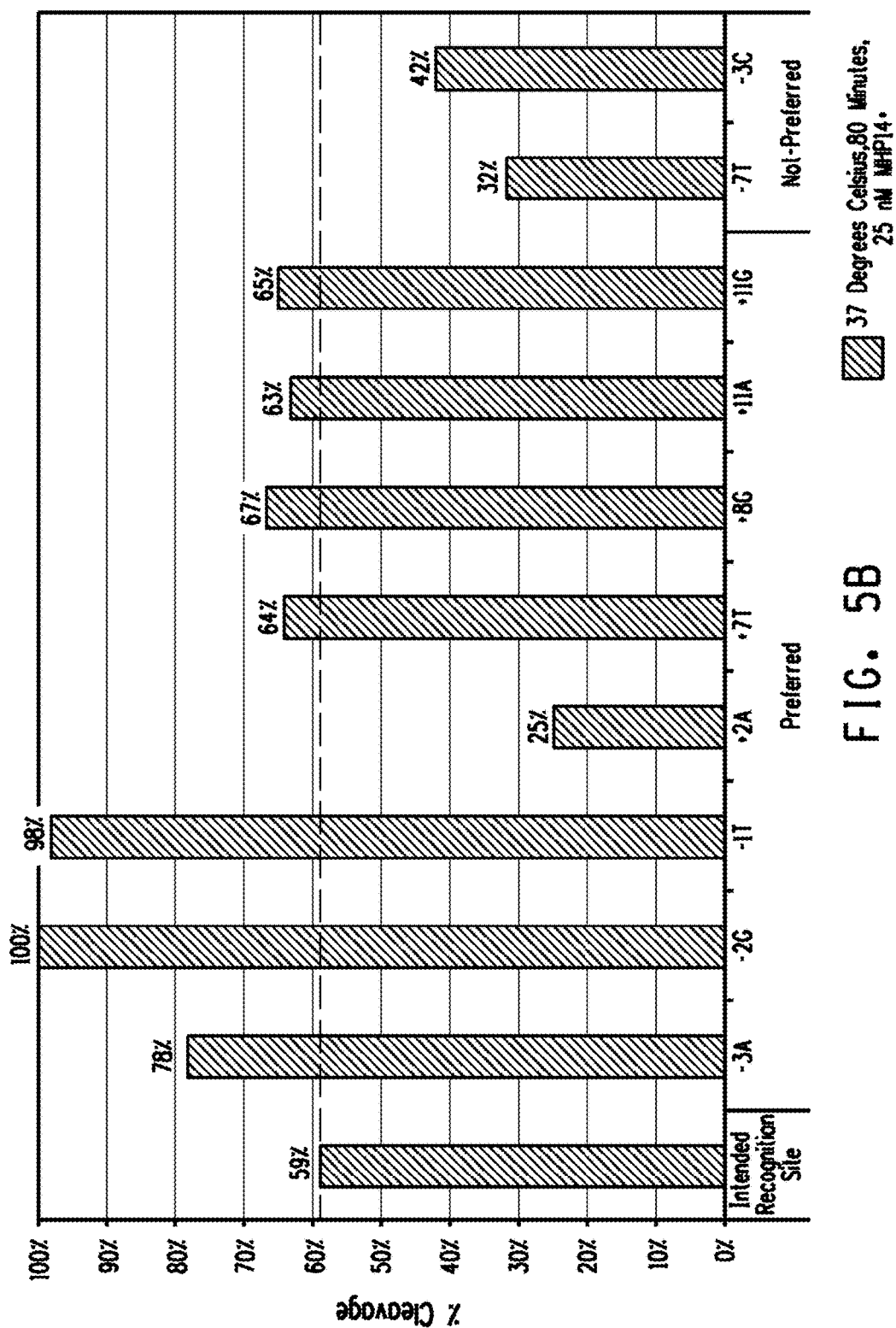

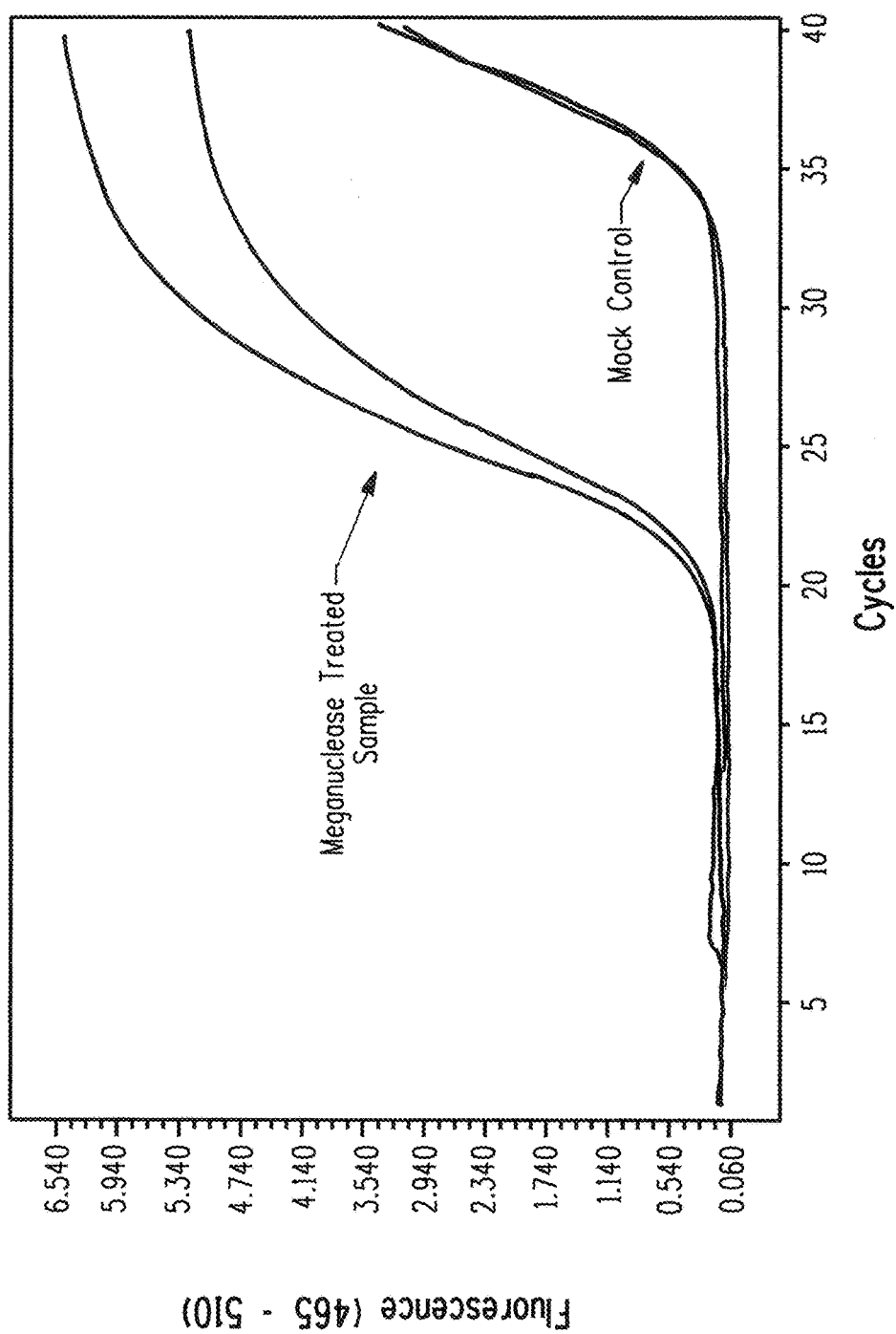

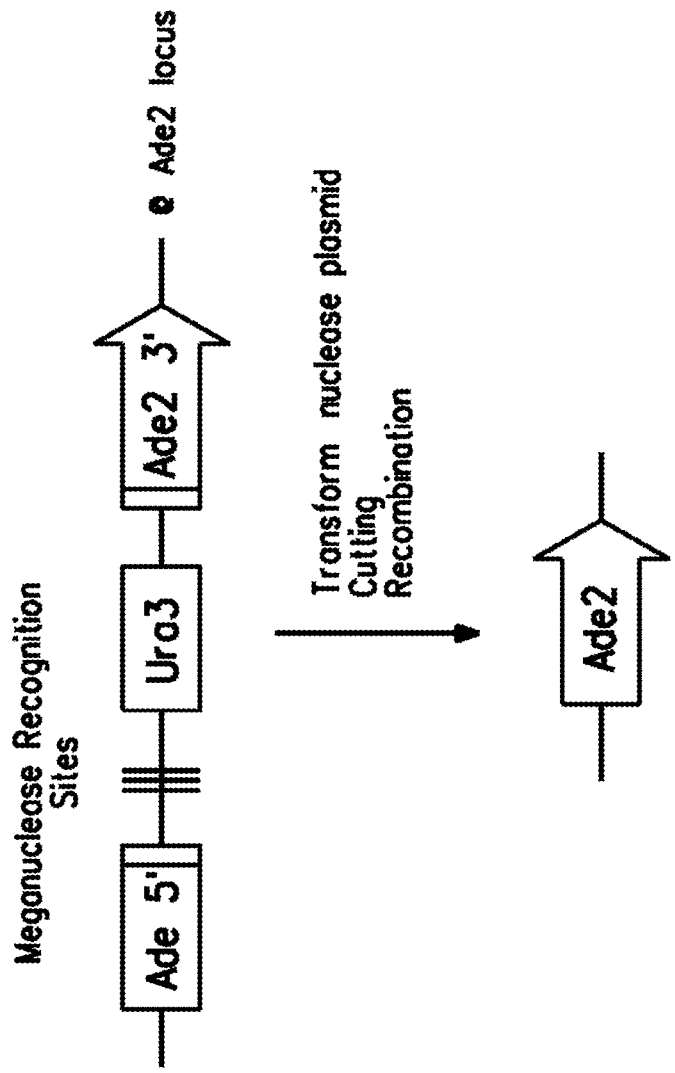
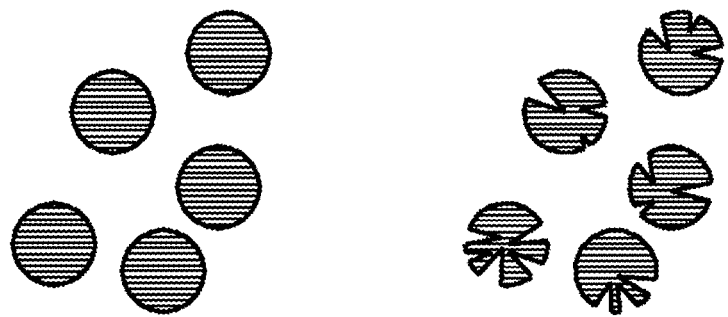
FIG. 8

SEQUENCE LISTING

```
<160> NUMBER OF SEQ ID NOS: 39

<210> SEQ ID NO 1
<211> LENGTH: 1053
<212> TYPE: DNA
<213> ORGANISM: artificial sequence
<220> FEATURE:
<223> OTHER INFORMATION: LIG3-4 meganuclease

<400> SEQUENCE: 1
atgaacacca agtacaacaa ggagttcctg ctctacctgg ccggcttcgt ggacggcgac      60
ggctccatca aggcgcagat caagccgaac cagtcctgca agttcaagca ccagctctcc     120
ctgaccttcc aggtgaccca gaagacgcag aggcgctggt tcctcgacaa gctggtcgac     180
gagatcgggg tgggctacgt ctacgaccgc gggtcggtgt ccgactacga gctctcccag     240
atcaagcccc tgcacaactt cctcacccag ctccagccgt tcctcaagct gaagcagaag     300
caggcgaacc tcgtcctgaa gatcatcgag cagctcccct cggccaagga gtccccggac     360
aagttcctgg aggtgtgcac gtgggtcgac cagatcgcgg ccctcaacga cagcaagacc     420
cgcaagacga cctcggagac ggtgcgggcg gtcctggact ccctcccagg atccgtggga     480
ggtctatcgc catctcaggc atccagcgcc gcatcctcgg cttcctcaag cccggggttca    540 gggatctccg aagcactcag agctggagca actaagtcca aggaattcct gctctacctg     600
```

```
gccggcttcg tggacggcga cggctccatc atcgcgtcca tcaagccgcg ccagtgctac    660
aagttcaagc acgagctccg cctggagttc accgtgaccc agaagacgca gaggcgctgg    720
ttcctcgaca agctggtcga cgagatcggg gtgggctacg tctacgaccg cgggtcggtg    780
tccgactacc gcctctccca gatcaagccc ctgcacaact tcctcaccca gctccagccg    840
ttcctcaagc tgaagcagaa gcaggcgaac ctcgtcctga gatcatcga gcagctcccc    900 tcggccaagg agtccccgga caagttcctg gaggtgtgca cgtgggtcga ccagatcgcg    960
gccctcaacg acagcaagac ccgcaagacg acctcggaga cggtgcgggc ggtcctggac   1020
tccctcagcg agaagaagaa gtcgtccccc tga                                1053
```

<210> SEQ ID NO 2
<211> LENGTH: 350
<212> TYPE: PRT
<213> ORGANISM: artificial sequence
<220> FEATURE:
<223> OTHER INFORMATION: LIG3-4 meganuclease

<400> SEQUENCE: 2

```
Met Asn Thr Lys Tyr Asn Lys Glu Phe Leu Leu Tyr Leu Ala Gly Phe
1               5                   10                  15

Val Asp Gly Asp Gly Ser Ile Lys Ala Gln Ile Lys Pro Asn Gln Ser
            20                  25                  30

Cys Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Asp Tyr Glu Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Thr Lys
            180                 185                 190

Ser Lys Glu Phe Leu Leu Tyr Leu Ala Gly Phe Val Asp Gly Asp Gly
        195                 200                 205

Ser Ile Ile Ala Ser Ile Lys Pro Arg Gln Cys Tyr Lys Phe Lys His
    210                 215                 220

Glu Leu Arg Leu Glu Phe Thr Val Thr Gln Lys Thr Gln Arg Arg Trp
225                 230                 235                 240

Phe Leu Asp Lys Leu Val Asp Glu Ile Gly Val Gly Tyr Val Tyr Asp
                245                 250                 255

Arg Gly Ser Val Ser Asp Tyr Arg Leu Ser Gln Ile Lys Pro Leu His
            260                 265                 270

Asn Phe Leu Thr Gln Leu Gln Pro Phe Leu Lys Leu Lys Gln Lys Gln
```

```
            275                 280                 285
Ala Asn Leu Val Leu Lys Ile Ile Glu Gln Leu Pro Ser Ala Lys Glu
        290                 295                 300

Ser Pro Asp Lys Phe Leu Glu Val Cys Thr Trp Val Asp Gln Ile Ala
305                 310                 315                 320

Ala Leu Asn Asp Ser Lys Thr Arg Lys Thr Thr Ser Glu Thr Val Arg
                325                 330                 335

Ala Val Leu Asp Ser Leu Ser Glu Lys Lys Lys Ser Ser Pro
            340                 345                 350

<210> SEQ ID NO 3
<211> LENGTH: 1053
<212> TYPE: DNA
<213> ORGANISM: artificial sequence
<220> FEATURE:
<223> OTHER INFORMATION: MHP14+ meganuclease

<400> SEQUENCE: 3
atgaacacca agtacaacaa ggagttcctg ctctacctgg ccggcttcgt ggacggcgac      60
ggctccatca tcgcgcagat caagccgaac cagtcctaca gttcaagca ccagctcatg     120 ctgaccttca ccgtgaccca gaagacgcag aggcgctggt cctcgacaa gctggtcgac     180 gagatcgggg tgggcaaggt ccgcgaccgc gggtcggtgt ccgactacat cctctcccag     240
atcaagcccc tgcacaactt cctcacccag ctccagccgt tcctcaagct gaagcagaag     300
caggcgaacc tcgtcctgaa gatcatcgag cagctcccct cggccaagga gtccccggac     360
aagttcctgg aggtgtgcac cgtgggtcga ccagatcgcgg ccctcaacga cagcaagacc     420
cgcaagacga cctcggagac ggtgcgggcg gtcctggact ccctcccagg atccgtggga     480
ggtctatcgc catctcaggc atccagcgcc gcatcctcgg cttcctcaag cccgggttca     540
gggatctccg aagcactcag agctggagca actaagtcca aggaattcct gctctacctg     600
gccggcttcg tggacggcga cggctccatc atcgcggcga tcaagccgaa ccagtcctac     660
aagttcaagc accagctctc cctgaccttc accgtgaccc agaagacgca gaggcgctgg     720
ttcctcgaca gctggtcga cgagatcggg gtgggctacg tccgcgacca ggggtcggtg     780
tcccactacc agctctccca gatcaagccc ctgcacaact tcctcaccca gctccagccg     840
ttcctcaagc tgaagcagaa gcaggcgaac ctcgtcctga gatcatcga gcagctcccc     900 tcggccaagg agtccccgga caagttcctg gaggtgtgca cgtgggtcga ccagatcgcg     960
gccctcaacg acagcaagac ccgcaagacg acctcggaga cggtgcgggc ggttctagac    1020
tccctcagcg agaagaagaa gtcgtccccc tga                                 1053

<210> SEQ ID NO 4
<211> LENGTH: 350
<212> TYPE: PRT
<213> ORGANISM: artificial sequence
<220> FEATURE:
<223> OTHER INFORMATION: MHP14+ meganuclease

<400> SEQUENCE: 4

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Met Leu Thr Phe Thr Val Thr Gln Lys
        35                  40                  45
```

-continued

```
Thr Gln Arg Arg Trp Phe Leu Asp Lys Leu Val Asp Glu Ile Gly Val
 50                  55                  60

Gly Lys Val Arg Asp Arg Gly Ser Val Ser Asp Tyr Ile Leu Ser Gln
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ala Ser Ser
                165                 170                 175

Ser Pro Gly Ser Gly Ile Ser Glu Ala Leu Arg Ala Gly Ala Thr Lys
        180                 185                 190

Ser Lys Glu Phe Leu Leu Tyr Leu Ala Gly Phe Val Asp Gly Asp Gly
    195                 200                 205

Ser Ile Ile Ala Ala Ile Lys Pro Asn Gln Ser Tyr Lys Phe Lys His
210                 215                 220

Gln Leu Ser Leu Thr Phe Thr Val Thr Gln Lys Thr Gln Arg Arg Trp
225                 230                 235                 240

Phe Leu Asp Lys Leu Val Asp Glu Ile Gly Val Gly Tyr Val Arg Asp
                245                 250                 255

Gln Gly Ser Val Ser His Tyr Gln Leu Ser Gln Ile Lys Pro Leu His
            260                 265                 270

Asn Phe Leu Thr Gln Leu Gln Pro Phe Leu Lys Leu Lys Gln Lys Gln
        275                 280                 285

Ala Asn Leu Val Leu Lys Ile Ile Glu Gln Leu Pro Ser Ala Lys Glu
    290                 295                 300

Ser Pro Asp Lys Phe Leu Glu Val Cys Thr Trp Val Asp Gln Ile Ala
305                 310                 315                 320

Ala Leu Asn Asp Ser Lys Thr Arg Lys Thr Thr Ser Glu Thr Val Arg
                325                 330                 335

Ala Val Leu Asp Ser Leu Ser Glu Lys Lys Ser Ser Pro
            340                 345                 350

<210> SEQ ID NO 5
<211> LENGTH: 41
<212> TYPE: DNA
<213> ORGANISM: Artificial sequence
<220> FEATURE:
<223> OTHER INFORMATION: dephosphorylated adapter
<220> FEATURE:
<221> NAME/KEY: misc_feature
<222> LOCATION: (38)..(41)
<223> OTHER INFORMATION: n is a, c, g, or t

<400> SEQUENCE: 5
ggttgacatg ctggattgag acttccctgc aggacgtnnn n                        41

<210> SEQ ID NO 6
<211> LENGTH: 24
<212> TYPE: DNA
<213> ORGANISM: Artificial sequence
<220> FEATURE:
```

<223> OTHER INFORMATION: primer A

<400> SEQUENCE: 6
gttgacatgc tggattgaga cttc                                    24

<210> SEQ ID NO 7
<211> LENGTH: 21
<212> TYPE: DNA
<213> ORGANISM: Artificial sequence
<220> FEATURE:
<223> OTHER INFORMATION: primer B

<400> SEQUENCE: 7
caagcagaag acggcatacg a                                       21

<210> SEQ ID NO 8
<211> LENGTH: 61
<212> TYPE: DNA
<213> ORGANISM: Artificial sequence
<220> FEATURE:
<223> OTHER INFORMATION: Illumina-compatibe adapter

<400> SEQUENCE: 8
aatgatacgg cgaccaccga gatctacact ctttccctac acgacgctct tccgatctgc    60
a                                                             61

<210> SEQ ID NO 9
<211> LENGTH: 9
<212> TYPE: DNA
<213> ORGANISM: Artificial sequence
<220> FEATURE:
<223> OTHER INFORMATION: sequence tag

<400> SEQUENCE: 9 gcaggacgt                                                      9

<210> SEQ ID NO 10
<211> LENGTH: 9
<212> TYPE: DNA
<213> ORGANISM: Artificial sequence
<220> FEATURE:
<223> OTHER INFORMATION: complement of sequence tag

<400> SEQUENCE: 10 acgtcctgc                                                      9

<210> SEQ ID NO 11
<211> LENGTH: 22
<212> TYPE: DNA
<213> ORGANISM: Artificial sequence
<220> FEATURE:
<223> OTHER INFORMATION: Figure 2 5'-3' SEQUENCE

<400> SEQUENCE: 11
caagaagaag cacgtcagct ta                                      22

<210> SEQ ID NO 12
<211> LENGTH: 22
<212> TYPE: DNA
<213> ORGANISM: Artificial sequence
<220> FEATURE:
<223> OTHER INFORMATION: Figure 2 3'-5' SEQUENCE

<400> SEQUENCE: 12
gttcttcttc gtgcagtcga at                                      22

<210> SEQ ID NO 13
<211> LENGTH: 22
<212> TYPE: DNA
<213> ORGANISM: Artificial sequence
<220> FEATURE:
<223> OTHER INFORMATION: LIG3-4 Intended Recognition Sequence

<400> SEQUENCE: 13
atatacctca cacgtacgcg ta                                            22

<210> SEQ ID NO 14
<211> LENGTH: 22
<212> TYPE: DNA
<213> ORGANISM: Artificial sequence
<220> FEATURE:
<223> OTHER INFORMATION: MHP14+ Intended Recognition Sequence

<400> SEQUENCE: 14
caaacagatt cacgtcagat tt                                            22

<210> SEQ ID NO 15
<211> LENGTH: 22
<212> TYPE: DNA
<213> ORGANISM: Artificial sequence
<220> FEATURE:
<223> OTHER INFORMATION: LIG3-4 variant recognition sequence, -11 C

<400> SEQUENCE: 15
ctatacctca cacgtacgcg ta                                            22

<210> SEQ ID NO 16
<211> LENGTH: 22
<212> TYPE: DNA
<213> ORGANISM: Artificial sequence
<220> FEATURE:
<223> OTHER INFORMATION: LIG3-4 variant recognition sequence, -7C

<400> SEQUENCE: 16
atatccctca cacgtacgcg ta                                            22

<210> SEQ ID NO 17
<211> LENGTH: 22
<212> TYPE: DNA
<213> ORGANISM: Artificial sequence
<220> FEATURE:
<223> OTHER INFORMATION: LIG3-4 variant recognition sequence, -2G

<400> SEQUENCE: 17
atatacctcg cacgtacgcg ta                                            22

<210> SEQ ID NO 18
<211> LENGTH: 22
<212> TYPE: DNA
<213> ORGANISM: Artificial sequence
<220> FEATURE:
<223> OTHER INFORMATION: LIG3-4 variant recognition sequence, -1T

<400> SEQUENCE: 18
atatacctca tacgtacgcg ta                                            22

<210> SEQ ID NO 19
<211> LENGTH: 22
<212> TYPE: DNA
<213> ORGANISM: Artificial sequence
<220> FEATURE:

<223> OTHER INFORMATION: LIG3-4 variant recognition sequence, +8T

<400> SEQUENCE: 19
atatacctca cacgtacgtg ta                                               22

<210> SEQ ID NO 20
<211> LENGTH: 22
<212> TYPE: DNA
<213> ORGANISM: Artificial sequence
<220> FEATURE:
<223> OTHER INFORMATION: LIG3-4 variant recognition sequence,-7C, +8T

<400> SEQUENCE: 20
atatccctca cacgtacgtg ta                                               22

<210> SEQ ID NO 21
<211> LENGTH: 22
<212> TYPE: DNA
<213> ORGANISM: Artificial sequence
<220> FEATURE:
<223> OTHER INFORMATION: LIG3-4 variant recognition sequence, -11C, -7C,
      -2G, -1T, +8T

<400> SEQUENCE: 21
ctatccctcg tacgtacgtg ta                                               22

<210> SEQ ID NO 22
<211> LENGTH: 22
<212> TYPE: DNA
<213> ORGANISM: Artificial sequence
<220> FEATURE:
<223> OTHER INFORMATION: LIG3-4 variant recognition sequence, -11C, -7C,
      -1T, +8T

<400> SEQUENCE: 22
ctatccctca tacgtacgtg ta                                               22

<210> SEQ ID NO 23
<211> LENGTH: 22
<212> TYPE: DNA
<213> ORGANISM: Artificial sequence
<220> FEATURE:
<223> OTHER INFORMATION: MHP14+ variant recognition sequence, -3A

<400> SEQUENCE: 23
caaacagaat cacgtcagat tt                                               22

<210> SEQ ID NO 24
<211> LENGTH: 22
<212> TYPE: DNA
<213> ORGANISM: Artificial sequence
<220> FEATURE:
<223> OTHER INFORMATION: MHP14+ variant recognition sequence, -2G

<400> SEQUENCE: 24
caaacagatg cacgtcagat tt                                               22

<210> SEQ ID NO 25
<211> LENGTH: 22
<212> TYPE: DNA
<213> ORGANISM: Artificial sequence
<220> FEATURE:
<223> OTHER INFORMATION: MHP14+ variant recognition sequence, -1T

<400> SEQUENCE: 25
caaacagatt tacgtcagat tt                                               22

<210> SEQ ID NO 26
<211> LENGTH: 22
<212> TYPE: DNA
<213> ORGANISM: Artificial sequence
<220> FEATURE:
<223> OTHER INFORMATION: MHP14+ variant recognition sequence, +2A

<400> SEQUENCE: 26
caaacagatt caagtcagat tt        22

<210> SEQ ID NO 27
<211> LENGTH: 22
<212> TYPE: DNA
<213> ORGANISM: Artificial sequence
<220> FEATURE:
<223> OTHER INFORMATION: MHP14+ variant recognition sequence, +7T

<400> SEQUENCE: 27
caaacagatt cacgtcatat tt        22

<210> SEQ ID NO 28
<211> LENGTH: 22
<212> TYPE: DNA
<213> ORGANISM: Artificial sequence
<220> FEATURE:
<223> OTHER INFORMATION: MHP14+ variant recognition sequence, +8G

<400> SEQUENCE: 28
caaacagatt cacgtcaggt tt        22

<210> SEQ ID NO 29
<211> LENGTH: 22
<212> TYPE: DNA
<213> ORGANISM: Artificial sequence
<220> FEATURE:
<223> OTHER INFORMATION: MHP14+ variant recognition sequence, +11G

<400> SEQUENCE: 29
caaacagatt cacgtcagat tg        22

<210> SEQ ID NO 30
<211> LENGTH: 22
<212> TYPE: DNA
<213> ORGANISM: Artificial sequence
<220> FEATURE:
<223> OTHER INFORMATION: MHP14+ variant recognition sequence, +11A

<400> SEQUENCE: 30
caaacagatt cacgtcagat ta        22

<210> SEQ ID NO 31
<211> LENGTH: 22
<212> TYPE: DNA
<213> ORGANISM: Artificial sequence
<220> FEATURE:
<223> OTHER INFORMATION: MHP14+ variant recognition sequence, -3A, -2G,
      -1T, +2A, +7T, +8G, +11G

<400> SEQUENCE: 31
caaacagaag taagtcatgt tg        22

<210> SEQ ID NO 32
<211> LENGTH: 22
<212> TYPE: DNA
<213> ORGANISM: Artificial sequence

```
<220> FEATURE:
<223> OTHER INFORMATION: MHP14+ variant recognition sequence, -3A, -2G,
      -1T, +2A, +7T, +8G, +11A

<400> SEQUENCE: 32
caaacagaag taagtcatgt ta                                              22

<210> SEQ ID NO 33
<211> LENGTH: 22
<212> TYPE: DNA
<213> ORGANISM: Artificial sequence
<220> FEATURE:
<223> OTHER INFORMATION: MHP14+ variant recognition sequence, 3A, -2G,
      -1T, +7T, +8G, +11G

<400> SEQUENCE: 33
caaacagaag tacgtcatgt tg                                              22

<210> SEQ ID NO 34
<211> LENGTH: 22
<212> TYPE: DNA
<213> ORGANISM: Artificial sequence
<220> FEATURE:
<223> OTHER INFORMATION: MHP14+ variant recognition sequence, -2G, -1T,
      +2A, +7T, +8G, +11G

<400> SEQUENCE: 34
caaacagatg taagtcatgt tg                                              22

<210> SEQ ID NO 35
<211> LENGTH: 22
<212> TYPE: DNA
<213> ORGANISM: Artificial sequence
<220> FEATURE:
<223> OTHER INFORMATION: MHP14+ variant recognition sequence,-2G, -1T,
      +7T, +8G, +11G

<400> SEQUENCE: 35
caaacagatg tacgtcatgt tg                                              22

<210> SEQ ID NO 36
<211> LENGTH: 3716
<212> TYPE: DNA
<213> ORGANISM: Saccharomyces cerevisiae

<400> SEQUENCE: 36
ctactagaaa gaagggcgtc aaaaatctgc tatgctatta cgaaattact ctataggtta      60
gaatgtcatc ccataggtat ggccctttta aagaagtatc tccacaatca attgcgagaa     120
gcctatctag aatcaaaacg acactttatt tccaaaaagg gagattcgac caacacttcc     180
tctaccattg catcatcatc tttcgctggc gcatctgttc ctctatcttc aaacgaatca     240
ggaatgctaa acggcttgaa gcaaattaac gaacaacaag aatctacatt agaaaccact     300
caaaaggaag actagtaacg ccgtatcgtg attaacgtat tacataagtt acaggattca     360
tgcttatggg ttagctattt cgcccaatgt gtccatctga cattactatt ttgcatttta     420
atttaattag aacttgacta gcgcactacc agtatatcat ctcatttccg taaataccaa     480
atgtattata tattgaaagc ttttgaccag gttattataa aagaaacttc atgctcgaaa     540
aagatcattt cgaaaagttg cctagtttca tgaaatttta aagcagttta tataaatttt     600 acctttгgat gcggaattga cttttcttg aataatacat aacttttctt aaaagaatca     660
aagacagata aaatttaaga gatattaaat attagtgaga agccgagaat tttgtaacac     720
```

```
caacataaca ctgacatctt taacaacttt taattatgat acatttctta cgtcatgatt      780
gattattaca gctatgctga caaatgactc ttgttgcatg gctacgaacc gggtaatact      840
aagtgattga ctcttgctga ccttttatta agaactaaat ggacaatatt atggagcatt      900
tcatgtataa attggtgcgt aaaatcgttg gatctctctt ctaagtacat cctactataa     960
caatcaagaa aaacaagaaa atcggacaaa acaatcaagt atggattcta gaacagttgg     1020
tatattagga gggggacaat tgggacgtat gattgttgag gcagcaaaca ggctcaacat     1080
taagacggta atactagatg ctgaaaattc tcctgccaaa caaataagca actccaatga     1140
ccacgttaat ggctccttttt ccaatcctct tgatatcgaa aaactagctg aaaaatgtga     1200
tgtgctaacg attgagattg agcatgttga tgttcctaca ctaaagaatc ttcaagtaaa     1260
acatcccaaa ttaaaaattt acccttctcc agaaacaatc agattgatac aagcaaata     1320 tattcaaaaa gagcatttaa tcaaaaatgg tatagcagtt acccaaagtg ttcctgtgga     1380
acaagccagt gagacgtccc tattgaatgt tggaagagat ttgggttttc cattcgtctt     1440
gaagtcgagg actttggcat acgatggaag aggtaacttc gttgtaaaga ataaggaaat     1500
gattccggaa gctttggaag tactgaagga tcgtcctttg tacgccgaaa aatgggcacc     1560
atttactaaa gaattagcag tcatgattgt gagatctgtt aacggtttag tgttttctta     1620
cccaattgta gagactatcc acaaggacaa tatttgtgac ttatgttatc gcctgctag      1680 agttccggac tccgttcaac ttaaggcgaa gttgttggca gaaaatgcaa tcaaatcttt     1740
tcccggttgt ggtatatttg gtgtggaaat gttctattta gaaacagggg aattgcttat     1800
taacgaaatt gccccaaggc ctcacaactc tggacattat accattgatg cttgcgtcac     1860
ttctcaattt gaagctcatt tgagatcaat attggatttg ccaatgccaa agaatttcac     1920
atctttctcc accattacaa cgaacgccat tatgctaaat gttcttggag acaaacatac     1980
aaaagataaa gagctagaaa cttgcgaaag agcattggcg actccaggtt cctcagtgta     2040
cttatatgga aaagagtcta gacctaacag aaaagtaggt cacataaata ttattgcctc     2100
cagtatggcg gaatgtgaac aaaggctgaa ctacattaca ggtagaactg atattccaat     2160
caaaatctct gtcgctcaaa agttggactt ggaagcaatg gtcaaaccat ggttggaat      2220 catcatggga tcagactctg acttgccggt aatgtctgcc gcatgtgcgg ttttaaaga      2280 ttttggcgtt ccatttgaag tgacaatagt ctctgctcat agaactccac ataggatgtc     2340
agcatatgct atttccgcaa gcaagcgtgg aattaaaaca attatcgctg gagctggtgg     2400
ggctgctcac ttgccaggta tggtggctgc aatgacacca cttcctgtca tcggtgtgcc     2460
cgtaaaaggt tcttgtctag atggagtaga ttctttacat tcaattgtgc aaatgcctag     2520
aggtgttcca gtagctaccg tcgctattaa taatagtacg aacgctgcgc tgttggctgt     2580
cagactgctt ggcgcttatg attcaagtta tacaacgaaa atggaacagt ttttattaaa     2640
gcaagaagaa gaagttcttg tcaaagcaca aaagttagaa actgtcggtt acgaagctta     2700
tctagaaaac aagtaatata taagtttatt gatatacttg tacagcaaat aattataaaa     2760
tgatatacct attttttagg ctttgttatg attacatcaa atgtggactt catacataga     2820
aatcaacgct tacaggtgtc ctttttaag aatttcatac ataagatcac ttattataca     2880
tacatacata tccagtaaca agaagcaagg aataattacc tgcttaagtc tgcgattaaa     2940
aaaataacgt ttcgatacag ttcatataag gcggctcaat gcagaaccga ggatagcgct     3000
acgtcaggat atctttgtag ttcccaaata taaatgcgac aatatagttt ctttctttca     3060
tatcaataat atccttttct ccactgaaat cacgaatcaa acctggagca aaaactaaag     3120
```

```
ccaaattata aagcgtcatt cgattccagt gactgtaccg tgtaaccttt tctatatgtt    3180
cactcagtac tcttaacacc ctataatgtt cccttggaag gtcttccaat atgtttttta    3240
aagcgctctt gctcgacata taagtgtccg aattctttgc ttctaaggac aactttcctc    3300
caacaaatgg caagttttcc atcattttt tagatttaac taacctcatc aacggctcgt     3360
atatttgaaa ggtaaagata ggttgggga gctttcttaa gtatcgcttc aacacaccag     3420
taacaacgtt gagatcttgt tccgttaaaa tatttggcgt ttcggtattt tgttgtactt    3480
tccatgcaga aaattgcttt tctatttctt ctatgactag ctgggaacct gattttctat    3540
aaatgccctc cgatctcata tttttcttcgt ctgattcaat aaaatctatg cagacagata   3600
gtatcatcgg tatttcattg ttttcataat tgcacctagc aacgagactt gaaccataca    3660
aattgcttcc atccaaatat tcttctccat ctttactttg tcccatattt gcatcg        3716
```

<210> SEQ ID NO 37
<211> LENGTH: 22
<212> TYPE: DNA
<213> ORGANISM: Artificial sequence
<220> FEATURE:
<223> OTHER INFORMATION: MS26 intended recognition sequence

<400> SEQUENCE: 37

```
gatggtgacg tacgtgccct ac                                                22
```

<210> SEQ ID NO 38
<211> LENGTH: 16824
<212> TYPE: DNA
<213> ORGANISM: Artificial sequence
<220> FEATURE:
<223> OTHER INFORMATION: plasmid PHP57712
<220> FEATURE:
<221> NAME/KEY: misc_feature
<222> LOCATION: (12027)..(12027)
<223> OTHER INFORMATION: n is a, c, g, or t

<400> SEQUENCE: 38

```
ggagatccaa gcttggcgcg ccggcctctg cctgcgttct gctgtggaag ttcctattcc      60
gaagttccta ttctccagaa agtataggaa cttcacatgc tgcctcgtgc aagtcacgat     120
ctcgagttct atagtgtcac ctaaatcgta tgtgtatgat acataaggtt atgtattaat     180
tgtagccgcg ttctaacgac aatatgtcca tatggtgcac tctcagtaca atctgctctg    240
atgccgcata gttaagccag ccccgacacc cgccaacacc cgctgacgcg ccctgacggg    300
cttgtctgct cccggcatcc gcttacagac aagctgtgac cgtctccggg agctgcatgt    360
gtcagaggtt ttcaccgtca tcaccgaaac gcgcgagacg aaagggcctc gtgatacgcc    420
tatttttata ggttaatgtc atgaccaaaa tcccttaacg tgagttttcg ttccactgag    480
cgtcagaccc cgtagaaaag atcaaaggat cttcttgaga tcctttttt ctgcgcgtaa     540 tctgctgctt gcaaacaaaa aaaccaccgc taccagcggt ggtttgtttg ccggatcaag    600
agctaccaac tctttttccg aaggtaactg gcttcagcag agcgcagata ccaaatactg    660
tccttctagt gtagccgtag ttaggccacc acttcaagaa ctctgtagca ccgcctacat    720
acctcgctct gctaatcctg ttaccagtgg ctgctgccag tggcgataag tcgtgtctta    780
ccgggttgga ctcaagacga tagttaccgg ataaggcgca gcggtcgggc tgaacggggg    840
gttcgtgcac acagcccagc ttggagcgaa cgacctacac cgaactgaga tacctacagc    900
gtgagcattg agaaagcgcc acgcttcccg aagggagaaa ggcggacagg tatccggtaa    960
```

-continued

```
gcggcagggt cggaacagga gagcgcacga gggagcttcc aggggaaaac gcctggtatc      1020
tttatagtcc tgtcgggttt cgccacctct gacttgagcg tcgatttttg tgatgctcgt      1080
caggggggcg gagcctatgg aaaaacgcca gcaacgcggc cttttacgg ttcctggcct       1140 tttgctggcc ttttgctcac atgttctttc ctgcgttatc ccctgattct gtggataacc      1200
gtattaccgc ctttgagtga gctgataccg ctcgccgcag ccgaacgacc gagcgcagcg      1260
agtcagtgag cgaggaagcg gaagagcgcc aatacgcaa accgcctctc cccgcgcgtt       1320
ggccgattca ttaatgcagg ttgatcagat ctcgatcccg cgaaattaat acgactcact      1380
atagggagac cacaacggtt ccctctaga aataattttg tttaacttta agaaggagat       1440
atacccatgg aaaagcctga actcaccgcg acgtctgtcg agaagtttct gatcgaaaag      1500
ttcgacagcg tctccgacct gatgcagctc tcggagggcg aagaatctcg tgctttcagc      1560
ttcgatgtag gagggcgtgg atatgtcctg cgggtaaata gctgcgccga tggtttctac      1620
aaagatcgtt atgtttatcg gcactttgca tcggccgcgc tcccgattcc ggaagtgctt      1680
gacattgggg aattcagcga gagcctgacc tattgcatct cccgccgtgc acagggtgtc      1740
acgttgcaag acctgcctga aaccgaactg cccgctgttc tgcagccggt cgcggaggct      1800
atggatgcga tcgctgcggc cgatcttagc cagacgagcg ggttcggccc attcggaccg      1860
caaggaatcg gtcaatacac tacatggcgt gatttcatat gcgcgattgc tgatccccat      1920
gtgtatcact ggcaaactgt gatggacgac ccgtcagtg cgtccgtcgc gcaggctctc       1980
gatgagctga tgctttgggc cgaggactgc cccgaagtcc ggcacctcgt gcacgcggat      2040
ttcggctcca acaatgtcct gacgacaat ggccgcataa cagcggtcat tgactggagc       2100
gaggcgatgt tcggggattc ccaatacgag gtcgccaaca tcttcttctg gaggccgtgg      2160
ttggcttgta tggagcagca gacgcgctac ttcgagcgga ggcatccgga gcttgcagga     2220
tcgccgcggc tccgggcgta tatgctccgc attggtcttg accaactcta tcagagcttg     2280
gttgacggca atttcgatga tgcagcttgg gcgcagggtc gatgcgacgc aatcgtccga     2340
tccggagccg ggactgtcgg cgtacacaa atcgcccgca gaagcgcggc cgtctggacc      2400
gatggctgtg tagaagtact cgccgatagt ggaaaccgac gccccagcac tcgtccgagg     2460
gcaaaggaat agtgaggtac agcttggatc gatccggctg ctaacaaagc ccgaaggaa      2520 gctgagttgg ctgctgccac cgctgagcaa taactagcat aacccttgg ggcctctaaa      2580 cgggtcttga ggggtttttt gctgaaagga ggaactatat ccggatgatc gtcgaggcct     2640
cacgtgttaa cagaagttcc tattccgaag ttcctattct ctagaaagta taggaacttc     2700
caccacacaa cacaatggcg gccaccgctt ccagaaccac ccgattctct tcttcctctt      2760 cacccccac cttccccaaa cgcattacta gatccaccct ccctctctct catcaaaccc       2820
tcaccaaacc caaccacgct ctcaaaatca atgttccat ctccaaaccc ccacggcgg       2880 cgcccttcac caaggaagcg ccgaccacgg agcccttcgt gtcacggttc gcctccggcg     2940
aacctcgcaa gggcgcggac atccttgtgg aggcgctgga gaggcagggc gtgacgacgg     3000
tgttcgcgta cccggcggt gcgtcgatgg agatccacca ggcgctcacg cgctccgccg      3060
ccatccgcaa cgtgctcccg cgccacgagc agggcggcgt cttcgccgcc gaaggctacg     3120
cgcgttcctc cggcctcccc ggcgtctgca ttgccacctc cggccccggc gccaccaacc     3180
tcgtgagcgg cctcgccgac gctttaatgg acagcgtccc agtcgtcgcc atcaccggcc     3240
aggtcagccg ccgatgatc ggcaccgacg ccttccaaga aacccgatc gtggaggtga      3300 gcagatccat cacgaagcac aactacctca tcctcgacgt cgacgacatc ccccgcgtcg     3360
```

```
tcgccgaggc tttcttcgtc gccacctccg gccgccccgg tccggtcctc atcgacattc    3420
ccaaagacgt tcagcagcaa ctcgccgtgc ctaattggga cgagcccgtt aacctccccg    3480
gttacctcgc caggctgccc aggcccccg ccgaggccca attggaacac attgtcagac     3540
tcatcatgga ggcccaaaag cccgttctct acgtcggcgg tggcagtttg aattccagtg    3600
ctgaattgag gcgctttgtt gaactcactg gtattcccgt tgctagcact ttaatgggtc    3660
ttggaacttt tcctattggt gatgaatatt cccttcagat gctgggtatg catggtactg    3720
tttatgctaa ctatgctgtt gacaatagtg atttgttgct tgcctttggg gtaaggtttg    3780
atgaccgtgt tactgggaag cttgaggctt ttgctagtag ggctaagatt gttcacattg    3840
atattgattc tgccgagatt gggaagaaca agcaggcgca cgtgtcggtt tgcgcggatt    3900
tgaagttggc cttgaaggga attaatatga ttttggagga gaaaggagtg gagggtaagt    3960
ttgatcttgg aggttggaga gaagagatta atgtgcagaa acacaagttt ccattgggtt    4020
acaagacatt ccaggacgcg atttctccgc agcatgctat cgaggttctt gatgagttga    4080
ctaatggaga tgctattgtt agtactgggg ttgggcagca tcaaatgtgg gctgcgcagt    4140
tttacaagta caagagaccg aggcagtggt tgacctcagg gggtcttgga gccatgggtt    4200
ttggattgcc tgcggctatt ggtgctgctg ttgctaaccc tggggctgtt gtggttgaca    4260
ttgatgggga tggtagtttc atcatgaatg ttcaggagtt ggccactata agagtggaga    4320
atctcccagt taagatattg ttgttgaaca atcagcattt gggtatggtg gttcagtggg    4380
aggataggtt ctacaagtcc aatagagctc acacctatct tggagatccg tctagcgaga    4440
gcgagatatt cccaaacatg ctcaagtttg ctgatgcttg tgggataccg gcagcgcgag    4500
tgacgaagaa ggaagagctt agagcggcaa ttcagagaat gttggacacc cctggcccct    4560
accttcttga tgtcattgtg ccccatcagg agcatgtgtt gccgatgatt cccagtaatg    4620
gatccttcaa ggatgtgata actgagggtg atggtagaac gaggtactga ttgcctagac    4680
caaatgttcc ttgatgcttg ttttgtacaa tatatataag ataatgctgt cctagttgca    4740
ggatttggcc tgtggtgagc atcatagtct gtagtagttt tggtagcaag acattttatt    4800
ttccttttat ttaacttact acatgcagta gcatctatct atctctgtag tctgatatct    4860
cctgttgtct gtattgtgcc gttggatttt ttgctgtagt gagactgaaa atgatgtgct    4920
agtaataata tttctgttag aaatctaagt agagaatctg ttgaagaagt caaaagctaa    4980
tggaatcagg ttacatattc aatgtttttc ttttttttagc ggttggtaga cgtgtagatt    5040
caacttctct tggagctcac ctaggcaatc agtaaaatgc atattccttt tttaacttgc    5100
catttattta cttttagtgg aaattgtgac caatttgttc atgtagaacg gatttggacc    5160
attgcgtcca caaacgtct cttttgctcg atcttcacaa agcgataccg aaatccagag     5220
atagttttca aaagtcagaa atggcaaagt tataaatagt aaaacagaat agatgctgta    5280
atcgacttca ataacaagtg gcatcacgtt tctagttcta gacccatcag gggcagatct    5340
aggcgcgcgc catataccct cacacgtacgc gtagatggtg acgtacgtgc cctaccaaac   5400
agattcacgt cagatttgaa gttcctattc cgaagttcct attctacata gagtatagga   5460
acttccgata tcactgcagt ggccggcggc gcgccgtcga cggatccgta cgatccatgc   5520
ccttcatttg ccgcttatta attaatttgg taacagtccg tactaatcag ttacttatcc   5580
ttcccccatc ataattaatc ttggtagtct cgaatgccac aacactgact agtctcttgg   5640
atcataagaa aaagccaagg aacaaaagaa gacaaaacac aatgagagta tcctttgcat   5700
```

```
agcaatgtct aagttcataa aattcaaaca aaaacgcaat cacacacagt ggacatcact    5760
tatccactag ctgatcagga tcgccgcgtc aagaaaaaaa aactggaccc caaaagccat    5820
gcacaacaac acgtactcac aaaggtgtca atcgagcagc ccaaaacatt caccaactca    5880
acccatcatg agccctcaca tttgttgttt ctaacccaac ctcaaactcg tattctcttc    5940
cgccacctca ttttgttta tttcaacacc cgtcaaactg catgccaccc cgtggccaaa    6000
tgtccatgca tgttaacaag acctatgact ataaatagct gcaatctcgg cccaggtttt    6060
catcatcaag aaccagttca atatcctagt acaccgtatt aaagaattta agatatactg    6120
cggccgcatg actatcgact cacaatacta caagtcgcga gacaaaaacg acacggcacc    6180
caaaatcgcg ggaatccgat atgccccgct atcgacacca ttactcaacc gatgtgagac    6240
cttctctctg gtctggcaca ttttcagcat tcccactttc ctcacaattt tcatgctatg    6300
ctgcgcaatt ccactgctct ggccatttgt gattgcgtat gtagtgtacg ctgttaaaga    6360 cgactcccg tccaacggag gagtggtcaa gcgatactcg cctatttcaa gaaacttctt    6420
catctggaag ctctttggcc gctacttccc cataactctg cacaagacgg tggatctgga    6480
gcccacgcac acatactacc ctctggacgt ccaggagtat cacctgattg ctgagagata    6540
ctggccgcag aacaagtacc tccgagcaat catcaccacc atcgagtact ttctgcccgc    6600
cttcatgaaa cggtctcttt ctatcaacga gcaggagcag cctgccgagc gagatcctct    6660
cctgtctccc gtttctccca gctctccggg ttctcaacct gacaagtgga ttaaccacga    6720
cagcagatat agccgtggag aatcatctgg ctccaacggc cacgcctcgg gctccgaact    6780
taacggcaac ggcaacaacg gcaccactaa ccgacgacct tgtcgtccg cctctgctgg    6840 ctccactgca tctgattcca cgcttcttaa cgggtccctc aactcctacg ccaaccagat    6900
cattggcgaa aacgacccac agctgtcgcc cacaaaactc aagcccactg gcagaaaata    6960
catcttcggc taccaccccc acggcattat cggcatggga gcctttggtg gaattgccac    7020
cgagggagct ggatggtcca agctcttcc gggcatccct gtttctctta tgactctcac    7080
caacaacttc cgagtgcctc tctacagaga gtacctcatg agtctgggag tcgcttctgt    7140
ctccaagaag tcctgcaagg ccctcctcaa gcgaaaccag tctatctgca ttgtcgttgg    7200
tggagcacag gaaagtcttc tggccagacc cggtgtcatg gacctggtgc tactcaagcg    7260
aaagggtttt gttcgacttg gtatggaggt cggaaatgtc gcccttgttc ccatcatggc    7320
ctttggtgag aacgacctct atgaccaggt tagcaacgac aagtcgtcca agctgtaccg    7380
attccagcag tttgtcaaga acttccttgg attcacccct cctttgatgc atgcccgagg    7440
cgtcttcaac tacgatgtcg gtcttgtccc ctacaggcga cccgtcaaca ttgtggttgg    7500
ttcccccatt gacttgcctt atctcccaca ccccaccgac gaagaagtgt ccgaatacca    7560
cgaccgatac atcgccgagc tgcagcgaat ctacaacgag cacaaggatg aatatttcat    7620
cgattggacc gaggagggca aaggagcccc agagttccga atgattgagt aagcggccgc    7680
aagtatgaac taaaatgcat gtaggtgtaa gagctcatgg agagcatgga atattgtatc    7740
cgaccatgta acagtataat aactgagctc catctcactt cttctatgaa taaacaaagg    7800
atgttatgat atattaacac tctatctatg caccttattg ttctatgata aatttcctct    7860
tattattata aatcatctga atcgtgacgg cttatggaat gcttcaaata gtacaaaaac    7920
aaatgtgtac tataagactt tctaaacaat tctaacctta gcattgtgaa cgagacataa    7980
gtgttaagaa gacataacaa ttataatgga agaagtttgt ctccatttat atattatata    8040
ttacccactt atgtattata ttaggatgtt aaggagacat aacaattata aagagagaag    8100
```

```
tttgtatcca tttatatatt atatactacc catttatata ttatacttat ccacttattt    8160
aatgtcttta taaggtttga tccatgatat ttctaatatt ttagttgata tgtatatgaa    8220
aaggtactat ttgaactctc ttactctgta taaaggttgg atcatcctta aagtgggtct    8280
atttaatttt attgcttctt acagataaaa aaaaaattat gagttggttt gataaaatat    8340
tgaaggattt aaataataa taaataacat ataatatatg tatataaatt tattataata    8400
taacatttat ctataaaaaa gtaaatattg tcataaatct atacaatcgt ttagccttgc    8460
tggaacgaat ctcaattatt taaacgagag taaacatatt tgacttttg gttatttaac    8520
aaattattat ttaacactat atgaaatttt tttttttatc agcaaagaat aaaattaaat    8580
taagaaggac aatggtgtcc caatccttat acaaccaact tccacaagaa agtcaagtca    8640
gagacaacaa aaaacaagc aaaggaaatt ttttaatttg agttgtcttg tttgctgcat    8700
aatttatgca gtaaaacact acacataacc cttttagcag tagagcaatg gttgaccgtg    8760
tgcttagctt ctttattt attttttttat cagcaaagaa taaataaaat aaaatgagac    8820
acttcaggga tgtttcaacg tactttctag acgtacgtct ttccacaata cataactatt    8880
aattaatctt aaataaataa aggataaaat attttttttt cttcataaag ttaaaatatg    8940
ttattttttg tttagatgta tattcgaata aatctaaata tatgataatg atttttttata    9000
ttgattaaac atataatcaa tattaaatat gatatttttt tatataggtt gtacacataa    9060
ttttataagg ataaaaaata tgataaaaat aaatttttaaa tattttttata tttacgagaa    9120
aaaaaaatat tttagccata aataaatgac cagcatattt tacaacctta gtaattcata    9180
aattcctata tgtatatttg aaattaaaaa cagataatcg ttaagggaag gaatcctacg    9240
tcatctcttg ccatttgttt ttcatgcaaa cagaaaggga cgaaaaacca cctcaccatg    9300
aatcactctt cacaccattt ttactagcaa acaagtctca acaactgaag ccagctctct    9360
ttccgttctt ttttacaaca cttttctttga aatagtagta ttttttttca catgattat    9420
taacgtgcca aaagatgctt attgaataga gtgcacattt gtaatgtact actaattaga    9480
acatgaaaaa gcattgttct aacacgataa tcctgtgaag gcgttaactc caaagatcca    9540
atttcactat ataaattgtg acgaaagcaa atgaattca catagctgag agagaaagga    9600
aaggttaact aagaagcaat acttcagcgg ccgcttctag ctagctaggg tttgggtagt    9660
gagtgtaata aagttgcaaa gttttggtt aggttacgtt ttgaccttat tattatagtt    9720
caaagggaaa cattaattaa aggggattat gaagtgggct ctcttgattc ttggatgagg    9780
atcttactgg gtgaattgag ctgcttagct atggatccca cagttctacc catcaataag    9840
tgcttttgtg gtagtcttgt ggcttccata tctggggagc ttcatttgcc tttatagtat    9900
taaccttctc caagaacaaa gagagcccac accttctct tctttctct cataataatt    9960
taaatttgtt atagactcta aactttaaat gttttttttg aagttttcc gttttctct   10020
tttgccatga tcccgttctt gctgtggagt aaccttgtcc gaggtatgtg catgattaga   10080
tccatactta atttgtgtgc atcacgaagg tgaggttgaa atgaactttg cttttttgac   10140
cttttaggaa agttcttttg ttgcagtaat caatttttaat tagttttaat tgacactatt   10200
acttttattg tcatctttgt tagttttatt gttgaattga gtgcatatttt cctaggaaat   10260
tctcttacct aacatttttt atacagatct atgctcttgg ctcttgccct tactcttggc   10320
cttgtgttgg ttatttgtct acatatttat tgactggtcg atgagacatg tcacaattct   10380
tgggcttatt tgttggtcta ataaaaggag tgcttattga aagatcaaga cggagattcg   10440
```

```
gttttatata aataaactaa agatgacata ttagtgtgtt gatgtctctt caggataatt    10500
tttgtttgaa ataatatggt aatgtcttgt ctaaatttgt gtacataatt cttactgatt    10560
ttttggattg ttggatttttt ataaacaaat ctgcggccgc atgagccgta aaggttcaat   10620
acaacgagtg cttgttttct tagggacaag cattgtactt atgtatgatt ctgtgtaacc    10680
atgagtcttc cacgttgtac taatgtgaag ggcaaaaata aaacacagaa caagttcgtt    10740
tttctcaaat aatgtgaagg tagaaaatgg aaccatgcct cctctcttgc atgtgattta    10800
aaatattagc agatggtacg tcgagtcgac ctgcaggtcg actcgacgta cgtcctcgaa    10860
gagaagggtt aataacacat tttttaacat ttttaacaca aattttagtt atttaaaaat    10920
ttattaaaaa atttaaaata agaagaggaa ctctttaaat aaatctaact tacaaaattt    10980
atgatttta ataagttttc accaataaaa aatgtcataa aaatatgtta aaagtatat     11040
tatcaatatt ctcttatga taaataaaaa gaaaaaaaaa ataaagtta agtgaaaatg      11100
agattgaagt gacttaggt gtgtataaat atatcaaccc cgccaacaat ttatttaatc     11160
caaatatatt gaagtatatt attccatagc ctttatttat ttatatattt attatataaa   11220
agctttattt gttctaggtt gttcatgaaa tattttttg gtttatctc cgttgtaaga     11280
aaatcatgtg ctttgtgtcg ccactcacta ttgcagcttt tcatgcatt ggtcagattg     11340
acggttgatt gtatttttgt tttttatggt tttgtgttat gacttaagtc ttcatctctt   11400
tatctcttca tcaggtttga tggttaccta atatggtcca tgggtacatg catggttaaa   11460
ttaggtggcc aactttgttg tgaacgatag aattttttt atattaagta aactattttt    11520
atattatgaa ataataataa aaaaaatatt ttatcattat taacaaaatc atattagtta   11580
atttgttaac tctataataa aagaaatact gtaacattca cattacatgg taacatcttt   11640
ccacccttc atttgttttt tgtttgatga cttttttct tgtttaaatt tatttcccctt   11700
cttttaaatt tggaatacat tatcatcata tataaactaa aatactaaaa acaggattac   11760
acaaatgata aataataaca caaatattta taaatctagc tgcaatatat ttaaactagc    11820
tatatcgata ttgtaaaata aaactagctg cattgatact gataaaaaaa tatcatgtgc    11880
tttctggact gatgatgcag tatacttttg acattgcctt tattttattt ttcagaaaag   11940
ctttcttagt tctgggttct tcattatttg tttcccatct ccattgtgaa ttgaatcatt   12000
tgcttcgtgt cacaaataca atttagntag gtacatgcat tggtcagatt cacgttttat   12060
tatgtcatga cttaagttca tggtagtaca ttacctgcca cgcatgcatt atattggtta   12120
gatttgatag gcaaatttgg ttgtcaacaa tataaatata aataatgttt ttatattacg    12180
aaataacagt gatcaaaaca aacagttta tctttattaa caagattttg ttttgtttg     12240
atgacgtttt ttaatgttta cgctttcccc cttcttttga atttagaaca ctttatcatc   12300
ataaaatcaa atactaaaaa aattacatat ttcataaata ataacacaaa tattttaaa    12360
aaatctgaaa taataatgaa caatattaca tattatcacg aaaattcatt aataaaaata   12420
ttatataaat aaaaatgtaat agtagttata tgtaggaaaa aagtactgca cgcataatat  12480
atacaaaaag attaaaatga actattataa ataataacac taaattaatg gtgaatcata   12540
tcaaaataat gaaaaagtaa ataaaatttg taattaactt ctatatgtat tacacacaca   12600
aataataaat aatagtaaaa aaaattatga taaatattta ccatctcata agatatttaa   12660
aataatgata aaaatataga ttattttta tgcaactagc tagccaaaaa gagaacacgg    12720
gtatatataa aaagagtacc tttaaattct actgtacttc ctttattcct gacgttttta   12780
tatcaagtgg acatacgtga agattttaat tatcagtcta aatatttcat tagcacttaa   12840
```

```
tactttttctg ttttattcct atcctataag tagtcccgat tctcccaaca ttgcttattc   12900
acacaactaa ctaagaaagt cttccatagc cccccaagcg gccgctagtc gactaagtca   12960
tcaactattc caagctacgt atttgggagt ttgtggagta cagcaagatg atatacctag   13020
acggtgatat ccaagttttt gacaacattg accacttgtt tgacttgcct gataactact   13080
tctatgcggt gatggactgt ttctgtgagc caacttgggg ccacactaaa caatatcaga   13140
tcggttactg ccagcagtgc ccccataagg ttcagtggcc cactcacttt gggcccaaac   13200
ctcctctcta tttcaatgct ggcatgtttg tgtatgagcc caatttggct acttaccgtg   13260
acctccttca aacagtccaa gtcacccagc ccacttcctt tgctgaacag gattttttga   13320
acatgtactt caaggacaaa tataggccaa ttcctaatgt ctacaatctt gtgctggcca   13380
tgctgtggcg tcaccctgag aacgttgagc ttgacaaagt taaagtggtt cactactgtg   13440
ctgctgggtc taagccttgg aggtacactg ggaagtgact cgaggtcatc aattactcca   13500
agctacgtat ttgggagttc gtggagtaca agaagacgat atacctagac ggtgacatcc   13560
aagtatttgg aaacatagac cacttgtttg atctgcctga taattatttc tatgcggtga   13620
tggattgttt ctgcgagaag acttggagcc acacccctca gttccagatt gggtactgcc   13680
aacagtgccc tgataaggtt caatggccct ctcactttgg ttccaaacct cctctatatt   13740
tcaatgctgg catgtttgtt tatgagccta atctcgacac ctaccgtgat cttctccaaa   13800
ctgtccaact caccaagccc acttcttttg ctgagcagga ctttctcaac atgtacttca   13860
aggacaagta caagccaata ccgaacatgt acaaccttgt gctggccatg ttgtggcgtc   13920
accctgaaaa tgttgaactt gataaagttc aagtggttca ttactgtgct gctgggtcta   13980
agccttggag gttcactggg aagtaactgc aggtcatcaa ctactccaag ctccgtatat   14040
gggagtttgt ggagtacagc aagatgatat acttggacgg agacattgag gtatatgaga   14100
acatagacca cctatttgac ctacctgatg gtaacttttta cgctgtgatg gattgtttct   14160
gcgagaagac atggagtcac acccctcagt acaaggtggg ttactgccag caatgcccgg   14220
agaaggtgcg gtggcccacc gaattgggtc agccccctt ctctttacttc aacgctggca   14280 tgttcgtgtt cgaacccaac atcgccacct atcatgacct attgaaaacg gtgcaagtca   14340
ccactcccac ctcgttcgct gaacaagatt tcttgaacat gtacttcaag gacatttaca   14400
agccaatccc tttaaattac aatcttgtcc tcgccatgct gtggcgccac ccggaaaacg   14460
ttaaattaga ccaagtcaag gttgttcact attgcgcagc ggggtccaag ccatggagat   14520
atacggggaa gtagcctagg cgtacgcagg taagttctg cttctacctt tgatatat   14580 ataataatta tcattaatta gtagtaatat aatatttcaa atattttttt caaaataaaa   14640
gaatgtagta tatagcaatt gctttttctgt agttttataag tgtgtatatt ttaatttata   14700
acttttctaa tatatgacca aaacatggtg atgtgcaggt cctaggctac ttccccgtat   14760
atctccatgg cttggacccc gctgcgcaat agtgaacaac cttgacttgg tctaatttaa   14820
cgttttccgg gtggcgccac agcatggcga ggacaagatt gtaattaaa gggattggct   14880 tgtaaatgtc cttgaagtac atgttcaaga aatcttgttc agcgaacgag gtgggagtgg   14940
tgacttgcac cgtttttcaat aggtcatgat aggtggcgat gttgggttcg aacacgaaca   15000
tgccagcgtt gaagtaaaga gaagggggct gacccaattc ggtgggccac cgcaccttct   15060
ccgggcattg ctggcagtaa cccaccttgt actgaggggt gtgactccat gtcttctcgc   15120
agaaacaatc catcacagcg taaaagttac catcaggtag gtcaaatagg tggtctatgt   15180
```

| | |
|---|---|
| tctcatatac ctcaatgtct ccgtccaagt atatcatctt gctgtactcc acaaactccc | 15240 |
| atatacggag cttggagtag ttgatgacct gcagttactt cccagtgaac ctccaaggct | 15300 |
| tagacccagc agcacagtaa tgaaccactt gaactttatc aagttcaaca tttttcagggt | 15360 |
| gacgccacaa catggccagc acaaggttgt acatgttcgg tattggcttg tacttgtcct | 15420 |
| tgaagtacat gttgagaaag tcctgctcag caaaagaagt gggcttggtg agttggacag | 15480 |
| tttggagaag atcacggtag gtgtcgagat taggctcata acaaacatg ccagcattga | 15540 |
| aatatagagg aggtttggaa ccaaagtgag agggccattg aaccttatca gggcactgtt | 15600 |
| ggcagtaccc aatctggaac tgaggggtgt ggctccaagt cttctcgcag aaacaatcca | 15660 |
| tcaccgcata gaaataatta tcaggcagat caaacaagtg gtctatgttt ccaaatactt | 15720 |
| ggatgtcacc gtctaggtat atcgtcttct tgtactccac gaactcccaa atacgtagct | 15780 |
| tggagtaatt gatgacctcg agtcacttcc cagtgtacct ccaaggctta gacccagcag | 15840 |
| cacagtagtg aaccacttta actttgtcaa gctcaacgtt ctcagggtga cgccacagca | 15900 |
| tggccagcac aagattgtag acattaggaa ttggcctata tttgtccttg aagtacatgt | 15960 |
| tcaaaaaatc ctgttcagca aaggaagtgg gctgggtgac ttggactgtt tgaaggaggt | 16020 |
| cacggtaagt agccaaattg ggctcataca caaacatgcc agcattgaaa tagagaggag | 16080 |
| gtttgggccc aaagtgagtg ggccactgaa ccttatgggg gcactgctgg cagtaaccga | 16140 |
| tctgatattg tttagtgtgg ccccaagttg gctcacagaa acagtccatc accgcataga | 16200 |
| agtagttatc aggcaagtca acaagtggt caatgttgtc aaaaacttgg atatcaccgt | 16260 |
| ctaggtatat catcttgctg tactccacaa actcccaaat acgtagcttg aatagttga | 16320 |
| tgacttagtc gactagcggc cgcgacacaa gtgtgagagt actaaataaa tgctttggtt | 16380 |
| gtacgaaatc attacactaa ataaaataat caaagcttat atatgccttc cgctaaggcc | 16440 |
| gaatgcaaag aaattggttc tttctcgtta tcttttgcca ctttactag tacgtattaa | 16500 |
| ttactactta atcatctttg tttacggctc attatatccg gtctaggcca aggccgcgaa | 16560 |
| gttaaaagca atgttgtcac ttgtacgtac taacacatga tgtgatagtt tatgctagct | 16620 |
| agctataaca taagctgtct ctgagtgtgt tgtatattaa taaagatcat cactggtgaa | 16680 |
| tggtgatcgt gtacgtaccc tacttagtag gcaatggaag cacttagagt gtgctttgtg | 16740 |
| catggccttg cctctgtttt gagacttttg taatgttttc gagtttaaat ctttgccttt | 16800 |
| gcgtacgtgg gcggatcccc tgca | 16824 |

<210> SEQ ID NO 39
<211> LENGTH: 16822
<212> TYPE: DNA
<213> ORGANISM: Artificial sequence
<220> FEATURE:
<223> OTHER INFORMATION: plasmid PHP62552
<220> FEATURE:
<221> NAME/KEY: misc_feature
<222> LOCATION: (9373)..(9373)
<223> OTHER INFORMATION: n is a, c, g, or t

<400> SEQUENCE: 39

| | |
|---|---|
| gaagttccta ttccgaagtt cctattctct agaaagtata ggaacttcca ccacacaaca | 60 |
| caatggcggc caccgcttcc agaaccaccc gattctcttc ttcctcttca cccccacct | 120 |
| tccccaaacg cattactaga tccaccctcc ctctctctca tcaaaccctc accaaaccca | 180 |
| accacgctct caaatcaaa tgttccatct ccaaaccccc cacggcggcg cccttccacca | 240 |
| aggaagcgcc gaccacggag cccttcgtgt cacggttcgc ctccggcgaa cctcgcaagg | 300 |

```
gcgcggacat ccttgtggag gcgctggaga ggcagggcgt gacgacggtg ttcgcgtacc    360
ccggcggtgc gtcgatggag atccaccagg cgctcacgcg ctccgccgcc atccgcaacg    420
tgctcccgcg ccacgagcag ggcggcgtct tcgccgccga aggctacgcg cgttcctccg    480
gcctccccgg cgtctgcatt gccacctccg gccccgcgc caccaacctc gtgagcggcc    540
tcgccgacgc tttaatggac agcgtcccag tcgtcgccat caccggccag gtcagccgcc    600
ggatgatcgg caccgacgcc ttccaagaaa ccccgatcgt ggaggtgagc agatccatca    660
cgaagcacaa ctacctcatc ctcgacgtcg acgacatccc ccgcgtcgtc gccgaggctt    720
tcttcgtcgc cacctccggc cgccccggtc cggtcctcat cgacattccc aaagacgttc    780
agcagcaact cgccgtgcct aattgggacg agcccgttaa cctccccggt tacctcgcca    840
ggctgcccag gcccccgcc gaggcccaat tggaacacat tgtcagactc atcatggagg    900
cccaaaagcc cgttctctac gtcggcggtg gcagtttgaa ttccagtgct gaattgaggc    960
gctttgttga actcactggt attcccgttg ctagcacttt aatgggtctt ggaactttc    1020 ctattggtga tgaatattcc cttcagatgc tgggtatgca tggtactgtt tatgctaact    1080
atgctgttga caatagtgat ttgttgcttg ccttggggt aaggtttgat gaccgtgtta    1140
ctgggaagct tgaggctttt gctagtaggg ctaagattgt tcacattgat attgattctg    1200
ccgagattgg gaagaacaag caggcgcacg tgtcggtttg cgcggatttg aagttggcct    1260
tgaagggaat aatatgatt ttggaggaga aaggagtgga gggtaagttt gatcttggag    1320
gttggagaga agagattaat gtgcagaaac acaagtttcc attgggttac aagacattcc    1380
aggacgcgat ttctccgcag catgctatcg aggttcttga tgagttgact aatggagatg    1440
ctattgttag tactggggtt gggcagcatc aaatgtgggc tgcgcagttt tacaagtaca    1500
agagaccgag gcagtggttg acctcagggg gtcttggagc catgggtttt ggattgcctg    1560
cggctattgg tgctgctgtt gctaaccctg gggctgttgt ggttgacatt gatgggatg    1620 gtagtttcat catgaatgtt caggagttgg ccactataag agtggagaat ctcccagtta    1680
agatattgtt gttgaacaat cagcatttgg gtatggtggt tcagtgggag ataggttct    1740 acaagtccaa tagagctcac acctatcttg agatccgtc tagcgagagc gagatattcc    1800
caaacatgct caagtttgct gatgcttgtg ggataccggc agcgcgagtg acgaagaagg    1860
aagagcttag agcggcaatt cagagaatgt tggacacccc tggccctac cttcttgatg    1920 tcattgtgcc ccatcaggag catgtgttgc cgatgattcc cagtaatgga tccttcaagg    1980
atgtgataac tgagggtgat ggtagaacga ggtactgatt gcctagacca aatgttcctt    2040
gatgcttgtt ttgtacaata tatataagat aatgctgtcc tagttgcagg atttggcctg    2100
tggtgagcat catagtctgt agtagttttg gtagcaagac attttatttt cctttattt    2160 aacttactac atgcagtagc atctatctat ctctgtagtc tgatatctcc tgttgtctgt    2220
attgtgccgt tggattttt gctgtagtga gactgaaaat gatgtgctag taataatatt    2280
tctgttagaa atctaagtag agaatctgtt gaagaagtca aaagctaatg gaatcaggtt    2340
acatattcaa tgtttttctt tttttagcgg ttggtagacg tgtagattca acttctcttg    2400
gagctcacct aggcaatcag taaaatgcat attccttttt taacttgcca tttatttact    2460
tttagtggaa attgtgacca atttgttcat gtagaacgga tttggaccat tgcgtccaca    2520
aaacgtctct tttgctcgat cttcacaaag cgataccgaa atccagagat agttttcaaa    2580
agtcagaaat ggcaaagtta taaatagtaa aacagaatag atgctgtaat cgacttcaat    2640
```

```
aacaagtggc atcacgtttc tagttctaga cccatcaggg gcagatctag gcgcgccgat    2700
ggtgacgtac gtgccctacc aaacagatgt acgtcatgtt gctatccctc atacgtacgt    2760
gtagaagttc ctattccgaa gttcctattc tacatagagt ataggaactt ccgatatcac    2820
tgcagtggcc ggcggcgcgc cgtcgacgga tccgtacgat ccatgccctt catttgccgc    2880
ttattaatta atttggtaac agtccgtact aatcagttac ttatccttcc cccatcataa    2940
ttaatcttgg tagtctcgaa tgccacaaca ctgactagtc tcttggatca taagaaaaag    3000
ccaaggaaca aagaagaca aaacacaatg agagtatcct ttgcatagca atgtctaagt    3060
tcataaaatt caaacaaaaa cgcaatcaca cacagtggac atcacttatc cactagctga    3120
tcaggatcgc cgcgtcaaga aaaaaaact ggaccccaaa agccatgcac aacaacacgt    3180
actcacaaag gtgtcaatcg agcagcccaa acattcacc aactcaaccc atcatgagcc    3240
ctcacatttg ttgtttctaa cccaacctca aactcgtatt ctcttccgcc acctcatttt    3300
tgtttatttc aacacccgtc aaactgcatg ccaccccgtg gccaaatgtc catgcatgtt    3360
aacaagacct atgactataa atagctgcaa tctcggccca ggttttcatc atcaagaacc    3420
agttcaatat cctagtacac cgtattaaaa aatttaagat atactgcggc gcatgactta    3480
tcgactcaca atactacaag tcgcgagaca aaaacgacac ggcacccaaa atcgcgggaa    3540
tccgatatgc cccgctatcg acaccattac tcaaccgatg tgagaccttc tctctggtct    3600
ggcacatttt cagcattccc actttcctca caattttcat gctatgctgc gcaattccac    3660
tgctctggcc atttgtgatt gcgtatgtag tgtacgctgt taaagacgac tccccgtcca    3720
acggaggagt ggtcaagcga tactcgccta tttcaagaaa cttcttcatc tggaagctct    3780
ttggccgcta cttccccata actctgcaca agacggtgga tctggagccc acgcacacat    3840
actaccctct ggacgtccag gagtatcacc tgattgctga gagatactgg ccgcagaaca    3900
agtacctccg agcaatcatc accaccatcg agtactttct gcccgccttc atgaaacggt    3960
ctctttctat caacgagcag gagcagcctg ccgagcgaga tcctctcctg tctcccgttt    4020
ctcccagctc tccgggttct caacctgaca agtggattaa ccacgacagc agatatagcc    4080
gtggagaatc atctggctcc aacggccacg cctcgggctc cgaacttaac ggcaacggca    4140
acaacggcac cactaaccga cgaccttgt cgtccgcctc tgctggctcc actgcatctg    4200
attccacgct tcttaacggg tccctcaact cctacgccaa ccagatcatt ggcgaaaacg    4260
acccacagct gtcgcccaca aaactcaagc ccactggcag aaaatacatc ttcggctacc    4320
acccccacgg cattatcggc atgggagcct ttggtggaat tgccaccgag ggagctggat    4380
ggtccaagct cttttccgggc atccctgttt ctcttatgac tctcaccaac aacttccgag    4440
tgcctctcta cagagagtac ctcatgagtc tgggagtcgc ttctgtctcc aagaagtcct    4500
gcaaggccct cctcaagcga aaccagtcta tctgcattgt cgttggtgga gcacaggaaa    4560
gtcttctggc cagacccggt gtcatggacc tggtgctact caagcgaaag ggttttgttc    4620
gacttggtat ggaggtcgga aatgtcgccc ttgttcccat catggccttt ggtgagaacg    4680
acctctatga ccaggttagc aacgacaagt cgtccaagct gtaccgattc cagcagtttg    4740
tcaagaactt ccttggattc acccttcctt tgatgcatgc ccgaggcgtc ttcaactacg    4800
atgtcggtct tgtcccctac aggcgacccg tcaacattgt ggttggttcc cccattgact    4860
tgccttatct cccacacccc accgacgaag aagtgtccga ataccacgac cgatacatcg    4920
ccgagctgca gcgaatctac aacgagcaca aggatgaata tttcatcgat tggaccgagg    4980
agggcaaagg agccccagag ttccgaatga ttgagtaagc ggccgcaagt atgaactaaa    5040
```

```
atgcatgtag gtgtaagagc tcatggagag catggaatat tgtatccgac catgtaacag    5100
tataataact gagctccatc tcacttcttc tatgaataaa caaaggatgt tatgatatat    5160
taacactcta tctatgcacc ttattgttct atgataaatt tcctcttatt attataaatc    5220
atctgaatcg tgacggctta tggaatgctt caaatagtac aaaaacaaat gtgtactata    5280
agactttcta aacaattcta accttagcat tgtgaacgag acataagtgt taagaagaca    5340
taacaattat aatggaagaa gtttgtctcc atttatatat tatatattac ccacttatgt    5400
attatattag gatgttaagg agacataaca attataaaga gagaagtttg tatccattta    5460
tatattatat actacccatt tatatattat acttatccac ttatttaatg tctttataag    5520
gtttgatcca tgatatttct aatattttag ttgatatgta tatgaaaagg tactatttga    5580
actctcttac tctgtataaa ggttggatca tccttaaagt gggtctattt aattttattg    5640
cttcttacag ataaaaaaaa aattatgagt tggtttgata aaatattgaa ggatttaaaa    5700
taataataaa taacatataa tatatgtata taaatttatt ataatataac atttatctat    5760
aaaaaagtaa atattgtcat aaatctatac aatcgtttag ccttgctgga acgaatctca    5820
attatttaaa cgagagtaaa catatttgac ttttttggtta tttaacaaat tattatttaa    5880
cactatatga aatttttttt tttatcagca aagaataaaa ttaaattaag aaggacaatg    5940
gtgtcccaat ccttatacaa ccaacttcca caagaaagtc aagtcagaga caacaaaaaa    6000
acaagcaaag gaattttttt aatttgagtt gtcttgtttg ctgcataatt tatgcagtaa    6060
aacactacac ataacccttt tagcagtaga gcaatggttg accgtgtgct tagcttcttt    6120
tattttattt ttttatcagc aaagaataaa taaaataaaa tgagacactt cagggatgtt    6180
tcaacgtact ttctagacgt acgtctttcc acaatacata actattaatt aatcttaaat    6240
aaataaagga taaatatttt ttttttcttc ataaagttaa aatatgttat ttttttgttta    6300 gatgtatatt cgaataaatc taaatatatg ataatgattt tttatattga ttaaacatat    6360
aatcaatatt aaatatgata tttttttata taggttgtac acataatttt ataaggataa    6420
aaaatatgat aaaaataaat tttaaatatt tttatattta cgagaaaaaa aaatatttta    6480
gccataaata aatgaccagc atattttaca accttagtaa ttcataaatt cctatatgta    6540
tatttgaaat taaaaacaga taatcgttaa gggaaggaat cctacgtcat ctcttgccat    6600 ttgttttca tgcaaacaga aagggacgaa aaaccacctc accatgaatc actcttcaca    6660 ccattttac tagcaaacaa gtctcaacaa ctgaagccag ctctctttcc gtttcttttt    6720
acaacacttt ctttgaaata gtagtatttt ttttcacatg atttattaac gtgccaaaag    6780
atgcttattg aatagagtgc acatttgtaa tgtactacta attagaacat gaaaaagcat    6840
tgttctaaca cgataatcct gtgaaggcgt taactccaaa gatccaattt cactatataa    6900
attgtgacga aagcaaaatg aattcacata gctgagagag aaaggaaagg ttaactaaga    6960
agcaatactt cagcggccgc ttctagctag ctagggtttg ggtagtgagt gtaataaagt    7020
tgcaaagttt ttggttaggt tacgttttga ccttattatt atagttcaaa gggaaacatt    7080
aattaaaggg gattatgaag tgggctctct tgattcttgg atgaggatct tactgggtga    7140
attgagctgc ttagctatgg atcccacagt tctacccatc aataagtgct tttgtggtag    7200
tcttgtggct tccatatctg gggagcttca tttgccttta tagtattaac cttctccaag    7260
aacaaagaga gccacaccc ttctcttctt ttctctcata ataatttaaa tttgttatag    7320 actctaaaact ttaaatgttt tttttgaagt ttttccgttt ttctcttttg ccatgatccc    7380
```

```
gttcttgctg tggagtaacc ttgtccgagg tatgtgcatg attagatcca tacttaatt   7440
gtgtgcatca cgaaggtgag gttgaaatga actttgcttt tttgacctt taggaaagtt    7500
cttttgttgc agtaatcaat tttaattagt tttaattgac actattactt ttattgtcat   7560
ctttgttagt tttattgttg aattgagtgc atatttccta ggaaattctc ttacctaaca   7620
tttttatac agatctatgc tcttggctct tgcccttact cttggccttg tgttggttat    7680
ttgtctacat atttattgac tggtcgatga gacatgtcac aattcttggg cttatttgtt   7740
ggtctaataa aaggagtgct tattgaaaga tcaagacgga gattcggttt tatataaata   7800
aactaaagat gacatattag tgtgttgatg tctcttcagg ataattttg tttgaaataa    7860
tatggtaatg tcttgtctaa atttgtgtac ataattctta ctgattttt ggattgttgg    7920
attttttataa acaaatctgc ggccgcatga gccgtaaagg ttcaatacaa cgagtgcttg  7980
ttttcttagg gacaagcatt gtacttatgt atgattctgt gtaaccatga gtcttccacg   8040
ttgtactaat gtgaagggca aaataaaaac acagaacaag ttcgttttc tcaaataatg    8100
tgaaggtaga aaatggaacc atgcctcctc tcttgcatgt gatttaaaat attagcagat   8160
ggtacgtcga gtcgacctgc aggtcgactc gacgtacgtc ctcgaagaga agggttaata   8220
acacatttt taacatttt aacacaaatt ttagttattt aaaaatttat taaaaaattt     8280
aaaataagaa gaggaactct ttaaataaat ctaacttaca aaatttatga tttttaataa   8340
gttttcacca ataaaaatg tcataaaaat atgttaaaaa gtatattatc aatattctct    8400
ttatgataaa taaaaagaaa aaaaaataa aagttaagtg aaaatgagat tgaagtgact    8460
ttaggtgtgt ataaatatat caaccccgcc aacaatttat ttaatccaaa tatattgaag   8520
tatattattc catagccttt atttatttat atatttatta tataaaagct ttatttgttc   8580
taggttgttc atgaaatatt ttttggtt tatctccgtt gtaagaaaat catgtgcttt     8640
gtgtcgccac tcactattgc agcttttca tgcattggtc agattgacgg ttgattgtat    8700
ttttgttttt tatggttttg tgttatgact taagtcttca tctctttatc tcttcatcag   8760
gtttgatggt tacctaatat ggtccatggg tacatgcatg gttaaattag gtggccaact   8820
ttgttgtgaa cgatagaatt ttttttatat taagtaaact atttttatat tatgaaataa   8880
taataaaaaa aatattttat cattattaac aaaatcatat tagttaattt gttaactcta   8940
taataaaaga aatactgtaa cattcacatt acatggtaac atctttccac cctttcattt   9000
gttttttgtt tgatgacttt ttttcttgtt taaatttatt tcccttcttt taaatttgga   9060
atacattatc atcatatata aactaaaata ctaaaaacag gattacacaa atgataaata   9120
ataacacaaa tatttataaa tctagctgca atatatttaa actagctata tcgatattgt   9180
aaaataaaac tagctgcatt gatactgata aaaaaatatc atgtgctttc tggactgatg   9240
atgcagtata cttttgacat tgcctttatt ttattttca gaaaagcttt cttagttctg    9300
ggttcttcat tatttgtttc ccatctccat tgtgaattga atcatttgct tcgtgtcaca   9360
aatacaattt agntaggtac atgcattggt cagattcacg gttattatg tcatgactta    9420
agttcatggt agtacattac ctgccacgca tgcattatat tggttagatt tgataggcaa   9480
atttggttgt caacaatata aatataaata atgttttat attacgaaat aacagtgatc    9540
aaaacaaaca gttttatctt tattaacaag attttgtttt tgtttgatga cgtttttaa    9600
tgtttacgct ttcccccttc ttttgaattt agaacacttt atcatcataa aatcaaatac   9660
taaaaaaatt acatatttca taaataataa cacaaatatt tttaaaaaat ctgaaataat   9720
aatgaacaat attacatatt atcacgaaaa ttcattaata aaaatattat ataaataaaa   9780
```

```
tgtaatagta gttatatgta ggaaaaaagt actgcacgca taatatatac aaaaagatta    9840
aaatgaacta ttataaataa taacactaaa ttaatggtga atcatatcaa aataatgaaa    9900
aagtaaataa aatttgtaat taacttctat atgtattaca cacacaaata ataaataata    9960
gtaaaaaaaa ttatgataaa tatttaccat ctcataagat atttaaaata atgataaaaa   10020
tatagattat tttttatgca actagctagc caaaaagaga acacgggtat atataaaaag   10080
agtaccttta aattctactg tacttccttt attcctgacg tttttatatc aagtggacat   10140
acgtgaagat tttaattatc agtctaaata tttcattagc acttaatact tttctgtttt   10200
attcctatcc tataagtagt cccgattctc ccaacattgc ttattcacac aactaactaa   10260
gaaagtcttc catagccccc caagcggccg ctagtcgact aagtcatcaa ctattccaag   10320
ctacgtattt gggagtttgt ggagtacagc aagatgatat acctagacgg tgatatccaa   10380
gtttttgaca acattgacca cttgtttgac ttgcctgata actacttcta tgcggtgatg   10440
gactgtttct gtgagccaac ttggggccac actaaacaat atcagatcgg ttactgccag   10500
cagtgccccc ataaggttca gtggcccact cactttgggc ccaaacctcc tctctatttc   10560
aatgctggca tgtttgtgta tgagcccaat ttggctactt accgtgacct ccttcaaaca   10620
gtccaagtca cccagcccac ttcctttgct gaacaggatt ttttgaacat gtacttcaag   10680
gacaaatata ggccaattcc taatgtctac aatcttgtgc tggccatgct gtggcgtcac   10740
cctgagaacg ttgagcttga caaagttaaa gtggttcact actgtgctgc tgggtctaag   10800
ccttggaggt acactgggaa gtgactcgag gtcatcaatt actccaagct acgtatttgg   10860
gagttcgtgg agtacaagaa gacgatatac ctagacggtg acatccaagt atttggaaac   10920
atagaccact tgtttgatct gcctgataat tatttctatg cggtgatgga ttgtttctgc   10980
gagaagactt ggagccacac ccctcagttc cagattgggt actgccaaca gtgccctgat   11040
aaggttcaat ggccctctca ctttggttcc aaacctcctc tatatttcaa tgctggcatg   11100
tttgtttatg agcctaatct cgacacctac cgtgatcttc tccaaactgt ccaactcacc   11160
aagcccactt cttttgctga gcaggacttt ctcaacatgt acttcaagga caagtacaag   11220
ccaataccga acatgtacaa ccttgtgctg gccatgttgt ggcgtcaccc tgaaaatgtt   11280
gaacttgata agttcaagt ggttcattac tgtgctgctg ggtctaagcc ttggaggttc   11340
actgggaagt aactgcaggt catcaactac tccaagctcc gtatatggga gtttgtggag   11400
tacagcaaga tgatatactt ggacggagac attgaggtat atgagaacat agaccaccta   11460
tttgacctac ctgatggtaa cttttacgct gtgatggatt gttctgcga gaagacatgg   11520 agtcacaccc ctcagtacaa ggtgggttac tgccagcaat gcccggagaa ggtgcggtgg   11580
cccaccgaat gggtcagcc ccttctctt tacttcaacg ctggcatgtt cgtgttcgaa   11640
cccaacatcg ccacctatca tgacctattg aaaacggtgc aagtcaccac tcccacctcg   11700
ttcgctgaac aagatttctt gaacatgtac ttcaaggaca tttacaagcc aatccctta   11760 aattacaatc ttgtcctcgc catgctgtgg cgccacccgg aaaacgttaa attagaccaa   11820
gtcaaggttg ttcactattg cgcagcgggg tccaagccat ggagatatac ggggaagtag   11880
cctaggcgta cgcaggtaag tttctgcttc tacctttgat atatatataa taattatcat   11940
taattagtag taatataata tttcaaatat tttttcaaa ataaaagaat gtagtatata   12000
gcaattgctt ttctgtagtt tataagtgtg tatatttaa tttataactt ttctaatata   12060
tgaccaaaac atggtgatgt gcaggtccta ggctacttcc ccgtatatct ccatggcttg   12120
```

```
gaccccgctg cgcaatagtg aacaaccttg acttggtcta atttaacgtt ttccgggtgg    12180
cgccacagca tggcgaggac aagattgtaa tttaaaggga ttggcttgta aatgtccttg    12240
aagtacatgt tcaagaaatc ttgttcagcg aacgaggtgg gagtggtgac ttgcaccgtt    12300
ttcaataggt catgataggt ggcgatgttg ggttcgaaca cgaacatgcc agcgttgaag    12360
taaagagaag ggggctgacc caattcggtg ggccaccgca ccttctccgg gcattgctgg    12420
cagtaaccca ccttgtactg aggggtgtga ctccatgtct tctcgcagaa acaatccatc    12480
acagcgtaaa agttaccatc aggtaggtca aataggtggt ctatgttctc atatacctca    12540
atgtctccgt ccaagtatat catcttgctg tactccacaa actcccatat acggagcttg    12600
gagtagttga tgacctgcag ttacttccca gtgaacctcc aaggcttaga cccagcagca    12660
cagtaatgaa ccacttgaac tttatcaagt tcaacatttt cagggtgacg ccacaacatg    12720
gccagcacaa ggttgtacat gttcggtatt ggcttgtact tgtccttgaa gtacatgttg    12780
agaaagtcct gctcagcaaa agaagtgggc ttggtgagtt ggacagtttg gagaagatca    12840
cggtaggtgt cgagattagg ctcataaaca aacatgccag cattgaaata tagaggaggt    12900
ttggaaccaa agtgagaggg ccattgaacc ttatcagggc actgttggca gtacccaatc    12960
tggaactgag gggtgtggct ccaagtcttc tcgcagaaac aatccatcac cgcatagaaa    13020
taattatcag gcagatcaaa caagtggtct atgtttccaa atacttggat gtcaccgtct    13080
aggtatatcg tcttcttgta ctccacgaac tcccaaatac gtagcttgga gtaattgatg    13140
acctcgagtc acttcccagt gtacctccaa ggcttagacc cagcagcaca gtagtgaacc    13200
actttaactt tgtcaagctc aacgttctca gggtgacgcc acagcatggc cagcacaaga    13260
ttgtagacat taggaattgg cctatatttg tccttgaagt acatgttcaa aaaatcctgt    13320
tcagcaaagg aagtgggctg ggtgacttgg actgtttgaa ggaggtcacg gtaagtagcc    13380
aaattgggct catacacaaa catgccagca ttgaaataga gaggaggttt gggcccaaag    13440
tgagtgggcc actgaacctt atgggggcac tgctggcagt aaccgatctg atattgttta    13500
gtgtggcccc aagttggctc acagaaacag tccatcaccg catagaagta gttatcaggc    13560
aagtcaaaca agtggtcaat gttgtcaaaa acttggatat caccgtctag gtatatcatc    13620
ttgctgtact ccacaaactc ccaaatacgt agcttggaat agttgatgac ttagtcgact    13680
agcggccgcg acacaagtgt gagagtacta aataaatgct ttggttgtac gaatcatta    13740 cactaaataa aataatcaaa gcttatatat gccttccgct aaggccgaat gcaaagaaat    13800
tggttctttc tcgttatctt ttgccacttt tactagtacg tattaattac tacttaatca    13860
tctttgttta cggctcatta tatccggtct aggccaaggc cgcgaagtta aaagcaatgt    13920
tgtcacttgt acgtactaac acatgatgtg atagtttatg ctagctagct ataacataag    13980
ctgtctctga gtgtgttgta tattaataaa gatcatcact ggtgaatggt gatcgtgtac    14040
gtaccctact tagtaggcaa tggaagcact tagagtgtgc tttgtgcatg gccttgcctc    14100
tgttttgaga ctttttgtaat gttttcgagt ttaaatcttt gcctttgcgt acgtgggcgg    14160
atcccctgca ggagatccaa gcttggcgcg ccggcctctg cctgcgttct gctgtggaag    14220
ttcctattcc gaagttccta ttctccagaa agtataggaa cttacatgc tgcctcgtgc    14280 aagtcacgat ctcgagttct atagtgtcac ctaaatcgta tgtgtatgat acataaggtt    14340
atgtattaat tgtagccgcg ttctaacgac aatatgtcca tatggtgcac tctcagtaca    14400
atctgctctg atgccgcata gttaagccag ccccgacacc cgccaacacc cgctgacgcg    14460
ccctgacggg cttgtctgct cccggcatcc gcttacagac aagctgtgac cgtctccggg    14520
```

```
agctgcatgt gtcagaggtt ttcaccgtca tcaccgaaac gcgcgagacg aaagggcctc    14580
gtgatacgcc tattttata ggttaatgtc atgaccaaaa tccttaacg tgagttttcg     14640 ttccactgag cgtcagaccc cgtagaaaag atcaaaggat cttcttgaga tcctttttt     14700 ctgcgcgtaa tctgctgctt gcaaacaaaa aaaccaccgc taccagcggt ggtttgtttg    14760
ccggatcaag agctaccaac tcttttccg aaggtaactg gcttcagcag agcgcagata    14820
ccaaatactg tccttctagt gtagccgtag ttaggccacc acttcaagaa ctctgtagca    14880
ccgcctacat acctcgctct gctaatcctg ttaccagtgg ctgctgccag tggcgataag    14940
tcgtgtctta ccgggttgga ctcaagacga tagttaccgg ataaggcgca gcggtcgggc    15000
tgaacggggg gttcgtgcac acagcccagc ttggagcgaa cgacctacac cgaactgaga    15060
tacctacagc gtgagcattg agaaagcgcc acgcttcccg aagggagaaa ggcggacagg    15120
tatccggtaa gcggcagggt cggaacagga gagcgcacga gggagcttcc agggggaaac    15180
gcctggtatc tttatagtcc tgtcgggttt cgccacctct gacttgagcg tcgatttttg    15240
tgatgctcgt caggggggcg gagcctatgg aaaaacgcca gcaacgcggc cttttttacgg    15300 ttcctgcct tttgctggcc ttttgctcac atgttctttc ctgcgttatc ccctgattct    15360
gtggataacc gtattaccgc ctttgagtga gctgataccg ctcgccgcag ccgaacgacc    15420
gagcgcagcg agtcagtgag cgaggaagcg gaagagcgcc caatacgcaa accgcctctc    15480
cccgcgcgtt ggccgattca ttaatgcagg ttgatcagat ctcgatcccg cgaaattaat    15540
acgactcact atagggagac cacaacggtt tccctctaga ataattttg tttaacttta    15600 agaaggagat atacccatgg aaaagcctga actcaccgcg acgtctgtcg agaagtttct    15660
gatcgaaaag ttcgacagcg tctccgacct gatgcagctc tcggagggcg aagaatctcg    15720
tgctttcagc ttcgatgtag agggcgtgg atatgtcctg cgggtaaata gctgcgccga    15780
tggtttctac aaagatcgtt atgtttatcg gcactttgca tcggccgcgc tcccgattcc    15840
ggaagtgctt gacattgggg aattcagcga gagcctgacc tattgcatct cccgccgtgc    15900
acagggtgtc acgttgcaag acctgcctga aaccgaactg cccgctgttc tgcagccggt    15960
cgcggaggct atgatgcga tcgctgcggc cgatcttagc cagacgagcg ggttcggccc    16020
attcggaccg caaggaatcg gtcaatacac tacatggcgt gatttcatat gcgcgattgc    16080
tgatccccat gtgtatcact ggcaaactgt gatggacgac accgtcagtg cgtccgtcgc    16140
gcaggctctc gatgagctga tgctttgggc cgaggactgc cccgaagtcc ggcacctcgt    16200
gcacgcggat ttcggctcca caatgtcct gacgacaat ggccgcataa cagcggtcat    16260
tgactggagc gaggcgatgt tcggggattc ccaatacgag gtcgccaaca tcttcttctg    16320
gaggccgtgt tggcttgta tggagcagca gacgcgctac ttcgagcgga ggcatccgga    16380
gcttgcagga tcgccgcggc tccgggcgta tatgctccgc attggtcttg accaactcta    16440
tcagagcttg gttgacggca atttcgatga tgcagcttgg gcgcagggtc gatgcgacgc    16500
aatcgtccga tccggagccg ggactgtcgg gcgtacacaa atcgcccgca gaagcgcggc    16560
cgtctggacc gatggctgtg tagaagtact cgccgatagt ggaaaccgac gccccagcac    16620
tcgtccgagg gcaaaggaat agtgaggtac agcttggatc gatccggctg ctaacaaagc    16680
ccgaaaggaa gctgagttgg ctgctgccac cgctgagcaa taactagcat aaccccttgg    16740
ggcctctaaa cgggtcttga ggggttttt gctgaaagga ggaactatat ccggatgatc    16800
gtcgaggcct cacgtgttaa ca                                            16822
```

METHODS FOR THE IDENTIFICATION OF VARIANT RECOGNITION SITES FOR RARE-CUTTING ENGINEERED DOUBLE-STRAND-BREAK-INDUCING AGENTS AND COMPOSITIONS AND USES THEREOF

CROSS-REFERENCE TO RELATED APPLICATIONS

This application is a 371 National Stage Entry of PCT/US14/22500 which was filed 10 Mar. 2014, which claims the benefit of U.S. Patent Application Ser. No. 61/777,238, filed Mar. 12, 2013, each of which is herein incorporated by reference in their entireties.

FIELD OF THE INVENTION

This invention is in the field of molecular biology. More specifically, this invention pertains to methods for identifying and using variant recognition sites for rare-cutting engineered double strand break inducing agents.

BACKGROUND OF THE INVENTION

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and in an unpredictable copy number. Thus, efforts are undertaken to control transgene integration in plants.

Methods for inserting or modifying a DNA sequence into the genome of a variety of organism have been developed and can involve site-specific integration techniques, which rely on homologous recombination (U.S. Pat. No. 7,102,055 issued on Sep. 5, 2006) or designer endonucleases such as meganucleases, zinc finger nucleases or TALENs (US patent publication 2009-0133152 A1, published May 21, 2009).

While these systems have provided useful techniques for targeted insertion of sequences of interest, there remains a need for identifying more recognition sites for rare cutting double strand break inducing agents and for identifying recognition sites with increased activity towards rare cutting double strand beak inducing agents.

BRIEF SUMMARY OF THE INVENTION

Compositions and methods are provided which employ variant recognition sites for a rare-cutting engineered double-strand-break-inducing agent capable of introducing a rare double strand break in an intended recognition site.

Methods for identifying a variant recognition site for a rare-cutting engineered double-strand-break-inducing agent capable of introducing a rare double strand break in an intended recognition site are provided. One method comprises, a) contacting genomic DNA with a rare-cutting engineered double-strand-break-inducing agent capable of introducing a double-strand break into said genomic DNA, wherein the double-strand break results in a nucleotide overhang, b) ligating a first adapter to said nucleotide overhang, c) shearing the ligated DNA obtained in step (b) and ligating at least one second adapter to the sheared nucleotide end to allow for the amplification and sequencing of genomic DNA fragments surrounding the double strand break, d) aligning nucleotide sequences of the DNA fragments obtained in (c) with a reference genome DNA sequence; and e) identifying a variant recognition site comprising at least one nucleotide base alteration when compared to the intended recognition site of said engineered double-strand break-inducing agent. Another method comprises a method to identify a variant recognition site for a rare-cutting engineered double-strand-break-inducing agent capable of introducing a rare double strand break in an intended recognition site, said method comprising: a) contacting genomic DNA with a rare-cutting engineered double-strand-break-inducing agent capable of introducing a double-strand break into said genomic DNA, wherein the double-strand break results in a blunt end; b) creating a nucleotide overhang from the blunt end of (a); c) ligating a first adapter to the nucleotide overhang of (b); d) shearing the ligated DNA obtained in step (c) and ligating at least one second adapter to the sheared nucleotide end to allow for the amplification and sequencing of genomic DNA fragments surrounding the double strand break; e) aligning nucleotide sequences of the DNA fragments obtained in (d) with a reference genome DNA sequence; and, f) identifying a variant recognition site comprising at least one nucleotide base alteration when compared to the intended recognition site of said engineered double-strand break-inducing agent. The rare-cutting engineered double-strand-break-inducing agent can be selected from the group consisting of a meganuclease, a zinc finger nuclease, a TAL effector nuclease, a transposase, a Cas endonuclease and a site-specific recombinase. The nucleotide overhang can be a 3' or 5' nucleotide overhang.

Further provided are methods to identify a variant recognition site with an improved cleavage activity for a rare-cutting engineered double-strand-break-inducing agent capable of introducing a double strand break in an intended recognition site. The increased activity of the rare-cutting engineered double-strand-break-inducing agent is evidenced by a) a higher percent (%) cleavage of the variant recognition site when compared to the percent (%) cleavage of intended recognition site, wherein the recognition sites are located on genomic DNA; b) a higher percent (%) cleavage of the variant recognition site when compared to the percent (%) cleavage of intended recognition site, wherein the recognition sites are located on plasmid DNA; c) a higher yeast assay score for the variant recognition site when compared to the intended recognition site; or, d) any combination of (a), (b) and (c).

Further provided are methods for targeting the insertion of a polynucleotide of interest to a specific chromosomal site within a plant genome, said method comprising: a) transforming a plant cell or a plant with a DNA fragment comprising a polynucleotide of interest, wherein said genome of said plant cell or plant comprises at least one variant recognition site selected from the group consisting of SEQ ID NOs: 15, 16, 17, 18, 19, 20 and 21 or SEQ ID NOs: 23, 24, 25, 26, 27, 28, 29, 30, 31, 32, 33, 34 and 35; and, b) providing a meganuclease capable of providing a double strand break into the variable recognition site of (a); and, c) selecting said plant cell or plant comprising said polynucleotide of interest integrated into said variant recognition site.

Various compositions include a plant, a seed or a plant cell comprising in its genome a variant recognition site for a rare-cutting engineered double-strand-break-inducing agent capable of introducing a rare double strand break in an intended recognition site.

BRIEF DESCRIPTION OF THE DRAWINGS AND SEQUENCE LISTING

The invention can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821 1.825. The sequence descriptions contain the three letter codes for amino acids as defined in 37 C.F.R. §§ 1.821 1.825, which are incorporated herein by reference.

FIG. 1. (A) Genomic recognition site peak signature from a sample treated with meganuclease. Mapped sequence data originates from and comes back towards the site of cleavage. The directionality of the mapped reads is indicated in the pile-up view and by the arrows. (B) The mock control contains no enrichment or peak signature as observed for the treated sample.

FIG. 2. The 4 base overlap in the peak recognition site signature corresponds to the overhang generated by the meganuclease and defines the sequence of the genomic variant recognition site. The dashed line defines the overhangs produced by recognition site cleavage.

FIG. 3. Percent DNA base composition of oriented genomic variant recognition sites. Preferred off-nucleotides are outlined while the intended recognition bases are shaded. (A) Lig3-4 meganuclease DNA base composition of 30 genomic variant recognition sites. The LIG3-4 intended recognition site (SEQ ID NO:13) is shown at the bottom of FIG. 3A. (B) MHP14+ meganuclease DNA base composition of 254 genomic variant recognition sites. The MHP14+ intended recognition site (SEQ ID NO:14) is shown at the bottom of FIG. 3B.

FIG. 4. A) Alignment of the intended recognition site for the LIG3-4 meganuclease and LIG3-4 variant recognition sites. Preferred off-nucleotides (outlined) were introduced into the LIG3-4 intended recognition site individually (resulting in the creation of variant recognition sites −11C, −7C, −2G, −1T, +8T corresponding to SEQ ID NOs: 15-19) and in combination (resulting in the creation of variant recognition sites corresponding to SEQ ID NOs:20-22). B) Alignment of the intended recognition site for the MHP14+ meganuclease and MHP14+ variant recognition sites. Preferred off-nucleotides (outlined) were introduced into the MHP14+ intended recognition site individually (resulting in the creation of variant recognition sites −3A, −2G, −1T, +2A, +7T, +8G, +11G, +11A corresponding to SEQ ID NOs: 23-30) and in combination (resulting in the creation of variant recognition sites corresponding to SEQ ID NOs: 31-35).

FIG. 5. Comparison of plasmid DNA cleavage activity between the intended recognition site and preferred off-nucleotides individually placed into the intended recognition site for the (A) Lig3-4 meganuclease and (B) MHP14+ meganuclease. The percent cleavage activity of the intended recognition site is marked with a dashed line. As a control, at least two bases not preferred in the percent DNA base composition of genomic variant recognition sites were also assayed.

FIG. 6. Comparison of plasmid DNA cleavage activity between the intended recognition site and preferred off-nucleotides placed in combination into the intended recognition site for the (A) Lig3-4 meganuclease and (B) MHP14+ meganuclease.

Figure 7B:
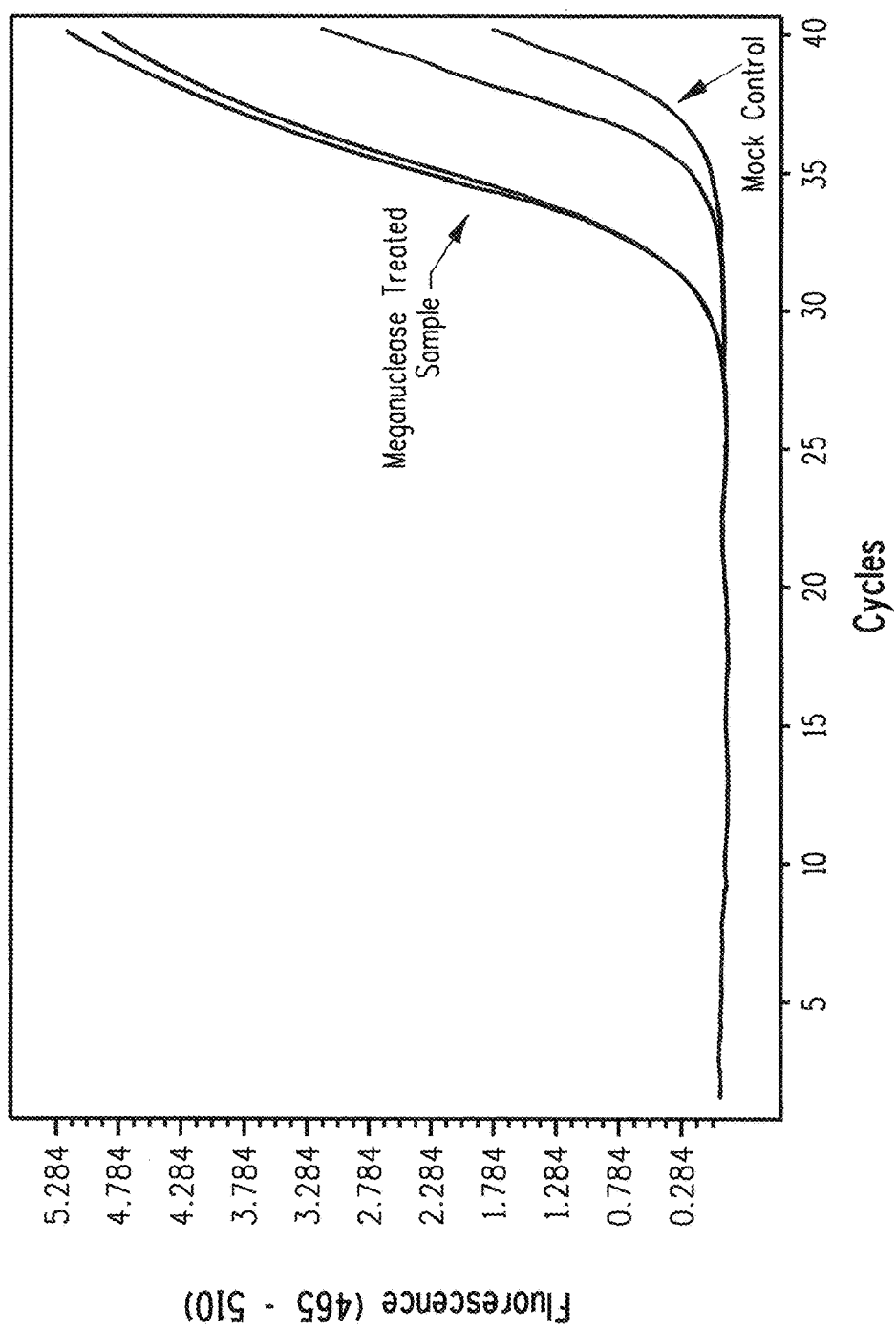

FIG. 7. Comparison of real-time PCR amplification plots from genomic variant meganuclease recognition site libraries created with either phosphorylated or non-phosphorylated biotinylated adapters containing a fully degenerate 4 nucleotide 3' overhang.

FIG. 8 shows a diagram representing the yeast screening system used to determine the meganuclease activity in yeast. Gene fragments corresponding to the first 1000 nucleotides of the yeast Ade2 coding sequence (Ade2 5' fragment) and the last 1011 nucleotides of the yeast Ade2 coding sequence (Ade2 3' fragment) were disrupted by a fragment including the yeast ura3 gene (Ura3) and meganuclease recognition sites for I-SceI.

Figure 9:
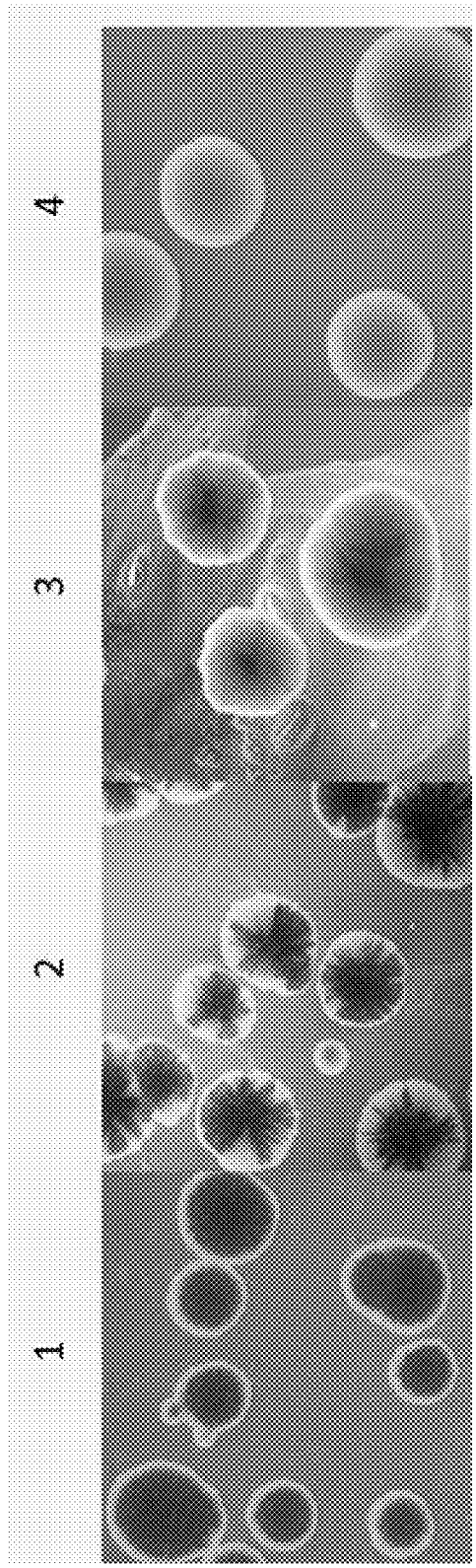

FIG. 9 shows the numerical scale and corresponding white sectoring of yeast colonies used to quantify meganuclease activity. Since the sectoring phenotype is a qualitative measure of meganuclease activity, a 0-4 numerical scoring system was implemented. A score of 0 indicates that no white sectors (no meganuclease cutting) were observed; a score of 4 indicates completely white colonies (complete cutting of the recognition site); scores of 1-3 indicate intermediate white sectoring phenotypes (and intermediate degrees of recognition site cutting)

FIG. 10. (A) Comparison of plasmid DNA cleavage activity between the MHP14+ intended recognition site (SEQ ID NO.: 14), a MHP14+ variant recognition site (SEQ ID NO: 11) that occurs naturally in the maize genome (labeled maize variant recognition site), and MHP14+ variant recognition sites (SEQ ID NOs: 31-35) that are not endogenous to the maize genome. (B) Comparison of the relative copy number of the MHP14+ variant recognition site of SEQ ID NO:11 and the MHP14+ intended recognition site (SEQ ID NO: 14) in mature maize embryos.

FIG. 11. (A) is the map of plasmid PHP57712, (B) is the map of plasmid PHP62552.

SEQUENCES

SEQ ID NO: 1 is the nucleotide sequence encoding the single chain LIG3-4 meganuclease fusion polypeptide.

SEQ ID NO: 2 is the amino acid sequence of the LIG3-4 meganuclease fusion polypeptide.

SEQ ID NO: 3 is the nucleotide sequence encoding the single chain MHP14+ meganuclease.

SEQ ID NO: 4 is the amino acid sequence of the MHP14+ meganuclease.

SEQ ID NO: 5 is the nucleotide sequence of a biotinylated, dephosphorylated adapter designed with a fully-degenerated 4 bp 3' overhang.

SEQ ID NO: 6 is the nucleotide sequence of recovery primer A.

SEQ ID NO: 7 is the nucleotide sequence of recovery primer B.

SEQ ID NO: 8 is the nucleotide sequence of an Illumina-compatibe adapter.

SEQ ID NO: 9 is the nucleotide sequence of a sequence tag.

SEQ ID NO: 10 is the nucleotide sequence of the complement sequence tag of SEQ ID NO: 9.

SEQ ID NO: 11 is the nucleotide sequence of the 5'-3' sequence shown in FIG. 2.

SEQ ID NO: 12 is the nucleotide sequence of the 3'-5' sequence shown in FIG. 2.

SEQ ID NO: 13 is the nucleotide sequence of the intended recognition site for the LIG3-4 meganuclease (also shown in FIG. 3A and FIG. 4).

SEQ ID NO: 14 is the nucleotide sequence of the intended recognition site for the MHP14+ meganuclease (also shown in FIG. 3B and FIG. 4).

SEQ ID NOs:15-22 are nucleotide sequences of variant recognition sites for the LIG3-4 meganuclease.

SEQ ID NOs:23-36 are nucleotide sequences of variant recognition sites for the MHP14+ meganuclease.

SEQ ID NO: 36 is the nucleotide sequence of the Ade2 yeast gene.

SEQ ID NO: 37 is the nucleotide sequence of the intended recognition site for the MS26 meganuclease SEQ ID NO: 38 is the nucleotide sequence of plasmid PHP57712

SEQ ID NO: 39 is the nucleotide sequence of plasmid PHP62552

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, specific examples of appropriate materials and methods are described herein.

In the context of this disclosure, a number of terms and abbreviations are used. The following definitions are provided.

As used herein, the terms "target site", "target sequence", "genomic target site" and "genomic target sequence" are used interchangeably herein and refer to a polynucleotide sequence in the genome of a plant cell or yeast cell that comprises a recognition site for a double-strand-break-inducing agent.

An "artificial target site" is a target sequence that has been introduced into the genome of an organism such as a plant or yeast. Such an artificial target sequence can be identical in sequence to an endogenous or native target sequence in the genome of the organism but can be located in a different position (i.e., a non-endogenous or non-native position) in the genome of the organism.

The terms "endogenous target sequence" and "native target sequence" are used interchangeable herein to refer to a target sequence that is endogenous or native to the genome of a host (such as a plant or yeast) and is at the endogenous or native position of that target sequence in the genome of the host (such as a plant or yeast).

The term "double-strand-break-inducing agent" as used herein refers to any nuclease which produces a double-strand break in the target sequence. Producing the double-strand break in a target sequence or other DNA can be referred to herein as "cutting" or "cleaving" the target sequence or other DNA.

The term "rare-cutting double-strand-break-inducing agent" as used herein refers to any nuclease which produces a double-strand break in a target sequence, but cuts at rare occasions (in contrast to restriction enzymes, for example) in the genome of an organism. Rare-cutting double-strand-break-inducing agents include but are not limited to endonucleases such as meganucleases, (US patent application 2332 and BB1990), zinc finger nucleases (Kim, Y. G., J. Cha, et al. (1996). "Hybrid restriction enzymes: zinc finger fusions to Fok I cleavage) Cas endonucleases (WO2007/025097 application published Mar. 1, 2007) and TALENs (Christian, M., T. Cermak, et al. 2010. Targeting DNA double-strand breaks with TAL effector nucleases. Genetics 186(2): 757-61). Cleavage by rare cutting endonucleases usually generates cohesive ends, with 3' overhangs for LAGLIDADG meganucleases (Chevalier, B. S. and B. L. Stoddard. 2001. Homing endonucleases: structural and functional insight into the catalysts of intron/intein mobility. Nucleic Acids Res 29(18): 3757-74) and 5' overhangs for Zinc Finger nucleases (Smith, J., M. Bibikova, et al. 2000, Requirements for double-strand cleavage by chimeric restriction enzymes with zinc finger DNA-recognition domains. Nucleic Acids Res 28(17): 3361-9). FokI-based TALE-nucleases (TALENs) have a similar functional layout than Zinc-Finger Nucleases, with the Zinc-finger DNA binding domain being replaced by the TALE domain (Li, T., S. Huang, et al. 2011. TAL nucleases (TALNs): hybrid proteins composed of TAL effectors and FokI DNA-cleavage domain. Nucleic Acids Res 39(1): 359-72; Christian, M., T. Cermak, et al. 2010). Cleavage with Cas endonucleases such as Cas9 endonucleases can result in blunt ends.

An "endonuclease" refers to an enzyme that cleaves the phosphodiester bond within a polynucleotide chain.

Endonucleases include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.).

An "engineered rare-cutting double-strand-break-inducing agent" refers to any rare-cutting double-strand-break-inducing agent that is engineered (modified or derived) from its native form to specifically recognize and induce a double-strand break in the desired recognition site. Thus, an engineered rare-cutting double-strand-break-inducing agent can be derived from a native, naturally-occurring nuclease or it could be artificially created or synthesized. The modification of the nuclease can be as little as one nucleotide. In some embodiments, the engineered rare-cutting double-strand-break-inducing agent induces a double-strand break in a recognition site, wherein the recognition site was not a sequence that would have been recognized by a native (non-engineered or non-modified) rare-cutting double-strand-break-inducing agent. Producing a double-strand break in a recognition site or other DNA can be referred to herein as "cutting" or "cleaving" the recognition site or other DNA.

A "meganuclease" refers to a homing endonuclease, which like restriction endonucleases, bind and cut at a specific recognition site, however the recognition sites for meganucleases are typically longer, about 18 bp or more. In some embodiments of the invention, the meganuclease has been engineered (or modified) to cut a specific endogenous recognition sequence, wherein the endogenous target sequence prior to being cut by the engineered double-strand-break-inducing agent was not a sequence that would have been recognized by a native (non-engineered or non-modified) endonuclease.

A "meganuclease polypeptide" refers to a polypeptide having meganuclease activity and thus capable of producing a double-strand break in the recognition sequence.

Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing open reading frames, introns, and inteins, respectively. For example, intron-, intein-, and free-standing gene encoded meganuclease from Saccharomyces cerevisiae are denoted I-SceI, PI-SceI, and F-SceII, respectively. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeVII, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof. In a specific embodiment, the engineered endonuclease is derived from I-Cre-I having the sequence set forth in SEQ ID NO: 15, 21 or 26 or an active variant or fragment thereof.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148; all of which are herein incorporated by reference.

As used herein, the term "Cas gene" refers to a gene that is generally coupled, associated or close to or in the vicinity of flanking CRISPR loci.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bps, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/024097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi: 10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

As used herein, the term "Cas endonuclease" refers to a Cas protein encoded by a Cas gene, wherein said Cas protein is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

As used herein, the term "guide RNA" refers to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

The term "variable targeting domain" refers to a nucleotide sequence 5-prime of the GUUUU sequence motif in the guide RNA, that is complementary to one strand of a double strand DNA target site in the genome of a plant cell, plant or seed. In one embodiment, the variable targeting domain is 12 to 30 nucleotides in length.

In one embodiment, the guide RNA and Cas endonuclease are capable of forming a complex that enables the Cas endonuclease to introduce a double strand break at a DNA target site.

As used herein, the term "recognition site" refers to a DNA sequence at which a double-strand break is induced in a cell genome by a rare-cutting double-strand-break-inducing agent. The terms "recognition site", "recognition sequence" are used interchangeably herein. The recognition site can be an endogenous site in a host (such as a yeast or plant) genome, or alternatively, the recognition site can be heterologous to the host (yeast or plant) and thereby not be naturally occurring in the genome, or the recognition site can be found in a heterologous genomic location compared to where it occurs in nature.

As used herein, the term "endogenous recognition site" refers to a rare-cutting double-strand-break-inducing agent recognition site that is endogenous or native to the genome of a host (such as a plant or yeast) and is located at the endogenous or native position of that recognition site in the genome of the host (such as a plant or yeast). The length of the recognition site can vary, and includes, for example, recognition sites that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. It is further possible that the recognition site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

As used herein, the term "intended recognition site" refers to the recognition sequence to which an engineered rare-cutting double-strand-break-inducing agent, such as an engineered meganuclease, was directed to specifically recognize and induce a double-strand break. In one embodiment, the rare-cutting double-strand-break-inducing agent is a LIG3-4 engineered meganuclease (SEQ ID NO: 2) which was designed to recognize the intended recognition sequence of SEQ ID NO: 13 (US patent publication 2009-0133152 A1, published May 21, 2009). In another embodiment, the rare-cutting double-strand-break-inducing agent is a MHP14+ engineered meganuclease (SEQ ID NO: 4) which was designed to recognize the intended recognition sequence of SEQ ID NO: 14 (in U.S. patent application Ser. No. 13/427,138 filed on Mar. 22, 2012).

As used herein, the term "variant recognition site" refers to a variant nucleotide sequence that comprises at least one base nucleotide alteration when compared to the intended recognition site to which an engineered rare-cutting double-strand-break-inducing agent such as a meganuclease, was directed to specifically recognize and induce a double-strand break. Such "alteration" include, for example: (i) replacement of at least one nucleotide, (ii) a deletion of at least one nucleotide, (iii) an insertion of at least one nucleotide, or (iv) any combination of (i)-(iii). Active variants and fragments of the recognition can comprise at least 65%, 70%, 75%, 80%, 81%, 82%, 83%, 84%, 85%, 86%, 87%, 88%. 89% 90%, 91%, 92%, 93%, 94%, 95%, 96%, 97%, 98%, 99% or more sequence identity to the given recognition sequence, wherein the active variants retain biological activity and hence are capable of being recognized and cleaved by an endonuclease. Variant recognition sites can comprise at least one (1) and up to 2, 3, 5, 6, 7, 8, 9, 10, 11, 12, 13, 14, 15, 16, 17, 18, 19 or 20 off-nucleotide preferences. In one embodiment, variant recognition sites are non-endogenous to the host genome, such variant recognition sites include, but are not limited to, the maize variant recognition sites shown in FIG. 4 (SEQ ID NOs: 15-22 and SEQ ID NOs: 23-35). In another embodiment, the variant recognition sites are present in the host genome (referred to as genomic variant recognition sites) or endogenous to the host genome, such as plant or yeast genomes. In some embodiments, the variant recognition sites can be introduced into a plant genome by the mutagenesis of an endogenous genomic sequence. Methods for the site-specific mutagenesis of genomic DNA are known in the art, and include those described, for example in U.S. Pat. Nos. 5,565,350, 5,731, 181, and 6,870,075. Other methods include the use of zinc finger nucleases, such as those methods described in U.S. Patent Publication 20050208489.

A "genomic variant recognition site" refers to a variant recognition site of a rare-cutting double-strand-break-inducing agent, such as a meganuclease, that is endogenous to the genome of an organism (such as a plant or yeast). One example of a variant recognition site that is endogenous to the maize genome is SEQ ID NO: 11.

The term "preferred off-nucleotides" or "off-nucleotide preferences" can be used interchangeably and refers to nucleotides that are located at the same position relative to the nucleotides of the intended recognition site, but are more prevalent in the identified genomic variant recognition sites (see for example the prevalence for a +8T (80%) compared with an intended recognition site +8C (13%) in FIG. 3A). In most instances, the preferred off-nucleotide when placed into the intended recognition site is cleaved at a higher percentage than the intended recognition site (see for example +8T (96% cleavage) compared to +8C (80% cleavage in FIG. 5A).

In one embodiment, the intended recognition sequence of the LIG3-4 engineered meganuclease comprises SEQ ID NO: 13, whereas the variant recognition site of the LIG3-4 engineered meganuclease comprises SEQ ID NO: 15, 16, 17, 18, 19, 20, 21, or 22. In another embodiment, the intended recognition sequence of the MHP14+ engineered meganuclease comprises SEQ ID NO: 14, whereas the variant recognition site of the MHP14+ engineered meganuclease comprises SEQ ID NO: 23, 24, 25, 26, 27, 28, 29, 30, 31, 32, 33, 34, or 35.

A "variant recognition site locus" is the position on a chromosome comprising the variable recognition site. Preferably, the variant recognition site locus is within 0, 50, 100, 200, 300, 400, 500, 600, 700, 800, 900 or 1000 base pairs of the variant recognition site.

The term "meganuclease activity" as used herein refers to the ability of a meganuclease to produce a double-strand break at a desired recognition sequence and thus retain double-strand-break-inducing activity. Producing the double-strand break in a recognition sequence or other DNA can be referred to herein as "cutting" or "cleaving" the recognition sequence or other DNA.

Assays for meganuclease activity are known and generally measure the overall activity and specificity of the meganuclease on DNA substrates containing the recognition site. These DNA substrates include but are not limited to genomic DNA and plasmid DNA. For example the meganuclease activity can be measured in-vitro as described herein in Example 3 and Example 9. In short, time-course digestions can be carried out at 37° C., 28° C., and 23° C. (or any temperature ranging between 37° C., 36° C., 35° C., 34° C., 33° C., 32° C., 31° C., 30° C., 29° C., 28° C., 27° C., 26° C., 25° C., 24° C. and 23° C.) on plasmid or genomic DNA containing a meganuclease recognition site and the % digestion of each sample (also referred to as % cleavage or to as % loss of meganuclease recognition sites) (indicative of meganuclease activity) can be determined by real-time PCR.

Meganuclease activity can also be measured using a yeast screening assay as described herein (FIGS. 8 and 9 and Example 16). In short, yeast cells with a functional Ade2 gene are white, whereas those lacking Ade2 function exhibit red pigmentation due to accumulation of a metabolite earlier in the adenine biosynthetic pathway resulting in red colonies with white sectors. The degree of white sectoring, sometimes extending to entire colonies, indicates the amount of meganuclease cutting activity. Since the sectoring phenotype is a qualitative measure of meganuclease activity, a 0-4 numerical scoring system was implemented. As shown in FIG. 3, a score of 0 indicates that no white sectors (no meganuclease cutting) were observed; a score of 4 indicates completely white colonies (complete cutting of the recognition site); scores of 1-3 indicate intermediate white sectoring phenotypes (and intermediate degrees of recognition site cutting.

Furthermore, meganuclease activity can be measured in-planta by determining the Target Site (TS) mutation rate. Target site mutation rate is defined as: (number of events with target site modification/total number events)*100%.

An "increased" or an "increased" activity are used interchangeably herein. An "increased" or "increased" meganuclease activity comprises any statistically significant increase in the activity of the parental meganuclease polypeptide as determined through any activity assays described herein.

The meganuclease can be provided via a polynucleotide encoding the endonuclease. Such a polynucleotide encoding an endonuclease can be modified to substitute codons having a higher frequency of usage in a plant, as compared to the naturally occurring polynucleotide sequence. For example the polynucleotide encoding the meganuclease can be modified to substitute codons having a higher frequency of usage in a maize or soybean plant, as compared to the naturally occurring polynucleotide sequence.

A "control meganuclease" or "reference meganuclease" can be used interchangeably and refers to any meganuclease to which a variant meganuclease is compared to. Control meganucleases can include, but are not limited to, parental or corresponding meganucleases or any wild-type 1-CreI type meganucleases.

Numbering of an amino acid or nucleotide polymer, such any one of the meganucleases of the invention, corresponds to numbering of a selected amino acid polymer or nucleic acid when the position of a given monomer component (amino acid residue, incorporated nucleotide, etc.) of the polymer corresponds to the same residue position in a selected reference polypeptide or polynucleotide.

As used herein, a "genomic region of interest" is a segment of a chromosome in the genome of a plant that is desirable for introducing a polynucleotide of interest or trait of interest. The genomic region of interest can include, for example, one or more polynucleotides of interest. Generally, a genomic region of interest of the present invention comprises a segment of chromosome that is 0-15 centi-morgan (cM).

As used herein, a "polynucleotide of interest" within a genomic region of interest is any coding and/or non-coding portion of the genomic region of interest including, but not limited to, a transgene, a native gene, a mutated gene, and a genetic marker such as, for example, a single nucleotide polymorphism (SNP) marker and a simple sequence repeat (SSR) marker.

As used herein, "physically linked," "in physical linkage", and "genetically linked" are used to refer to any two or more genes, transgenes, native genes, mutated genes, alterations, target sites, markers, and the like that are part of the same DNA molecule or chromosome.

As used herein, an "isolated" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized.

Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene is recombinant.

A "subsequence" or "fragment" is any portion of an entire sequence.

Sequence Comparisons

The following terms are used to describe the sequence relationships between two or more polynucleotides or polypeptides: (a) "reference sequence", (b) "comparison window", (c) "sequence identity", and, (d) "percent sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

(b) As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acid in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. BLASTP protein searches can be performed using default parameters. See, blast.ncbi.nlm.nih.gov/Blast.cgi.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen, Carlsbad, Calif.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for increased expression in a host cell, it is desirable to design the nucleic acid fragment such that its frequency of codon usage approaches the frequency of preferred codon usage of the host cell.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percent sequence identity" means the value determined by comparing two aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

Polynucleotide Constructs

Provided herein are polynucleotides or nucleic acid molecules comprising the variant recognition sites for rare-cutting double-strand-break-inducing agents or any active variants or fragments thereof. The terms "polynucleotide," "polynucleotide sequence," "nucleic acid sequence," and "nucleic acid fragment" are used interchangeably herein. These terms encompass nucleotide sequences and the like. The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

Further provided are recombinant polynucleotides comprising the various rare-cutting double-strand-break-inducing agents such as engineered meganucleases. The terms "recombinant polynucleotide", "recombinant nucleotide", "recombinant DNA" and "recombinant DNA construct" are used interchangeably herein. A recombinant construct comprises an artificial or heterologous combination of nucleic acid sequences, e.g., regulatory and coding sequences that are not found together in nature. For example, a transfer cassette can comprise restriction sites and a heterologous polynucleotide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The meganuclease polynucleotides disclosed herein can be provided in expression cassettes for expression in the plant of interest. The cassette can include 5' and 3' regulatory sequences operably linked to a meganuclease polynucleotide or active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the meganuclease polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), a meganuclease polynucleotide or active variant or fragment thereof, and a transcriptional and translational termination region (i.e., termination region) functional in plants. The regulatory regions (i.e., promoters, transcriptional regulatory regions, and translational termination regions) and/or the meganuclease polynucleotide or active variant or fragment thereof may be native/analogous to the host cell or to each other. Alternatively, the regulatory regions and/or the meganuclease polynucleotide of or active variant or fragment thereof may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

While it may be optimal to express the sequences using heterologous promoters, the native promoter sequences may be used. Such constructs can change expression levels of the meganuclease polynucleotide in the plant or plant cell. Thus, the phenotype of the plant or plant cell can be altered.

The termination region may be native with the transcriptional initiation region, may be native with the operably linked meganuclease polynucleotide or active variant or fragment thereof, may be native with the plant host, or may be derived from another source (i.e., foreign or heterologous) to the promoter, the meganuclease polynucleotide or active fragment or variant thereof, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various meganuclease sequence disclosed herein, including the native promoter of the polynucleotide sequence of interest. The promoters can be selected based on the desired outcome. Such promoters include, for example, constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced meganuclease expression within a particular plant tissue. Tissue-preferred promoters include those described in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Synthetic promoters can be used to express meganuclease sequences or biologically active variants and fragments thereof.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

Method of Introducing

The rare-cutting double-strand-break-inducing agent, such as a meganuclease may be introduced by any means known in the art. For example, a cell, yeast or plant having the intended or variant recognition site in its genome is provided. The meganuclease may be transiently expressed or the polypeptide itself can be directly provided to the cell. Alternatively, a nucleotide sequence capable of expressing the meganuclease may be stably integrated into the genome of the plant. In the presence of the corresponding intended or variant recognition site and the meganuclease, a donor DNA can be inserted into the transformed plant's genome. Alternatively, the different components may be brought together by sexually crossing transformed plants. Thus a sequence encoding a meganuclease and/or intended or variant recognition site can be sexually crossed to one another to allow each component of the system to be present in a single plant. The meganuclease may be under the control of a constitutive or inducible promoter. Such promoters of interest are discussed in further detail elsewhere herein.

Various methods can be used to introduce a sequence of interest such as, any of the rare-cutting double-strand-break-inducing agents into a plant or plant part. "Introducing" is intended to mean presenting to the plant, plant cell or plant part the polynucleotide or polypeptide in such a manner that the sequence gains access to the interior of a cell of the plant. The methods of the invention do not depend on a particular method for introducing a sequence into a plant or plant part, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563, 055 and 5,981,840), direct gene transfer (Paszkowski et al. (1984) *EMBO J.* 3:2717-2722), and ballistic particle acceleration (see, for example, U.S. Pat. Nos. 4,945,050; 5,879, 918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate*

Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); U.S. Pat. Nos. 5,240,855; 5,322,783; and, 5,324,646; Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via Agrobacterium tumefaciens); all of which are herein incorporated by reference.

In specific embodiments, the rare-cutting double-strand-break-inducing agent sequence, such as a meganuclease sequence, or active variant or fragments thereof can be provided to a yeast cell or plant using a variety of transient transformation methods. Such transient transformation methods include, but are not limited to, the introduction of the meganuclease protein or active variants and fragments thereof directly into a yeast cell or plant. Such methods include, for example, microinjection or particle bombardment. See, for example, Crossway et al. (1986) Mol Gen. Genet. 202:179-185; Nomura et al. (1986) Plant Sci. 44:53-58; Hepler et al. (1994) Proc. Natl. Acad. Sci. 91: 2176-2180 and Hush et al. (1994) The Journal of Cell Science 107: 775-784, all of which are herein incorporated by reference.

Generally, such methods involve incorporating a nucleotide construct of the invention within a DNA or RNA molecule. It is recognized that the an meganuclease sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) Molecular Biotechnology 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) Plant Journal 1:176-187.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence and specifically detect and/or identify a polynucleotide encoding a meganuclease polypeptide or active variant or fragment thereof as describe elsewhere herein. It is recognized that the hybridization conditions or reaction conditions can be determined by the operator to achieve this result. This length may be of any length that is of sufficient length to be useful in a detection method of choice. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide.

Methods for preparing and using probes and primers are described, for example, in Molecular Cloning: A Laboratory Manual, 2.sup.nd ed, vol. 1-3, ed. Sambrook et al., Cold Spring Harbor Laboratory Press, Cold Spring Harbor, N.Y. 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 10 (Invitrogen); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

Yeast and Plants

Yeast, plants, plant cells, plant parts and seeds, and grain having the variant recognition sequences for rare-cutting double-strand-break-inducing agents, such as meganucleases disclosed herein, are provided. In specific embodiments, the yeast, plants and/or plant parts have stably incorporated at least one heterologous variant recognition sequence disclosed herein or an active variant or fragment thereof. Thus, yeast, plants, plant cells, plant parts and seed are provided which comprise at least one variant recognition sequence of any one of SEQ ID NOs: 15, 16, 17, 18, 19, 20, 21, 22, 23, 24, 25, 26, 27, 28, 29, 30, 31, 32, 33, 34, 35 or any combination thereof, or a biologically active fragment and/or variant thereof. In specific embodiments, the variant recognition sequences expresses increased cleavage activity towards the rare-cutting double-strand-break-inducing agent.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

A transformed plant or transformed plant cell provided herein is one in which genetic alteration, such as transformation, has been affected as to a gene of interest, or is a plant or plant cell which is descended from a plant or cell so altered and which comprises the alteration. A "transgene" is a gene that has been introduced into the genome by a transformation procedure. Accordingly, a "transgenic plant" is a plant that contains a transgene, whether the transgene was introduced into that particular plant by transformation or by breeding; thus, descendants of an originally-transformed plant are encompassed by the definition. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the transgene, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the transgene; or (e) the subject plant or plant cell itself, under conditions in which the construct is not expressed.

Plant cells that have been transformed to express a meganuclease provided herein can be grown into whole plants. The regeneration, development, and cultivation of plants from single plant protoplast transformants or from various transformed explants is well known in the art. See, for example, McCormick et al. (1986) Plant Cell Reports 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a target site, stably incorporated into their genome.

The variant recognition sequences and active variant and fragments thereof disclosed herein may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicate*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Non-limiting examples of compositions and methods disclosed herein are as follows:

1) A method to identify a variant recognition site for a rare-cutting engineered double-strand-break-inducing agent capable of introducing a rare double strand break in an intended recognition site, said method comprising:
   a) contacting genomic DNA with a rare-cutting engineered double-strand-break-inducing agent capable of introducing a double-strand break into said genomic DNA, wherein the double-strand break results in a nucleotide overhang;
   b) ligating a first adapter to said nucleotide overhang;
   c) shearing the ligated DNA obtained in step (b) and ligating at least one second adapter to the sheared nucleotide end to allow for the amplification and sequencing of genomic DNA fragments surrounding the double strand break;
   d) aligning nucleotide sequences of the DNA fragments obtained in (c) with a reference genome DNA sequence; and,
   e) identifying a variant recognition site comprising at least one nucleotide base alteration when compared to the intended recognition site of said engineered double-strand break-inducing agent.
2) The method of embodiment 1 wherein the rare-cutting engineered double-strand-break-inducing agent is selected from the group consisting of a meganuclease, a zinc finger nuclease, a TAL effector nuclease, a transposase, and a site-specific recombinase.
3) The method of embodiment 1 wherein the nucleotide overhang is a 3' nucleotide overhang.
4) The method of embodiment 1 wherein the nucleotide overhang is a 5' nucleotide overhang.
5) The method of embodiment 1 wherein the first adapter ligated to the nucleotide overhang is a non-5' phosphorylated adapter.
6) The method of embodiment 1 wherein the genomic DNA is selected from the group consisting of a prokaryotic DNA, eukaryotic DNA and synthetic DNA.
7) The method of embodiment 6 wherein the eukaryotic DNA is isolated from a plant, yeast or animal.
8) The method of embodiment 7 wherein the plant is selected from the group consisting of soybean, sunflower, cotton, alfalfa, canola, cotton, tobacco, potato, *Arabidopsis*, safflower, maize, rice, sorghum, barley, wheat, millet, oats, sugarcane, turfgrass, and switch grass.
9) The method of embodiment 1, wherein the double-strand-break-inducing agent is derived from I-CreI.
10) A method to identify a variant recognition site with an improved cleavage activity for a rare-cutting engineered double-strand-break-inducing agent capable of introducing a rare double strand break in an intended recognition site, said method comprising:
    a) contacting genomic DNA with rare-cutting engineered double-strand-break-inducing agent capable of introducing a double strand break into said genomic DNA, wherein the double strand break results in a nucleotide overhang;
    b) ligating a first adapter to said nucleotide overhang;
    c) shearing the ligated DNA obtained in step (b) and ligating a second adapter to the sheared nucleotide end to allow for the amplification and sequencing of genomic DNA fragments surrounding the double strand break;
    d) aligning nucleotide sequences of the DNA fragments obtained in (c) with a reference genome DNA sequence; and,
    e) identifying a variant recognition site comprising at least one nucleotide base alteration when compared to the intended recognition site of said rare-cutting engineered double-strand-break-inducing agent;
    f) analyzing the a rare-cutting engineered double-strand-break-inducing agent activity at the variant recognition sites of d);
    g) identifying a variant recognition site that results in an increased activity of the rare-cutting engineered double-strand-break-inducing agent when compared to the activity at the intended recognition site.
11) The method of embodiment 10 wherein the increased activity of the rare-cutting engineered double-strand-break-inducing agent is evidenced by
    a) a higher percent (%) cleavage of the variant recognition site when compared to the percent (%) cleavage of intended recognition site, wherein the recognition sites are located on genomic DNA;
    b) a higher percent (%) cleavage of the variant recognition site when compared to the percent (%) cleavage of intended recognition site, wherein the recognition sites are located on plasmid DNA;
    c) a higher yeast assay score for the variant recognition site when compared to the intended recognition site; or,
    d) any combination of (a), (b) and (c)
12) A method for introducing into the genome of a cell a variant recognition site for a rare-cutting engineered double-strand-break-inducing agent capable of introducing a rare double strand break in an intended recognition site, said method comprising:
    a) providing a donor DNA comprising a variant recognition site for a rare-cutting engineered double-strand-break-inducing agent capable of introducing a double-strand break in an intended recognition site, wherein said a rare-cutting engineered double-strand-break-inducing agent is also capable of introducing a double-strand break in said variant recognition site;
    b) providing a plant cell;
    c) contacting the plant cell with the donor DNA; and,
    d) identifying at least one plant cell from (c) comprising in its genome said variant recognition site.

13) The method of embodiment 12 wherein the rare-cutting engineered double-strand-break-inducing agent is selected from the group consisting of a meganuclease, a zinc finger nuclease, a TAL effector nuclease, a transposase, a Cas endonuclease and a site-specific recombinase.

14) An isolated polynucleotide comprising a variant recognition site with an improved cleavage activity for an engineered meganuclease capable of introducing a double strand break in an intended recognition site, wherein said variant recognition site comprises a nucleotide sequence with at least 1 nucleotide base substitution when compared to the intended recognition site of SEQ ID NO: 14.

15) The isolated polynucleotide of embodiment 1, wherein said variant recognition site comprises a sequence with at least 2, 3, 4, 5, 6 or 7 base pair alterations when compared to SEQ ID NO: 14.

16) The isolated polynucleotide of embodiment 14, wherein said variant recognition site comprises:
a) an adenine (A) at a position corresponding to the nucleotide position 9 in SEQ ID NO: 14;
b) a guanine (G) at a position corresponding to the nucleotide position 10 in SEQ ID NO: 14;
c) a thymine (T) at a position corresponding to the nucleotide position 11 in SEQ ID NO: 14;
d) an adenine (A) at a position corresponding to the nucleotide position 13 in SEQ ID NO: 14;
e) a thymine (T) at a position corresponding to the nucleotide position 18 in SEQ ID NO: 14;
f) a guanine (G) at a position corresponding to the nucleotide position 19 in SEQ ID NO: 14;
g) a guanine (G) or an adenine (A) at a position corresponding to the nucleotide position 22 in SEQ ID NO: 14; or,
h) any combination of a) to g).

17) The isolated polynucleotide of embodiment 14, wherein said variant recognition sequence is selected from the group consisting of SEQ ID NOs: 23, 24, 25, 26, 27, 28, 29, 30, 31, 32, 33, 34 and 35.

18) The isolated polynucleotide of embodiment 14, wherein the improved cleavage activity is evidenced by:
a) a higher percent (%) cleavage of the variant recognition site when compared to the percent (%) cleavage of intended recognition site of SEQ ID NO:14, wherein the recognition sites are located on genomic DNA;
b) a higher percent (%) cleavage of the variant recognition site when compared to the percent (%) cleavage of intended recognition site, wherein the recognition sites are located on plasmid DNA;
c) a higher yeast assay score for the variant recognition site when compared to the intended recognition site; or,
d) any combination of (a), (b) and (c)

19) A recombinant DNA fragment comprising the isolated polynucleotide of embodiment 14.

20) A cell comprising the recombinant DNA fragment of embodiment 19.

21) The cell of embodiment 20, wherein the cell is a yeast or plant cell.

22) A transgenic plant or seed comprising the plant cell of embodiment 21.

23) The transgenic plant of embodiment 22 wherein said plant is selected from the group consisting of maize, wheat, rice, barley, sugarcane, sorghum, rye, switch grass, soybean, *Brassica*, sunflower, cotton, or alfalfa.

24) An isolated polynucleotide comprising a variant recognition site with an improved cleavage activity for an engineered meganuclease capable of introducing a double strand break in an intended recognition site, wherein said variant recognition site comprises a nucleotide sequence with at least 1 nucleotide base substitution when compared to the intended recognition site of SEQ ID NO: 13.

25) The isolated polynucleotide of embodiment 24, wherein said variant recognition site comprises a sequence with at least 2, 3, 4, or 5 base pair alterations when compared to SEQ ID NO: 13.

26) The isolated polynucleotide of embodiment 24, wherein said variant recognition site comprises:
a) a cytosine (C) at a position corresponding to the nucleotide position 1 in SEQ ID NO: 13
b) a cytosine (C)) at a position corresponding to the nucleotide position 5 in SEQ ID NO: 13;
c) a guanine (G) at a position corresponding to the nucleotide position 10 in SEQ ID NO: 13;
d) a thymine (T) an adenine (A) at a position corresponding to the nucleotide position 11 in SEQ ID NO: 13;
e) a thymine (T) at a position corresponding to the nucleotide position 19 in SEQ ID NO: 13;
f) any combination of a) to e).

27) The isolated polynucleotide of embodiment 24, wherein said variant recognition sequence is selected from the group consisting of SEQ ID NOs: 15, 16, 17, 18, 19, 20 and 21.

28) The isolated polynucleotide of embodiment 24, wherein the improved cleavage activity is evidenced by:
a) a higher percent (%) cleavage of the variant recognition site when compared to the percent (%) cleavage of intended recognition site of SEQ ID NO:13, wherein the recognition sites are located on genomic DNA;
b) a higher percent (%) cleavage of the variant recognition site when compared to the percent (%) cleavage of intended recognition site, wherein the recognition sites are located on plasmid DNA;
c) a higher yeast assay score for the variant recognition site when compared to the intended recognition site; or,
d) any combination of (a), (b) and (c).

29) A recombinant DNA fragment comprising the isolated polynucleotide of embodiment 24.

30) A cell comprising the recombinant DNA fragment of embodiment 29.

31) The cell of embodiment 30, wherein the cell is a yeast or plant cell.

32) A transgenic plant or seed comprising the plant cell of embodiment 31.

33) The transgenic plant of embodiment 32 wherein said plant is selected from the group consisting of maize, wheat, rice, barley, sugarcane, sorghum, rye, switch grass, soybean, *Brassica*, sunflower, cotton, or alfalfa.

34) A method for targeting the insertion of a polynucleotide of interest to a specific chromosomal site within a plant genome, said method comprising:
a) transforming a plant cell or a plant with a DNA fragment comprising a polynucleotide of interest, wherein said genome of said plant cell or plant comprises at least one variant recognition site selected from the group consisting of SEQ ID NOs: 15, 16, 17, 18, 19, 20 and 21; and,
b) providing a meganuclease capable of providing a double strand break into the variable recognition site of (a); and, c) selecting said plant cell or plant comprising said polynucleotide of interest integrated into said variant recognition site.
35) The method of embodiment 34 wherein providing said meganuclease comprises integrating in the genome of said plant cell or plant a nucleotide sequence encoding the meganuclease of SEQ ID NO: 1.
36) A plant or plant cell obtained by the method of embodiment 34.
37) A method for targeting the insertion of a polynucleotide of interest to a specific chromosomal site within a plant genome, said method comprising:
a) transforming a plant cell or a plant with a DNA fragment comprising a polynucleotide of interest, wherein said genome of said plant cell or plant comprises at least one variant recognition site selected from the group consisting of SEQ ID NOs: 23, 24, 25, 26, 27, 28, 29, 30, 31, 32, 33, 34 and 35;
b) providing a meganuclease capable of providing a double strand break into the variable recognition site of (a); and
c) selecting said plant cell or plant comprising said polynucleotide of interest integrated into said variant recognition site.
38) The method of embodiment 37 wherein providing the meganuclease comprises integrating in the genome of said plant cells a nucleotide sequence encoding the meganuclease of SEQ ID NO: 3
39) A plant or plant cell obtained by the method of embodiment 37.
40) A method to identify a variant recognition site for a rare-cutting engineered double-strand-break-inducing agent capable of introducing a rare double strand break in an intended recognition site, said method comprising:
a) contacting genomic DNA with a rare-cutting engineered double-strand-break-inducing agent capable of introducing a double-strand break into said genomic DNA, wherein the double-strand break results in a blunt end;
b) creating a nucleotide overhang from the blunt end of (a);
c) ligating a first adapter to the nucleotide overhang of (b);
d) shearing the ligated DNA obtained in step (c) and ligating at least one second adapter to the sheared nucleotide end to allow for the amplification and sequencing of genomic DNA fragments surrounding the double strand break;
e) aligning nucleotide sequences of the DNA fragments obtained in (d) with a reference genome DNA sequence; and,
f) identifying a variant recognition site comprising at least one nucleotide base alteration when compared to the intended recognition site of said engineered double-strand break-inducing agent.
41) The method of embodiment 40 wherein the rare-cutting engineered double-strand-break-inducing agent is a Cas endonuclease
42) The method of embodiment 41 wherein the Cas endonuclease is capable of forming a complex with a guide RNA, wherein said complex enables the Cas endonuclease to introduce a double strand break into said genomic DNA.
43) The method of embodiment 40 wherein the genomic DNA is selected from the group consisting of a prokaryotic DNA, eukaryotic DNA and synthetic DNA.
44) The method of embodiment 43 wherein the eukaryotic DNA is isolated from a plant, yeast or animal.
45) A method to identify a variant recognition site with an improved cleavage activity for a rare-cutting engineered double-strand-break-inducing agent capable of introducing a rare double strand break in an intended recognition site, said method comprising:
a) contacting genomic DNA with rare-cutting engineered double-strand-break-inducing agent capable of introducing a double strand break into said genomic DNA, wherein the double strand break results in a blunt end
b) creating a nucleotide overhang from the blunt end of (a);
c) ligating a first adapter the nucleotide overhang of (b);
d) shearing the ligated DNA obtained in step (c) and ligating a second adapter to the sheared nucleotide end to allow for the amplification and sequencing of genomic DNA fragments surrounding the double strand break;
e) aligning nucleotide sequences of the DNA fragments obtained in (d) with a reference genome DNA sequence; and,
f) identifying a variant recognition site comprising at least one nucleotide base alteration when compared to the intended recognition site of said rare-cutting engineered double-strand-break-inducing agent;
g) analyzing the rare-cutting engineered double-strand-break-inducing agent activity at the variant recognition sites of f); and,
h) identifying a variant recognition site that results in an increased activity of the rare-cutting engineered double-strand-break-inducing agent when compared to the activity at the intended recognition site.
46) The method of embodiment 45 wherein the rare-cutting engineered double-strand-break-inducing agent is a Cas endonuclease
47) The method of embodiment 46 wherein the Cas endonuclease is capable of forming a complex with a guide RNA, wherein said complex enables the Cas endonuclease to introduce a double strand break into said genomic DNA.

EXPERIMENTAL

Example 1

Creation of Rare Cutting Engineered Meganucleases

A. LIG3-4 Meganuclease and LIG3-4 Intended Recognition Sequence

An endogenous maize genomic target site comprising the LIG3-4 intended recognition sequence (SEQ ID NO: 13) was selected for design of a rare-cutting double-strand break inducing agent (SEQ ID NO: 1) as described in US patent publication 2009-0133152 A1 (published May 21, 2009). The LIG3-4 intended recognition sequence is a 22 bp polynucleotide having the following sequence: ATATACCT-CACACGTACGCGTA (SEQ ID NO: 13).

B. MHP14+ Meganucleases and MHP14 Recognition Site

An endogenous maize genomic target site comprising the MHP14+ intended recognition site (SEQ ID NO: 14) was selected for design of a rare-cutting double-strand break inducing agent (SEQ ID NO: 3) as described in U.S. patent application Ser. No. 13/427,138 filed on Mar. 22, 2012). The MHP14+ intended recognition site is a 22 bp polynucleotide located and having the following sequence: (SEQ ID NO: 14) CAAACAGATTCACGTCAGATTT.

Example 2

Meganuclease Protein Production in *E. coli*

In order to produce purified protein for in vitro genomic and plasmid based meganuclease cleavage activity assays, DNA fragments corresponding to the open-reading-frames of Lig3-4 meganuclease (SEQ ID NO: 2) and MHP14+ meganuclease (SEQ ID NO: 4) were placed into a pQE80 (Qiagen) expression vector, transformed into BL21-Gold (Agilent Technologies) *E. coli* cells, and grown overnight on solid LB media containing 100 ppm of carbenicillin. Colonies were resuspended in 2 ml of 2XYT media and 250 µl of the cell suspension was used to inoculate a 50 ml culture of 2XYT supplemented with 100 ppm of carbenicillin. Cultures were grown at 37° C. for 1 to 1.5 hrs or until the OD600 reached 0.8 and then protein expression was induced by the addition of 0.5 ml of 100 mM IPTG. Cultures were cooled to room temperature and allowed to express protein for 2 hrs. Cells were pelleted by centrifuging for 10 minutes at 5,000 rcf. The supernant was decanted, the pellet resuspended in 1 ml of Buffer 1 (50 mM Tris-HCl (pH8.0), 500 mM NaCl, 10 mM imidizole), and transferred to a 1.5 ml microfuge tube. Cells were disrupted by sonication with a two-step ⅛" microtip with 20 pulses (duty cycle 50, power 4) on a Branson 450 Analog Sonifer and centrifuged at 20,000 rcf for 15 minutes at 4° C. The supernant was diluted with 4 ml of Buffer 1 and loaded onto a disposable column containing 0.3 ml of Nickel-NTA Superflow resin (Qiagen). The column was washed with 5 ml of Buffer 2 (50 mM Tris-HCl (pH8.0), 500 mM NaCl, 60 mM imidizole) and the protein eluted with 0.6 ml of Buffer 4 (50 mM Tris-HCl (pH8.0), 500 mM NaCl, 250 mM imidizole) into a Vivaspin column (GE). To concentrate the samples, the vivaspin columns were centrifuged at 14,800 rcf for approximately 6 minutes or until the meniscus was between 75 and 50. A buffer exchange was performed using a Zeba Spin Desalting Column (Pierce) pre-equilibrated with storage buffer (25 mM Tris-HCl (pH8.0), 100 mM NaCl, 10 mM $MgCl_2$, 5 mM EDTA, 50% Glycerol). After the buffer exchange, Bovine Serum Albumin was added to a final concentration of 100 ng/µl and purified protein was stored at −20° C. until use.

Example 3

In Vitro Genomic DNA Cleavage Assays

To generate material for the capture of genomic variant recognition sites, in vitro assays were carried out with 114 nM of purified meganuclease protein isolated as described in Example 2 and 6.07 µg of purified maize genomic DNA at 32° C. for 80 minutes in a final volume of 80 µl in the presence of digestion buffer (50 mM Tris-HCl (pH 7.9), 100 mM NaCl, 10 mM $MgCl_2$, 1 mM DTT, 5 mM EDTA). After 80 minutes, the entire reaction was stopped with an equal volume of stop buffer (100 mM Tris-HCl (pH 8.0), 600 mM NaCl, 2% SDS, 100 mM EDTA, 1 mg of proteinase K per ml) and incubated at 50° C. for 30-45 minutes. Stopped reactions were purified by phenol/chloroform extraction and ethanol precipitated in the presence of 0.2 M NaCl. Precipitated genomic DNA was washed twice with 70% ethanol, dried, and resuspended in 34 µl of water.

Meganuclease protein concentration was determined visually on Nu-PAGE gels (Life Technologies) by calculating and then comparing band intensity with serially diluted samples of known concentration and genomic DNA concentration was determined using a Hoechst dye fluorometric assay.

To confirm cleavage (representing the % loss of meganuclease recognition sites) at the intended genomic recognition site, real-time PCR was performed on 1 µl of purified genomic DNA with a TaqMan assay spanning the meganuclease recognition site. The % cleavage or loss of meganuclease recognition sites was calculated via the ΔΔCt method relative to an internal control TaqMan assay using the mock control as a calibrator.

Example 4

Capture of Genomic Variant Recognition Sites & Generation of Libraries for Illumina Deep Sequencing Our method utilizes a novel adapter approach specifically tailored for the capture of cleaved I-CreI or engineered I-CreI homing endonuclease genomic variant recognition sites whose sequence is unknown and different in composition from the intended recognition site which is different from methods using restriction enzymes to perform reduced representation sequencing, restriction associated DNA (RAD-tag or RADseq) deep sequencing, whole genome sequencing (WGS), or genotype by sequencing (GBS).

Since the I-CreI homing endonuclease generates a 3' 4 nucleotide overhang at the center of its 22 bp recognition site (+2, +1, −1, −2) upon cleavage (Thompson et al. (1992) *Gene* 119:247-51 and Durrenberger et al. (1993) *Mol. Gen. Genet.* 236:409-14) and has been demonstrated to cleave its recognition site in the context of different combinations of center 4 base pairs (+2, +1, −1, −2) (Molina et al. (2012) *Nucleic Acids Res.* 40:6936-45), adapters were generated containing a 3' 4 nucleotide overhang containing all possible DNA nucleotide combinations (G, T, A, or C) of the overhang in an equimolar distribution. Thus, allowing for the efficient ligation and perfect complementation to all possible overhangs generated by recognition site cleavage in the genome subjected to I-CreI or engineered I-CreI homing endonuclease cleavage.

Similar strategies can be employed for other rare cutting double strand break inducing agents such as Zinc Finger and TALEN nucleases that cleave DNA with the non-specific catalytic domain of FokI generating overhangs of variable length and nucleotide composition within the intervening spacer region (Smith et al. (2000) *Nucleic Acids Res.* 28:3361-69 and Li et al. (2011) *Nucleic Acids Res.* 39:359-72). To capture genomic variant recognition sites, non-phosphorylated biotinylated adapters were synthesized and purified by HPLC (Integrated DNA Technologies, Inc.) containing a fully degenerate 4 nucleotide 3' nucleotide overhang complementary to the 4 nucleotide 3' overhang generated by meganuclease recognition site cleavage (SEQ ID NO: 5) and ligated to approximately 2 µg of meganuclease-cleaved genomic DNA (prepared as described in Example 3) in a 100 µl T4 ligase reaction (NEB) (representing a first adapter of the method to identify a variant recognition site for a rare-cutting engineered double-strand-break-inducing agent). Samples comprising the ligated DNA were then loaded in sonication microtubes and randomly sheared to an average peak size of 300 bps by sonication in a Covaris E220 system. The settings were 10% duty cycle, 140 peak incident power, and 200 cycles per burst. Fragments ranging from 200 to 500 bp were fractionated by electrophoresis in an agarose gel followed by gel extraction using the Qiagen Gel Extraction Kit according to manufacturer's recommendations.

Non-biotinylated ends were repaired using the End-It End repair kit (Epicentre) in a 75 µl reaction and column-purified (Qiagen). Single 3' A overhang extension was performed by incubating the repaired DNA at 37° C. for 30 minutes in a 50 µl reaction containing ATP, 1× Klenow buffer (NEBnext), and 15 units Klenow (exo-). Samples were later purified by column (Qiagen) and ligated to indexed Illumina TruSeq-compatible adapters (representing a second set of adapters of the method to identify a variant recognition site for a rare-cutting engineered double-strand-break-inducing agent) in a 50 µl reaction containing 0.3 mM indexed adapter, 1× Quick ligation buffer and 5 units T4 DNA ligase (NEB) at room temperature. After ligation, samples were incubated at 65° C. for 15 minutes and the volume adjusted to 100 µl. Streptavidin magnetic capture was performed using Dynabeads M-280 streptavidin beads (Invitrogen). A total of 100 µl resuspended Streptavidin-Dynabeads (M-280) were washed twice in TE and resuspended in 100 µl 2× B&W buffer (10 mM Tris-HCL, 1 mM EDTA, 100 µl 0.5M EDTA, 2M NaCl). Samples were incubated at 30° C. for 30 minutes, the supernatant removed, and beads washed 4 times with 1 ml of 1× B&W buffer. The final enriched sample was resuspended in 30 µl EB buffer.

Fragments were recovered from the beads by 12-cycle PCR using Phusion master mix (NEB), in a 50 µl reaction in the presence of 0.4 pmol of recovery primer A (5'GTT-GACATGCTGGATTGAGACTTC; SEQ ID NO: 6) and primer B (5'CAAGCAGAAGACGGCATACGA; SEQ ID NO: 7) according to manufacturer, except that an annealing temperature of 66° C. and extension time of 30 seconds were used. Recovered DNA was digested with SbfI (NEB) and purified twice with Agencourt AMPure XP Beads (SPRI) according to manufacturer instructions. The sample was ligated to an Illumina-compatibe adapter with a SbfI compatible overhang (SEQ ID NO: 8). The supernatant was cleaned-up twice using Agencourt AMPure XP Beads, first using a 1:1.8 and then a 1:1 sample-to-bead ratio. The final samples were resuspended in 50 µl of EB buffer. A second amplification with the standard TruSeq PCR primer cocktail (Illumina) was performed, using a 60° C. annealing temperature, followed by clean-up twice using Agencourt AMPure XP Beads in a 1:1.8 and then a 1:1 sample-to-bead ratio. The final sample was resuspended in 20 µl. Samples were evaluated on a bioanalyzer, relatively quantified using qPCR with Illumina qPCR primers, and pooled. Prior to sequencing, the pools were size selected using the lab Xchip (Caliper), according to manufacturer's instructions.

Example 5

Non-Phosphorylated Adapters Enhance Enrichment of Meganuclease Cleaved Genomic Recognition Sites To examine the effect that phosphorylation has on the ability of a first adapter (as described in Example 4) to capture and enrich for meganuclease cleaved genomic recognition sites, libraries were made with both phosphorylated and non-phosphorylated adapters. After normalizing the DNA concentration of the libraries, they were examined for enrichment of the cleaved intended recognition site by real-time PCR with a TaqMan assay immediately adjacent to the intended recognition site. As shown in FIG. 7, both libraries demonstrated enrichment relative to the mock control but the amplification plots from the library generated with the non-phosphorylated adapter reached logarithmic amplification at a much earlier amplification cycle than the library generated with the phosphorylated adapter. Using standard curves derived from maize genomic DNA, the library generated with the non-phosphorylated adapter was estimated to be approximately 900 times more enriched for the left half of the intended recognition site than the library generated with the phosphorylated adapter.

Example 6

Illumina Deep Sequencing & Post-Run Trim

After the capture and enrichment for genomic variant recognition sites and DNA preparation as described in Example 4, cluster generation and paired-end read sequencing were performed on an Illumina cBot and Genome Analyzer IIx, respectively, according to the manufacturer's instructions. Approximately 30% (v/v) phiX DNA control (Illumina) was added to the DNA library solution prior to clustering. The random base composition of the phiX DNA fragments was expected to offset any base composition bias present at the vicinity of the meganuclease site. 100 cycle paired-end recipes were used on the Illumina Genome Analyzer. Sequences and quality scores were generated by the Illumina pipeline version 2.9 software for image analysis and base calling. During base calling, the phiX control data were used to obtain error estimates and re-calibrate raw quality scores for the other samples. After initial base calling, additional filtering was performed by the Illumina software where reads are excluded if the noise estimate exceeds thresholds defined by the Illumina base calling pipeline. Base call conversion to FASTQ format (using the Illumina CASSAVA software) was followed by additional filtering where reads were trimmed and filtered according to each base's respective quality score (where bases with a quality score below 10 are trimmed from the 3' end of the read).

Example 7

In Silico Enrichment & Physical Mapping of Sequence Data to the Genomic Reference To further enrich for meganuclease cleaved and adapter-ligated genomic DNA fragments, the set of reads from a sequencing experiment was filtered using a custom script that searches for read pairs or singletons wherein at least one member of the pair (or singleton) containing a sequence tag, GCAGGACGT (SEQ ID NO: 9), at the beginning of the read or its complement ACGTCCTGC (SEQ ID NO: 10) at the end of the read. Pairs or singleton reads matching this sequence are written to a new file for use in the mapping phase, while the rest are discarded.

To reunite both halves of the cleaved genomic recognition site, the enriched read set was physically mapped to the target reference genome using bowtie version 0.12.7 (Langmead B, Trapnell C, Pop M, Salzberg S L. Ultrafast and memory-efficient alignment of short DNA sequences to the human genome. *Genome Biol* 10:R25) to identify the locations of the genome homologous to the reads. Alignment settings for specificity were adjusted on a case by case basis depending on the characteristics of the target genome and that genome's similarity to the source genotype of the data.

The resulting alignments were then used for peak detection and identification of variant recognition sequences present in the genome.

Example 8

Peak Detection and Identification of Genomic Variant Recognition Site, and Composition Using the genomic alignments generated in Example 7, peak detection was carried out using the MACs (Model-based analysis of ChiP-Seq) peak detection algorithm in Genedata Expressionist Refiner 7.5 (Genedata) with the parameters listed in Table 1.

TABLE 1

MACs (Model-based analysis of ChiP-Seq) peak detection algorithm settings in Genedata Expressionist Refiner 7.5 (Genedata).

| Experiment Setup: | ChIP Samples with Control |
|---|---|
| Method: | MACS |
| Minimum Fold Enrichment | 10 |
| Maximum Fold Enrichment | 1.00E+09 |
| Bandwidth | 200 bp |
| p-Value Threshold | 1.00E−05 |

The chromosomal regions with significant enrichment relative to the mock control were exported to excel. Regions with the greatest difference between the treated and mock control samples were prioritized and confirmed as being enriched relative to the mock control and having a peak signature resulting from genomic DNA cleavage in the Genome Browser functionality of Genedata Expressionist Refiner 7.5. As shown in FIG. 1, recognition site peak signatures contain sequence data originating and diverging from the site of cleavage with the overlapping center corresponding to the overhang generated by the double-strand break inducing reagent. Based on the overhang defined by the peak signature, the precise variant recognition site sequence present in the genomic DNA could be identified as shown in FIG. 2. To determine the correct orientation of genomic variant recognition site sequences, they were aligned to the intended target site in both sense and antisense orientations with the best fitting orientation used as the recognition site sequence. A small proportion of genomic variant recognition sites fitted equally well in both orientations. These were left in the sense orientation. The oriented genomic variant recognition sites were aligned and the percent DNA nucleotide composition was calculated for each individual position of the recognition site and compared with the intended recognition site. As shown in FIG. 3, some positions in recognition sites exhibited an off-nucleotide preference; a preference for a nucleotide other than what was targeted in the intended recognition site.

Example 9

In Vitro Plasmid DNA Cleavage Assays

In vitro meganuclease cleavage activity can also be assayed using plasmid DNA, To compare meganuclease cleavage activity at intended and variant recognition sites, annealed oligonucleotides (synthesized by Integrated DNA Technologies, Inc.) containing the intended or variant recognition site with EcoRI and HindIII overhangs were cloned into the HindIII and EcoRI restriction endonucleases sites of the pBluescript SK+ plasmid (Stratagene, now an Agilent Technologies company), and in vitro DNA cleavage activity assayed as described in Example 3 with the following modifications. Timed digestions were carried out with 0.25 nM of linearized plasmid substrate containing a single intended or variant recognition site with 25 nM of purified meganuclease protein. In vitro assays were carried out at 37° C., 28° C., and 23° C. to best examine the cleavage activity at a given variant recognition site. Stopped reactions were purified with a Qiagen PCR purification column per the manufacturer's instruction and purified DNA was diluted 200-fold prior to the quantification of cleavage activity activity or % loss of recognition sites by qPCR.

Example 10

Identifying Variant Recognition Sites and Effect of Off-Nucleotide Preferences on Meganuclease Cleavage Activity To assess the effect that the off-nucleotide preferences had on meganuclease cleavage activity, the off-nucleotide preferences were introduced into the intended recognition site individually and in combination (see FIG. 4), hereby generating variant recognition sites. Examples of such variant recognition sites are shown in Table 2 for the LIG3-4 meganuclease and Table 3 for the MHP14+ meganuclease.

TABLE 2

List of variant recognition sites for the LIG3-4 meganuclease. Nucleotides with an asterisk (*) indicate a modification compared to the nucleotide at the corresponding location of the intended recognition site (SEQ ID NO: 13).

| SEQ ID NO: | name of variable recognition site | nucleotide position of reference nucleotide (SEQ ID NO: 13) | | | | | | | | | | | | | | | | | | | | |
|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| 13 | intended LIG3-4 | A | T | A | T | A | C | C | T | C | A | C | A | C | G | T | A | C | G | C | G | T | A |
| 15 | −11C | C* | T | A | T | A | C | C | T | C | A | C | A | C | G | T | A | C | G | C | G | T | A |
| 16 | −7C | A | T | A | T | C* | C | C | T | C | A | C | A | C | G | T | A | C | G | C | G | T | A |
| 17 | −2G | A | T | A | T | A | C | C | T | C | G* | C | A | C | G | T | A | C | G | C | G | T | A |
| 18 | −1T | A | T | A | T | A | C | C | T | C | A | T* | A | C | G | T | A | C | G | C | G | T | A |
| 19 | +8T | A | T | A | T | A | C | C | T | C | A | C | A | C | G | T | A | C | G | T* | G | T | A |

TABLE 2-continued

List of variant recognition sites for the LIG3-4 meganuclease. Nucleotides with an asterisk (*) indicate a modification compared to the nucleotide at the corresponding location of the intended recognition site (SEQ ID NO: 13).

| SEQ ID NO: | name of variable recognition site | nucleotide position of reference nucleotide (SEQ ID NO: 13) | | | | | | | | | | | | | | | | | | | | |
|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| 20 | −7C, +8T | A | T | A | T | C* | C | C | T | C | A | C | A | C | G | T | A | C | G | T* | G | T | A |
| 21 | −11C, −7C, −2G, −1T, +8T | C* | T | A | T | C* | C | C | T | C | G* | T* | A | C | G | T | A | C | G | T* | G | T | A |
| 22 | −11C, −7C, −1T, +8T | C* | T | A | T | C* | C | C | T | C | A | T* | A | C | G | T | A | C | G | T* | G | T | A |

TABLE 3

List of variant recognition sites for the MHP14+ meganuclease. Nucleotides with an asterisk (*) indicate a modification cornpared to the nucleotide at the corresponding location of the intended recognition site (SEQ ID NO: 14).

| SEQ ID NO: | name of variable recognition site | nucleotide position of reference nucleotide (SEQ ID NO13 or SEQ ID NO: 14) | | | | | | | | | | | | | | | | | | | | |
|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| 14 | intended MHP14+ | C | A | A | A | C | A | G | A | T | T | C | A | C | G | T | C | A | G | A | T | T | T |
| 23 | −3A | C | A | A | A | C | A | G | A | A* | T | C | A | C | G | T | C | A | G | A | T | T | T |
| 24 | −2G | C | A | A | A | C | A | G | A | T | G* | C | A | C | G | T | C | A | G | A | T | T | T |
| 25 | −1T | C | A | A | A | C | A | G | A | T | T | T* | A | C | G | T | C | A | G | A | T | T | T |
| 26 | +2A | C | A | A | A | C | A | G | A | T | T | C | A | A* | G | T | C | A | G | A | T | T | T |
| 27 | +7T | C | A | A | A | C | A | G | A | T | T | C | A | C | G | T | C | A | T* | A | T | T | T |
| 28 | +8G | C | A | A | A | C | A | G | A | T | T | C | A | C | G | T | C | A | G | G* | T | T | T |
| 29 | +11G | C | A | A | A | C | A | G | A | T | T | C | A | C | G | T | C | A | G | A | T | T | G* |
| 30 | +11A | C | A | A | A | C | A | G | A | T | T | C | A | C | G | T | C | A | G | A | T | T | A* |
| 31 | −3A, −2G, −1T, +2A, +7T, +8G, +11G | C | A | A | A | C | A | G | A | A* | G* | T* | A | A* | G | T | C | A | T* | G* | T | T | G* |
| 32 | −3A, −2G, −1T, +2A, +7T, +8G, +11A | C | A | A | A | C | A | G | A | A* | G* | T* | A | A* | G | T | C | A | T* | G* | T | T | A* |
| 33 | −3A, −2G, −1T, +7T, +11G | C | A | A | A | C | A | G | A | A* | G* | T* | A | C | G | T | C | A | T* | G* | T | T | G* |
| 34 | −2G, −1T, +2A, +7T, +8G, +11G | C | A | A | A | C | A | G | A | T | G* | T* | A | A* | G | T | C | A | T* | G* | T | T | G* |
| 35 | −2G, −1T, +7T, +8G, +11G | C | A | A | A | C | A | G | A | T | G* | T* | A | C | G | T | C | A | T* | G* | T | T | G* |

The variant recognition sites were then cloned into the HindIII and EcoRI restriction endonucleases sites of a pBluescript SK+ vector and meganuclease activity was assayed by determining the % cleavage or % loss of recognition sites on plasmid DNA substrates as described in Example 9.

Figure 5A:
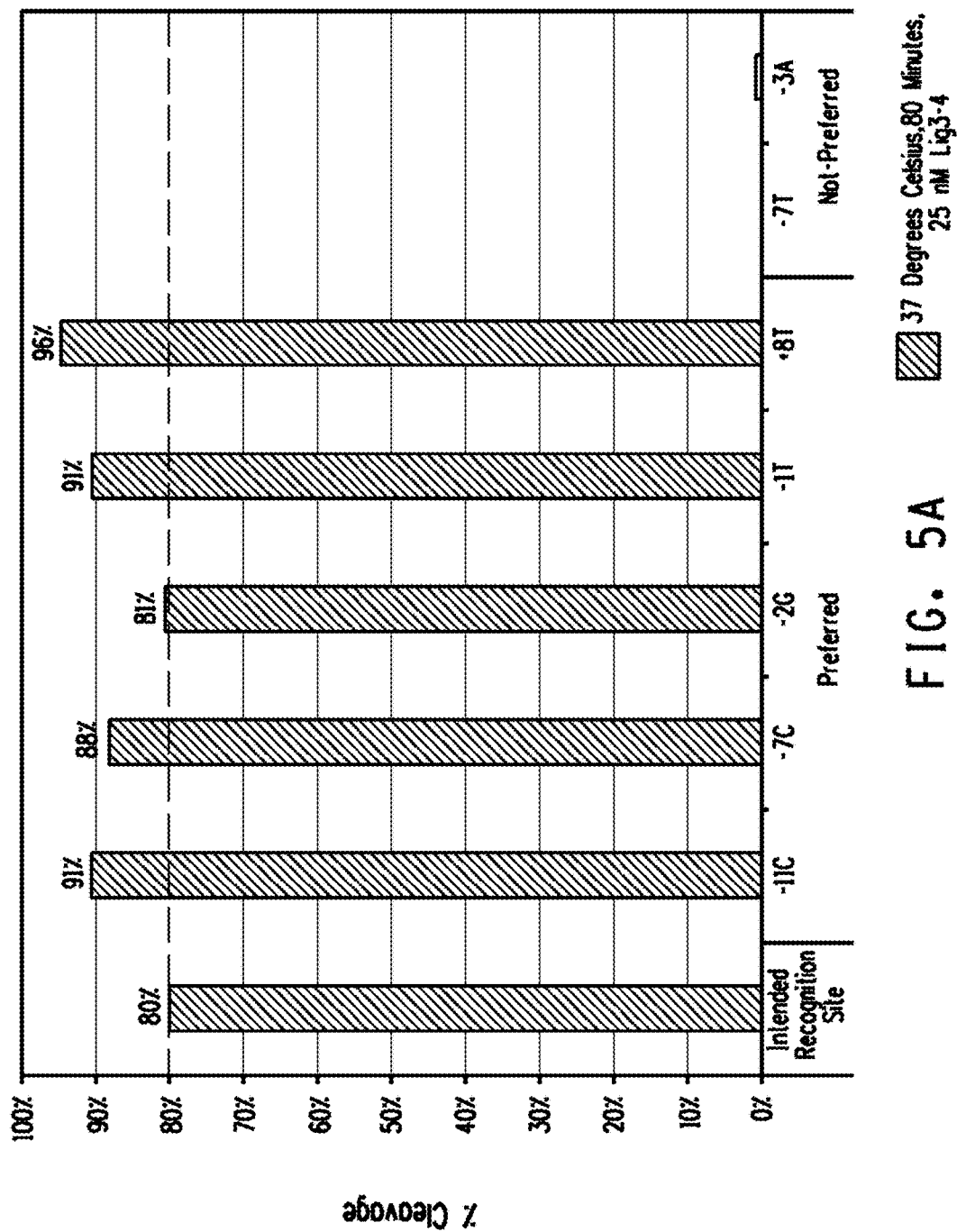

When individually introduced into their corresponding Lig3-4 and MHP14+ intended recognition sites, the off-nucleotide preferences conferred plasmid DNA cleavage activity equal to or greater than the intended recognition site (see FIGS. 5A and 5B). While nucleotides not preferred were not cleaved well (see FIGS. 5A and 5B). Interestingly, even off-nucleotide preferences within the center 4 bases (+2, +1, −1, −2) reported as not being directly contacted by the I-CreI homing endonuclease (Jurica et al. (1998) *Mol. Cell* 2:469-76; Grizot et al. (2011) *Nucleic Acids Res.* 39:6124-36, and Ulge et al. (2011) *Nucleic Acids Res.* 39:4330-9)) enhanced cleavage activity. The one exception to this was the poor cleavage activity for an adenine at position +2 for the MHP14+ meganuclease. However, when all the preferred nucleotides for MHP14+ were examined in combination as shown in FIG. 6B (recognition sites −3A, −2G, −1T, +2A, +7T, +8G, +11G and −3A, −2G, −1T, +2A, +7T, +8G, +11A), cleavage activity far greater than that of the intended recognition site was observed. Also if +2A was removed as in the −3A, −2G, −1T, +7T, +8G, +11G recognition site, there is a slight decrease in cleavage activity (see FIG. 6B) indicating that cleavage of the adenine at position +2 is context specific and dependent on the recognition or conformation of nucleotide bases adjacent to it.

Figure 6A:
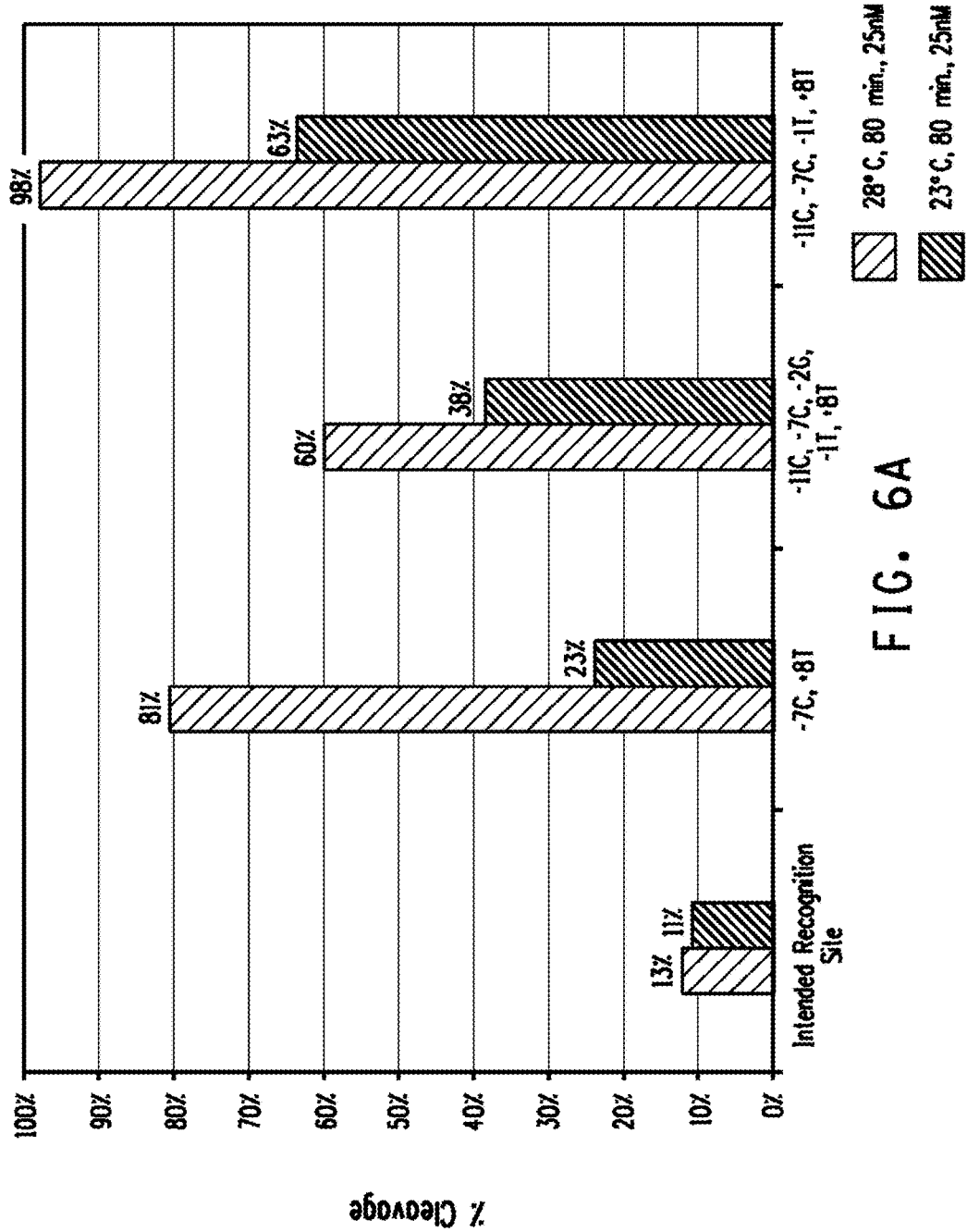
Figure 6B:
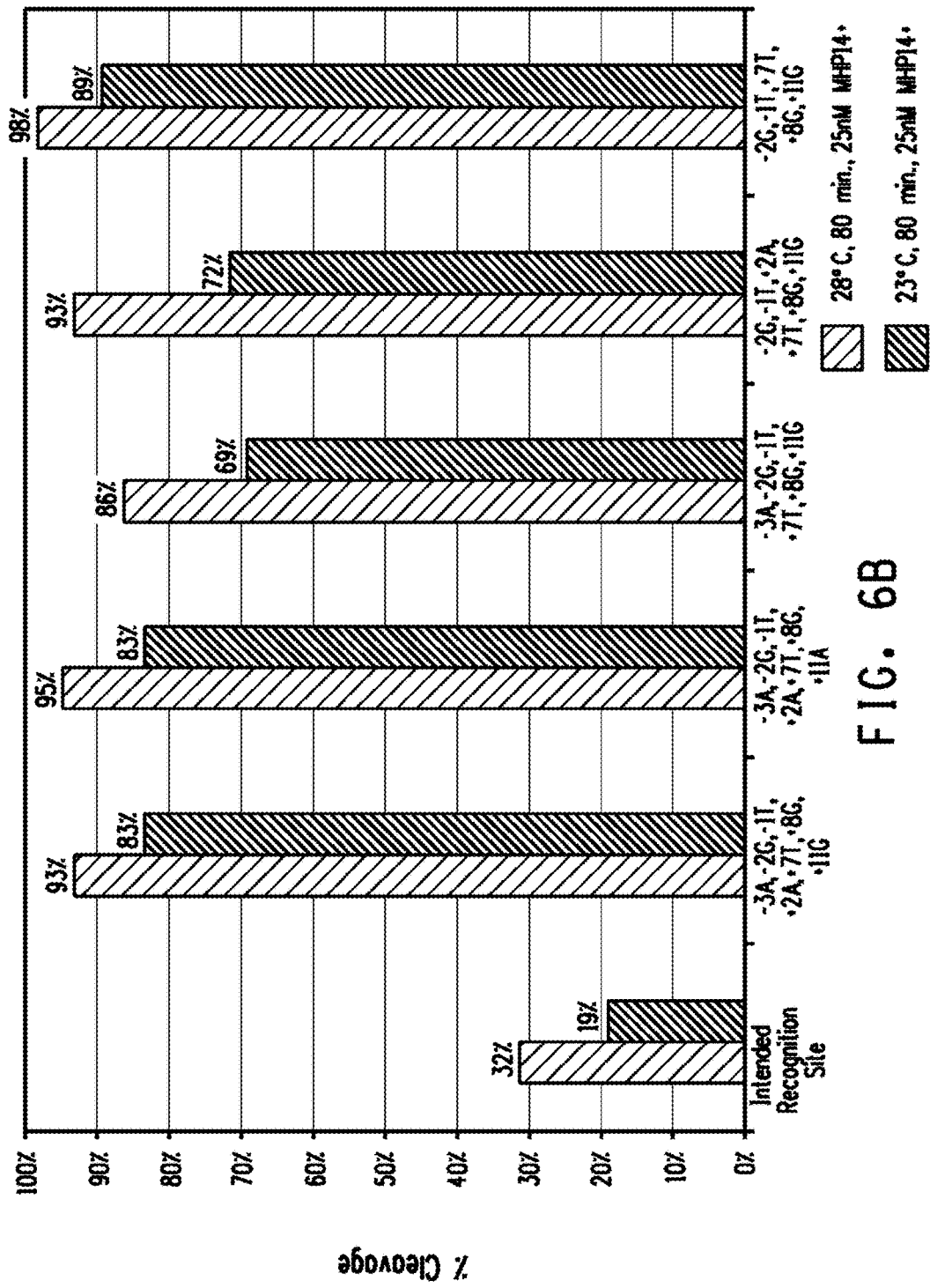

In combination, off-nucleotide preferences had an additive effect on cleavage efficiency with the best combinations being cleaved approximately 5 to 6 times more efficiently than the intended recognition site (FIG. 6). Many of the variant recognition sites could even be cleaved at temperatures as low as 23° C. where only slight cleavage activity was observed at the intended recognition site (FIGS. 6A and B). Some combinations of preferred off-nucleotides in the center 4 bases (+2,+1, −1, −2) and in positions immediately adjacent (+3, −3) influenced the magnitude of cleavage activity gained relative to the intended recognition site.

Taken together; our data indicates that the methods described herein can be used to infer the preferred DNA base contacts made by a meganuclease at individual positions across its DNA binding interface allowing a thorough evaluation of cleavage specificity providing a novel approach to examining meganuclease specificity within a genomic DNA context. Our methods also allow the identification of variant recognition sites that are cleaved more efficiently than the intended recognition site.

Example 11

Uses of Variant Recognition Sites in Plant or Animals

The variant recognition sites identified in Example 10 with improved cleavage activity over the intended recognition site (−7C, 8T (Lig3-4); −11C, −7C, −2G, −1T, +8T (Lig3-4); −11C, −7C, −1T, +8T (Lig3-4); −3A, −2G, −1T, +2A, +7T, +8G, +11G (MHP14+); −3A, −2G, −1T, +2A, +7T, +8G, +11A (MHP14+); −3A, −2G, −1T, +7T, +8G, +11G (MHP14+); −2G, −1T, +2A, +7T, +8G, +11G (MHP14+); −2G, −1T, +7T, +8G, +11G (MHP14+), corresponding to SEQ ID NOs: 13-35), or any other variant recognition site identified by the method described herein, can be transformed into any plant or animal genome and targeted for mutagenesis or gene insertion. Since the cleavage activity at these recognition sites is enhanced relative to the intended recognition site, site modification rates including deletion, insertion, or any combination of the two may also be enhanced. The variant recognition sites may also be placed individually or in combination on transgenic expression cassettes allowing for the alteration, excision, or insertion of transgenic pieces.

Example 12

Application to Other Rare-Cutting Double-Strand Break Inducing Reagents

Since oligonucleotides with both 5' and 3' degenerate ends may be synthesized in a wide range of user-specified configurations and lengths (Integrated DNA Technologies, Inc) and annealed to form double stranded DNA adapters with either 5' or 3' degenerate overhang, the methods we have established here would be applicable to any rare-cutting double-strand break reagent that creates a DNA base overhang upon cleavage. This would include but not be limited to other homing endonucleases, Zinc-Finger nucleases and TALENs.

Example 13

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560 L (Initiation medium) and placed in the dark at temperatures ranging from 26° C. to 37° C. for 8 to 24 hours prior to placing on 560Y for 4 hours at 26° C. prior to bombardment as described above.

Plasmids containing the double strand brake inducing agent and donor DNA are constructed using standard molecular biology techniques and co-bombarded with plasmids containing the developmental genes ODP2 (AP2 domain transcription factor ODP2 (Ovule development protein 2); US20090328252 A1) and Wushel (US2011/0167516).

The plasmids and DNA of interest are precipitated onto 0.6 µm (average diameter) gold pellets using a water-soluble cationic lipid Tfx™-50 (Cat #E1811, Promega, Madison, Wis., USA) as follows. DNA solution is prepared on ice using 1 µg of plasmid DNA and optionally other constructs for co-bombardment such as 50 ng (0.5 µl) of each plasmid containing the developmental genes ODP2 (AP2 domain transcription factor ODP2 (Ovule development protein 2); US20090328252 A1) and Wushel. To the pre-mixed DNA, 20 µl of prepared gold particles (15 mg/ml) and 5 µl Tfx-50 is added in water and mixed carefully. Gold particles are pelleted in a microfuge at 10,000 rpm for 1 min and supernatant is removed. The resulting pellet is carefully rinsed with 100 ml of 100% EtOH without resuspending the pellet and the EtOH rinse is carefully removed. 105 µl of 100% EtOH is added and the particles are resuspended by brief sonication. Then, 10 µl is spotted onto the center of each macrocarrier and allowed to dry about 2 minutes before bombardment.

Alternatively, the plasmids and DNA of interest are precipitated onto 1.1 µm (average diameter) tungsten pellets using a calcium chloride (CaCl$_2$) precipitation procedure by mixing 100 µl prepared tungsten particles in water, 10 µl (1 µg) DNA in Tris EDTA buffer (1 µg total DNA), 100 µl 2.5 M CaC12, and 10 µl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 µl 100% ethanol is added to the final tungsten particle pellet. For particle gun bombardment, the tungsten/DNA particles are briefly sonicated. 10 µl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560 L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 µM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 14

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI. In one example, the BBM plasmid is precipitated onto gold particles with PEI, while the transgenic expression cassette (UBI::moPAT~GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 µl of the washed gold particle/EtOH mix was centrifuged and the EtOH discarded. The particles were washed once in 100 µl ddH2O to remove residual ethanol, 250 µl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 µl aliquots of 2.5 mM HEPES buffer, pH 7.1, with 1× pulse-sonication, and then a quick vortex before each centrifugation. The particles were then suspended in a final volume of 250 µl HEPES buffer. A 25 µl aliquot of the particles was added to fresh tubes before attaching DNA. To attach uncoated DNA, the particles were pulse-sonicated, then 1 µg of DNA (in 5 µl water) was added, followed by mixing by pipetting up and down a few times with a Pipetteman and incubated for 10 minutes. The particles were spun briefly (i.e. 10 seconds), the supernatant removed, and 60 µl EtOH added. The particles with PEI-precipitated DNA-1 were washed twice in 60 µl of EtOH. The particles were centrifuged, the supernatant discarded, and the particles were resuspended in 45 µl water. To attach the second DNA (DNA-2), precipitation using TFX-50 was used. The 45 µl of particles/DNA-1 suspension was briefly sonicated, and then 5 µl of 100 ng/µl of DNA-2 and 2.5 µl of TFX-50 were added. The solution was placed on a rotary shaker for 10 minutes, centrifuged at 10,000 g for 1 minute. The supernatant was removed, and the particles resuspended in 60 µl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP:: pinII expression cassette, and DNA-2 contained a UBI:: CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI:: BBM::pinII using PEI, then coated with UBI::moPAT~YFP using TFX-50, and then bombarded into scutellar cells on the surface of immature embryos. PEI-mediated precipitation results in a high frequency of transiently expressing cells on the surface of the immature embryo and extremely low frequencies of recovery of stable transformants (relative to the TFX-50 method). Thus, it is expected that the PEI-precipitated BBM cassette expresses transiently and stimulates a burst of embryogenic growth on the bombarded surface of the tissue (i.e. the scutellar surface), but this plasmid will not integrate. The PAT~GFP plasmid released from the Ca++/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT~GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI::moPAT~G-FPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII. It is expected that the cells receiving the RNA will immediately begin dividing more rapidly and a large portion of these will have integrated the agronomic gene. These events can further be validated as being transgenic clonal colonies because they will also express the PAT~GFP fusion protein (and thus will display green fluorescence under appropriate illumination). Plants regenerated from these embryos can then be screened for the presence of the polynucleotide of interest.

Example 15

Production and Model System Transformation of Somatic Soybean Embryo Cultures with Soybean Expression Vectors and Plant Regeneration Culture Conditions:
Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 mL of fresh liquid SB196 (the preferred subculture interval is every 7 days).

Soybean embryogenic suspension cultures are transformed with the soybean expression plasmids by the method of particle gun bombardment (Klein et al., *Nature* 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants are picked 45-55 days after planting. Seeds are removed from the pods and placed into a sterilized magenta box. The soybean seeds are sterilized by shaking them for 15 min in a 5% Clorox solution with 1 drop of Ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. When cultures are being prepared for production transformation, cotyledons are transferred to plates containing SB1 medium (25-30 cotyledons per plate). Plates are wrapped with fiber tape and are maintained at 26° C. with cool white fluorescent lights on 16:8 h day/night photoperiod at light intensity of 60-80 µE/m2/s for eight weeks, with a media change after 4 weeks. When cultures are being prepared for model system expemiments, cotyledons are transferred to plates containing SB199 medium (25-30 cotyledons per plate) for 2 weeks, and then transferred to SB1 for 2-4 weeks. Light and temperature conditions are the same as described above. After incubation on SB1 medium, secondary embryos are cut and placed into SB196 liquid media for 7 days.

Preparation of DNA for Bombardment:

Either an intact plasmid or a DNA plasmid fragment containing the genes of interest and the selectable marker gene are used for bombardment. Fragments from soybean expression plasmids are obtained by gel isolation of digested plasmids. In each case, 100 µg of plasmid DNA is used in 0.5 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 h. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 µL aliquot of sterile distilled water containing 3 mg of gold particles (3 mg gold) is added to 30 µL of a 10 ng/µL DNA solution (either intact plasmid or DNA fragment prepared as described herein), 25 µL 5M $CaCl_2$ and 20 µL of 0.1 M spermidine. The mixture is shaken 3 min on level 3 of a vortex shaker and spun for 10 sec in a bench microfuge. The supernatant is removed, followed by a wash with 400 µL 100% ethanol and another brief centrifugation. The 400 µL ethanol is removed and the pellet is resuspended in 40 µL of 100% ethanol. Five µL of DNA suspension is dispensed to each flying disk of the Biolistic PDS1000/HE instrument disk. Each 5 µL aliquot contains approximately 0.375 mg gold per bombardment (e.g., per disk).

For model system transformations, the protocol is identical except for a few minor changes (i.e., 1 mg of gold particles is added to 5 µL of a 1 µg/µL DNA solution, 50 µL of a 2.5M $CaCl_2$ is used and the pellet is ultimately resuspended in 85 µL of 100% ethanol thus providing 0.058 mg of gold particles per bombardment).

Tissue Preparation and Bombardment with DNA:

Approximately 150-200 mg of seven day old embryogenic suspension cultures is placed in an empty, sterile 60×15 mm petri dish and the dish is covered with plastic mesh. The chamber is evacuated to a vacuum of 27-28 inches of mercury, and tissue is bombarded one or two shots per plate with membrane rupture pressure set at 1100 PSI. Tissue is placed approximately 3.5 inches from the retaining/stopping screen. Model system transformation conditions are identical except 100-150 mg of embryogenic tissue is used, rupture pressure is set at 650 PSI and tissue is place approximately 2.5 inches from the retaining screen.

Selection of Transformed Embryos:

Transformed embryos are selected either using hygromycin (when the hygromycin B phosphotransferase (HPT) gene is used as the selectable marker) or chlorsulfuron (when the acetolactate synthase (ALS) gene is used as the selectable marker).

Following bombardment, the tissue is placed into fresh SB196 media and cultured as described above. Six to eight days post-bombardment, the SB196 is exchanged with fresh SB196 containing either 30 mg/L hygromycin or 100 ng/mL chlorsulfuron, depending on the selectable marker used. The selection media is refreshed weekly. Four to six weeks post-selection, green, transformed tissue is observed growing from untransformed, necrotic embryogenic clusters.

Embryo Maturation:

For production transformations, isolated, green tissue is removed and inoculated into multiwell plates to generate new, clonally propagated, transformed embryogenic suspension cultures. Transformed embryogenic clusters are cultured for four-six weeks in multiwell plates at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 µE/$m^2$s. After this time embryo clusters are removed to a solid agar media, SB166, for one-two weeks and then subcultured to SB103 medium for 3-4 weeks to mature embryos. After maturation on plates in SB103, individual embryos are removed from the clusters, dried and screened for alterations in their fatty acid compositions as described in Example 7.

For model system transformations, embryos are matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters are removed to 35 mL of SB228 (SHaM liquid media) in a 250 mL Erlenmeyer flask. Tissue is maintained in SHaM liquid media on a rotary shaker at 130 rpm and 26° C. with cool white fluorescent lights on a 16:8 hr day/night photoperiod at a light intensity of 60-85 µE/m2/s for 2 weeks as embryos mature. Embryos grown for 2 weeks in SHaM liquid media are equivalent in size and fatty acid content to embryos cultured on SB166/SB103 for 5-8 weeks.

Media Recipes:

| SB 196 - FN Lite Liquid Proliferation Medium (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g glucose
2 mL 2,4-D (20 mg/L final concentration)
pH 5.7
8 g TC agar SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g activated charcoal
pH 5.7
2 g gelrite SB 103 Solid Medium (Per Liter)

1 package MS salts (Gibco/BRL—Cat. No. 11117-066)
1 mL B5 vitamins 1000× stock
60 g maltose
750 mg MgCl2 hexahydrate
pH 5.7
2 g gelrite SB 71-4 Solid Medium (Per Liter)

1 bottle Gamborg's B5 salts w/sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (Per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

SB 228—Soybean Histodifferentiation & Maturation (SHaM) (Per Liter)

| DDI $H_2O$ | 600 mL |
|---|---|
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≤30° C.): | |
| *Glutamine (final concentration 30 mM) 4% | 110 mL |

*Note: Final volume will be 1010 mL after glutamine addition.

Since glutamine degrades relatively rapidly, it may be preferable to add immediately prior to using media. Expiration 2 weeks after glutamine is added; base media can be kept longer w/o glutamine.

FN-Lite Macro for SHAM 10×—Stock #1 (Per Liter)

| $(NH_4)2SO_4$ (ammonium sulfate) | 4.63 g |
|---|---|
| $KNO_3$ (potassium nitrate) | 28.3 g |

-continued

| MgSO$_4$*7H$_2$0 (magnesium sulfate heptahydrate) | 3.7 g |
|---|---|
| KH$_2$PO$_4$ (potassium phosphate, monobasic) | 1.85 g |
| Bring to volume | |
| Autoclave | |

MS Micro 1000×—Stock #2 (Per 1 Liter)

| H$_3$BO$_3$ (boric acid) | 6.2 g |
|---|---|
| MnSO$_4$*H$_2$O (manganese sulfate monohydrate) | 16.9 g |
| ZnSO4*7H20 (zinc sulfate heptahydrate) | 8.6 g |
| Na$_2$MoO$_4$*2H20 (sodium molybdate dihydrate) | 0.25 g |
| CuSO$_4$*5H$_2$0 (copper sulfate pentahydrate) | 0.025 g |
| CoCl$_2$*6H$_2$0 (cobalt chloride hexahydrate) | 0.025 g |
| KI (potassium iodide) | 0.8300 g |
| Bring to volume | |
| Autoclave | |

FeEDTA 100×—Stock #3 (Per Liter)

| Na$_2$EDTA* (sodium EDTA) | 3.73 g |
|---|---|
| FeSO$_4$*7H$_2$0 (iron sulfate heptahydrate) | 2.78 g |

*EDTA must be completely dissolved before adding iron.
Bring to Volume
Solution is photosensitive. Bottle(s) should be wrapped in foil to omit light.
Autoclave Ca 100×—Stock #4 (Per Liter)

| CaCl$_2$*2H$_2$0 (calcium chloride dihydrate) | 44 g |
|---|---|
| Bring to Volume | |
| Autoclave | |

B5 Vitamin 1000×—Stock #5 (Per Liter)

| Thiamine*HCl | 10 g |
|---|---|
| Nicotinic Acid | 1 g |
| Pyridoxine*HCl | 1 g |
| Myo-Inositol | 100 g |
| Bring to Volume | |
| Store frozen | |

4% Glutamine—Stock #6 (Per Liter)

| DDI water heated to 30° C. | 900 mL |
|---|---|
| L-Glutamine | 40 g |
| Gradually add while stirring and applying low heat. | |
| Do not exceed 35° C. | |
| Bring to Volume | |
| Filter Sterilize | |
| Store frozen* | |

*Note: Warm thawed stock in 31° C. bath to fully dissolve crystals.

Regeneration of Soybean Somatic Embryos into Plants:

In order to obtain whole plants from embryogenic suspension cultures, the tissue must be regenerated. Embryos are matured as described in above. After subculturing on medium SB103 for 3 weeks, individual embryos can be removed from the clusters and screened for alterations in their fatty acid compositions as described in Example 7. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for fatty acids.

Example 16

Yeast Screening System for Meganuclease Activity

Yeast screening strains were generated as hosts for the screening of meganuclease activity. The yeast Ade2 gene (Genetika 1987 Jul. 23(7):1141-8) (SEQ ID NO: 36) was used as a visible marker as well as a selection in the scheme depicted in FIG. 7. Gene fragments corresponding to the first 1000 nucleotides of the Ade2 coding sequence (Ade2 5' fragment) and the last 1011 nucleotides of the Ade2 coding sequence (Ade2 3' fragment) were disrupted by a There are 305 nucleotides of sequence duplication between the Ade2 5' fragment and the Ade2 3' fragment. The resulting constructs were used to replace the Ade2 gene (chromosome 15 nucleotide position 566193-564480) of yeast strain BY4247. The resulting yeast screening strains VER8145, VER8189 and HD1327 can be characterized as BY4742 MATa his3delta1 leu2delta0 lys2delta0 ura3delta0 Ga12+). If meganuclease cutting occurs between the duplicated sequences, homologous recombination can occur, resulting in a functional Ade2 gene.

The generation of a functional Ade2 gene can be used as a selection: when yeast cells are grown on media lacking adenine, only those with a functional Ade2 gene are able to grow.

The generation of a functional Ade2 gene can also be used as a screen. Yeast cells with a functional Ade2 gene are white, whereas those lacking Ade2 function exhibit red pigmentation due to accumulation of a metabolite earlier in the adenine biosynthetic pathway resulting in red colonies with white sectors as shown in FIGS. 8 and 9. The degree of white sectoring, sometimes extending to entire colonies, indicates the amount of meganuclease cutting activity. Since the sectoring phenotype is a qualitative measure of meganuclease activity, a 0-4 numerical scoring system was implemented. As shown in FIG. 9, a score of 0 indicates that no white sectors (no meganuclease cutting) were observed; a score of 4 indicates completely white colonies (complete cutting of the recognition site); scores of 1-3 indicate intermediate white sectoring phenotypes (and intermediate degrees of recognition site cutting).

Example 17

Analysis of Variant Recognition Sequences for LIG3-4 and MHP14+ Meganuclease in Maize To demonstrate the cleavage activity of the variant recognition sites identified herein in planta, a naturally occurring variant recognition site (SEQ ID NO.: 11) for the MHP14+ meganuclease was identified in maize and its in planta cleavage activity (as measure by the frequency of mutagenesis of the recognition site) and in vitro cleavage activity was compared with the cleavage activity of the MHP14+ intended recognition site.

To determine the cleavage activity of the recognition sites in planta, plasmid DNA containing the MHP14+ meganuclease expression cassette was delivered to maize embryos via particle bombardment to allow for double strand break to occur, followed by realtime PCR that was carried out with TaqMan assays spanning the recognition sites. The relative copy number was calculated via the ΔΔCt method relative to an internal control TaqMan assay using untransformed embryos as a calibrator. Embryos with a relative copy number less than 0.8 were considered to be cleaved and/or mutagenized. Meganuclease in vitro cleavage activity was assayed as described in Example 9 on plasmid DNA.

Figure 10A:
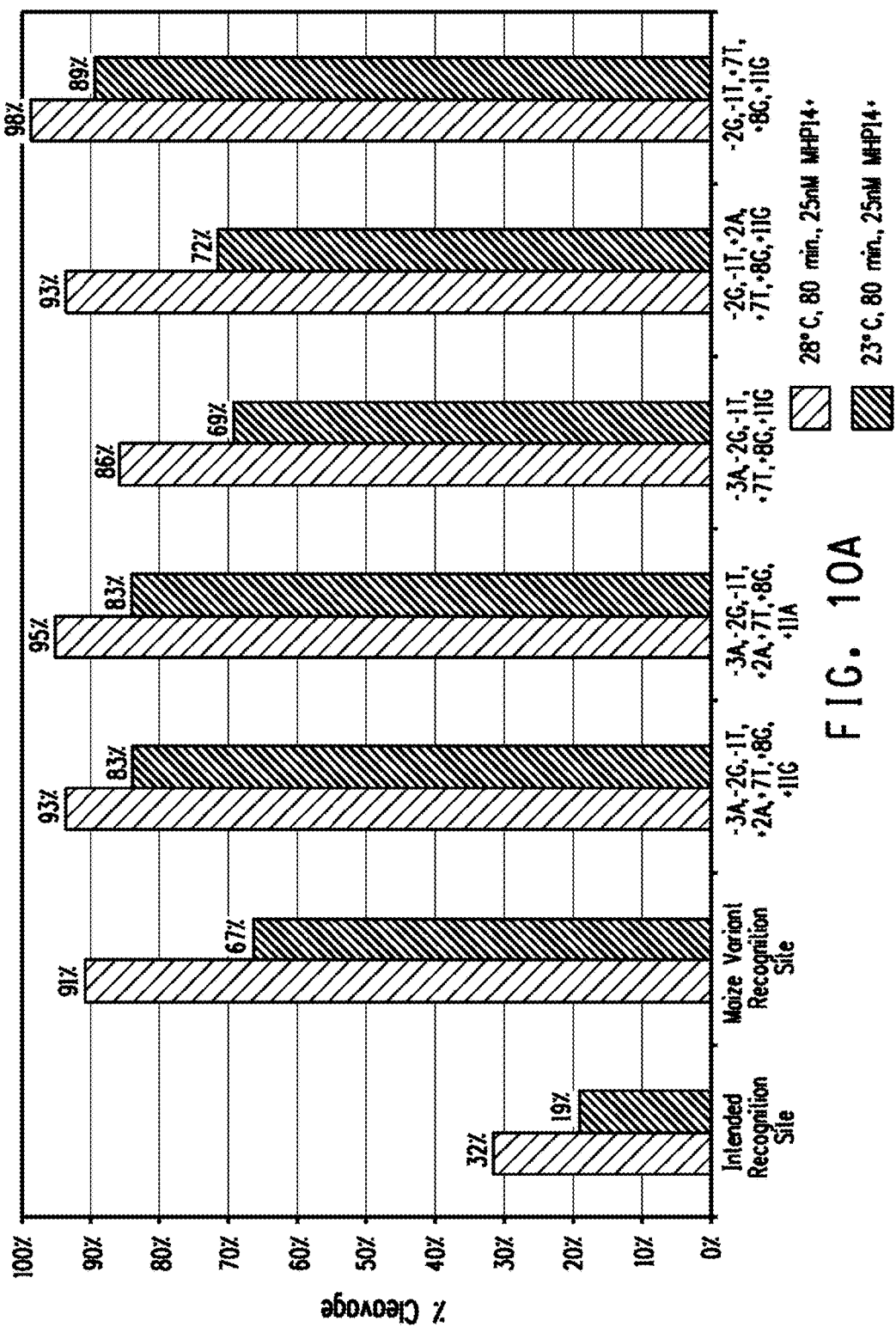
Figure 10B:
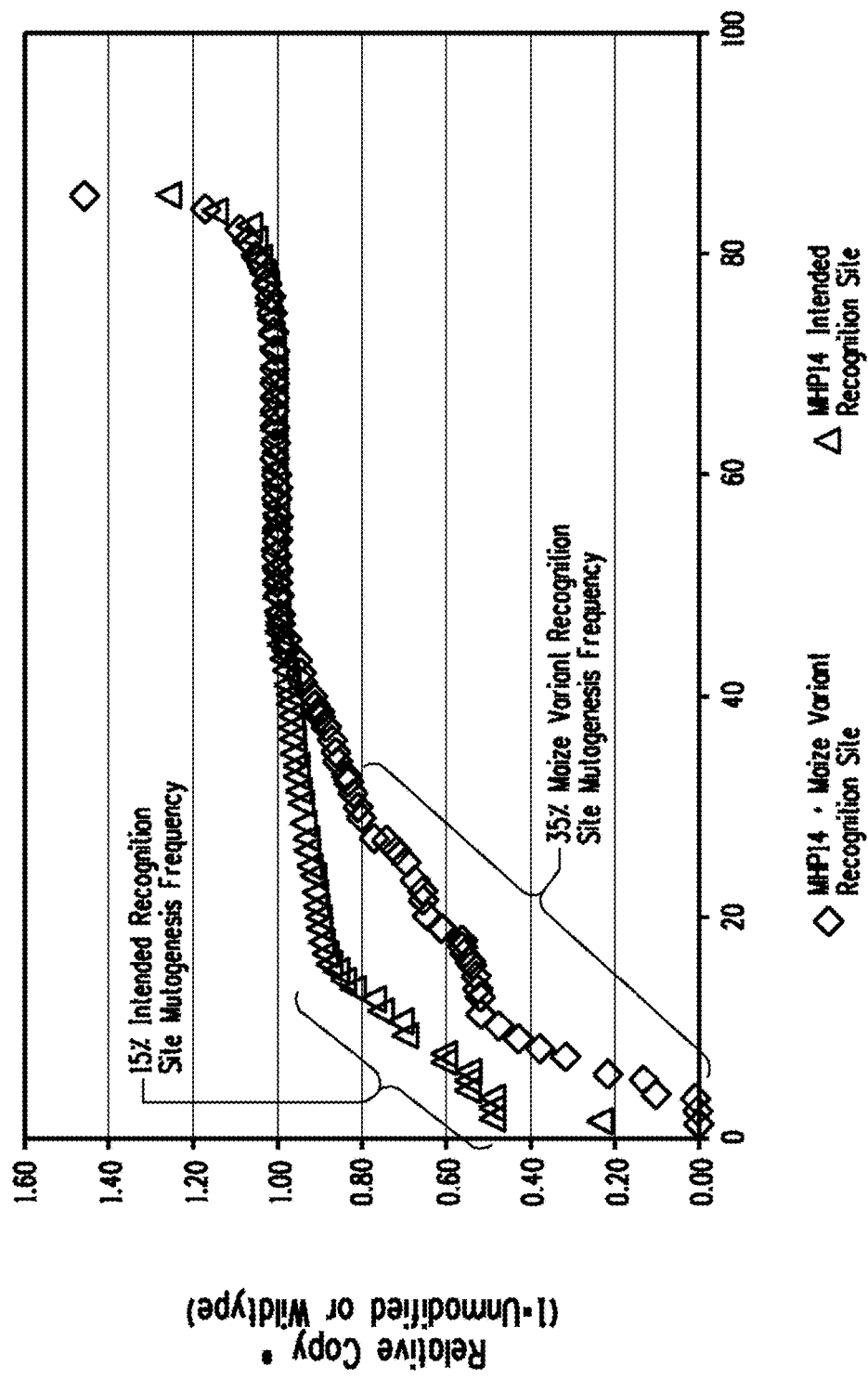

The plasmid DNA in vitro cleavage activity at the variant recognition site of SEQ ID NO:11 was approximately 3 times as efficient as the intended recognition site of SEQ ID NO: 14, depending on the reaction temperature (see FIG. 10A). A similar trend was observed in planta with 35% of the mature embryos demonstrating cleavage at the endogenous variant recognition site, as evidenced by the mutagenesis, while only 15% exhibited cleavage (mutagenesis) at the intended recognition site (see FIG. 10B).

Similar analysis can be performed for the LIG3-4 variant recognitions sites described herein or for any other variant recognition sites identified. It is expected that site modification rates including deletion, insertion, or any combination of the two would be enhanced for the other variant recognition sites with improved cleavage activity identified in Example 10 (−7C, 8T (Lig3-4); −11C, −7C, −2G, −1T, +8T (Lig3-4); −11C, −7C, −1T, +8T (Lig3-4); −3A, −2G, −1T, +2A, +7T, +8G, +11G (MHP14+); −3A, −2G, −1T, +2A, +7T, +8G, +11A (MHP14+); −3A, −2G, −1T, +7T, +8G, +11G (MHP14+); −2G, −1T, +2A, +7T, +8G, +11G (MHP14+); −2G, −1T, +7T, +8G, +11G (MHP14+), corresponding to SEQ ID NOs: 13-35) or any other variant recognition site identified by the method described herein were to be artificially introduced into the genome.

Example 18

Analysis of Variant Recognition Sequences for LIG3-4 and MHP14+ Meganuclease in Soybean To test the intended and variant recognition sites for LIG3-4 and MHP14+ meganucleases in a dicotyledonous plant like soybean, the maize recognition sites sequences can be cloned into transformation DNA constructs and introduced in soybean by biolistic transformation as described in Example 15.

Comparing Multiple Recognition Sites Located at Same Locus

In order to compare the cleavage activity (cutting efficiencies) of different recognition sequences, one can arrange several recognition sequences together in one DNA construct and insert different constructs containing the multiple recognitions sites preferably at the same genomic locus to eliminate position effects. The FLP/FRT mediated site-specific integration transformation system is a valuable tool to achieve the above purpose by placing different donor DNA constructs at previously characterized targets sites (Plant Physiology, Li et al., 2009; U.S. application Ser. No. 12/634,775). Once the recognitions sites are integrated in the soybean genome, single copy transgenic events can be identified, characterized and selected as new materials for subsequent transformation with corresponding meganucleases to evaluate the cleavage activity (cutting efficiency) of each recognition sites by its corresponding meganuclease. Since several recognition sites are inserted at the same genomic site, the cutting efficiency of the corresponding meganucleases can be compared.

Figure 11A:
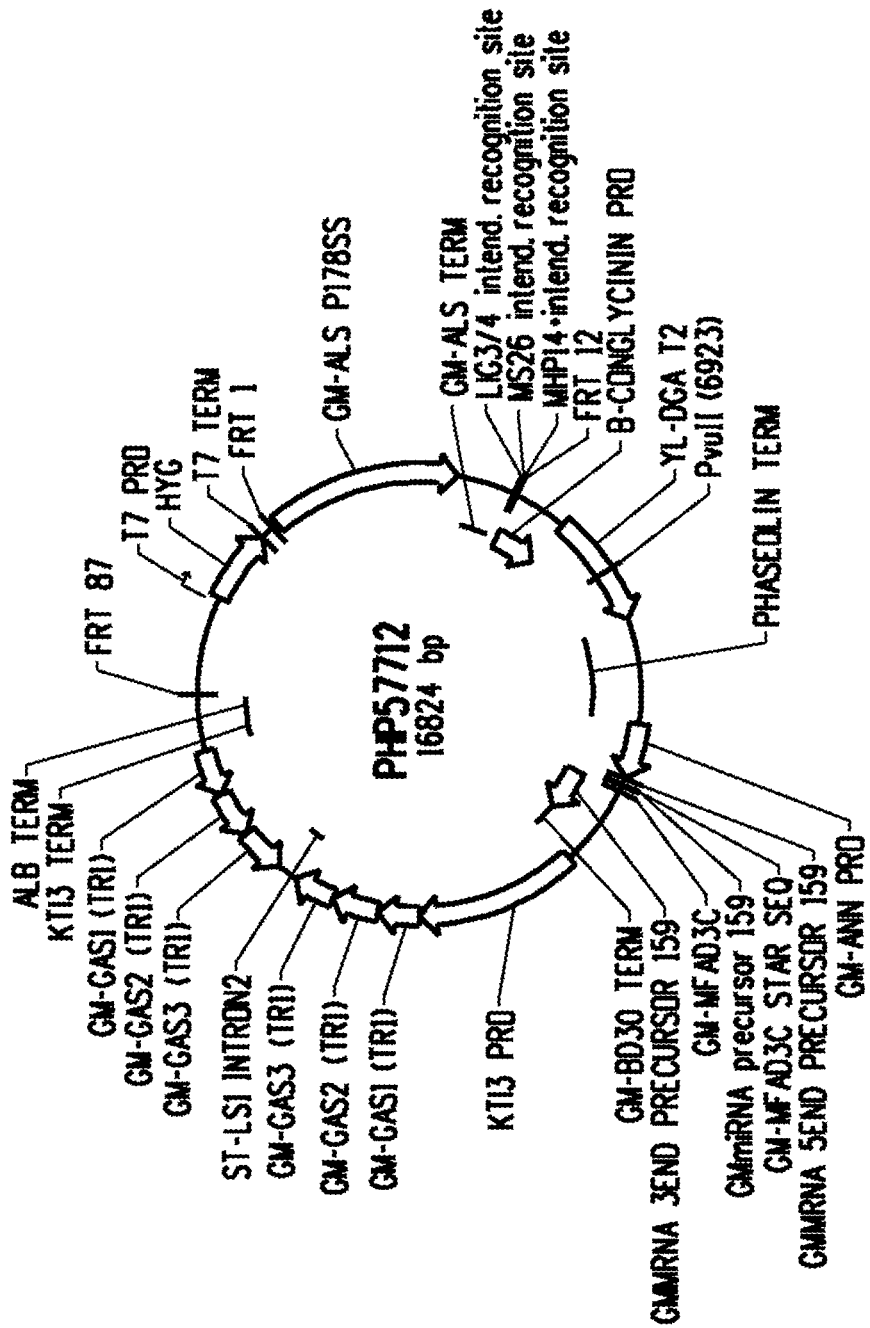
Figure 11B:
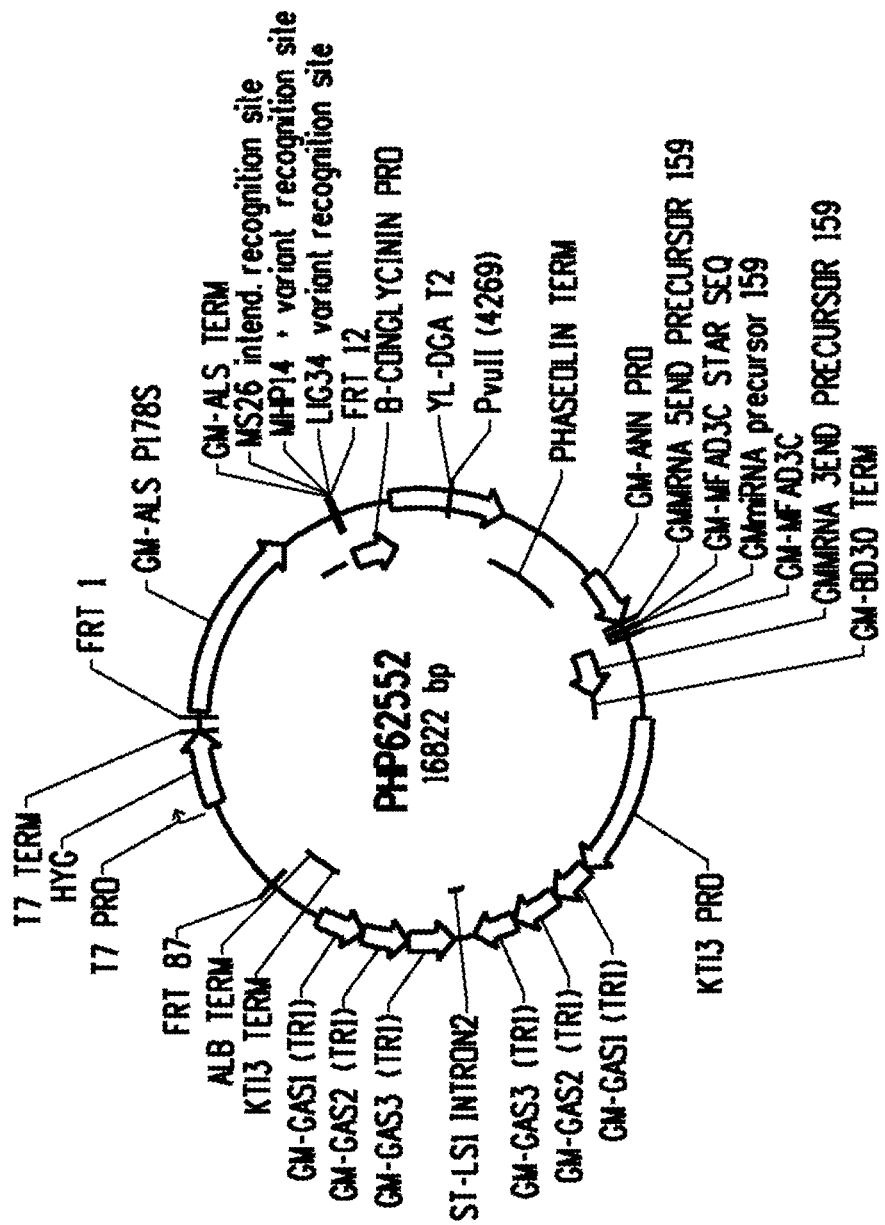

Towards this end, the intended recognition site for LIG34 (SEQ ID NO:13) as well as the intended recognition sites for MHP14+ (SEQ ID NO:14) and MS26 (SEQ ID NO: 37) were cloned into a 551 donor construct PHP57712 (SEQ ID NO: 38) between the selectable marker gene GM-ALS and trait gene cassettes DGAT2 (diacylglycerol acyltransferase) over-expression for high oil, FAD3 (ω-3 desaturase) artificial microRNA co-supression for high unsaturated fatty acids, and GAS (galactinol synthase) hairpin co-suppression for high available energy (FIG. 11A). Transgenic events with the PHP57712 donor DNA integrated at several previously characterized genomic sites were obtained by biolistic particle soybean SSI transformation as described above. Transgenic events with clean insertions of the trait genes and meganuclease recognition sequences were selected and will be used for next round transformation with LIG34, MS26, and MHP14+ meganucleases to test the cleavage activity of the three intended recognition sites.

Comparing Intended Versus Variant Recognition Sites Located at Same Locus

A variant recognition site for LIG3-4 (SEQ ID NO:22) and a variant recognition site for MHP14+ (SEQ ID NO:35) as well as the intended recognition site for MS26 (SEQ ID NO: 37) were cloned into another SSI donor construct, PHP62252 (SEQ ID NO: 39) (FIG. 11B) and are being transformed to some of the same soybean genomic sites by SSI transformation. Transgenic events with clean insertions of the trait genes and meganuclease recognition sequences will be selected and used for another round transformation with MS26, MHP14+, and LIG34 meganucleases to test the cleavage activities of the recognition sites. Since all the recognition sites are inserted at the same genomic sites, the cutting efficiencies of the various recognition sites can be more meaningfully compared. The cleavage activity of the variant recognition sites of LIG3-4 and MHP14+ (SEQ ID NOs: 22 and 35) can be compared to the cleavage activity of their intended recognition sites (SEQ ID NO: 13 and 14) as described in Example 17.

Example 19

A Method for Targeting the Insertion of a Polynucleotide of Interest to a Specific Chromosomal Site within a Plant Genome A nucleotide sequence comprising a variable recognition sequence for a double strand break inducing agent is introduced into the target organism's genome establishing a target site (comprising the variable recognition sequence) for insertion of a nucleotide sequences of interest. A library of stable plants or cultured tissues can then be established comprising a variable recognition site at different locations throughout the plant genome.

One example of such variant recognition sites are SEQ ID NOs: 15, 16, 17, 18, 19, 20 and 21 which can be cleaved by the LIG3-4 meganuclease encoded by SEQ ID NO: 1. Another example of variant recognition sites are SEQ ID NOs: 23, 24, 25, 26, 27, 28, 29, 30, 31, 32, 33, 34 and 35 which can be cleaved by the MHP14+ meganuclease encoded by SEQ ID NO: 3. In one embodiment, the SEQ ID NOs: 15, 16, 17, 18, 19, 20 and 21 and are SEQ ID NOs: 23, 24, 25, 26, 27, 28, 29, 30, 31, 32, 33, 34 and 35 are not endogenous to the maize or plant genome.

Once a stable plant or cultured tissue is established, a DNA fragment comprising a polynucleotide of interest is introduced into the stably transformed plant or tissues in the presence of a double strand break inducing protein such as a meganuclease protein. This process results in the insertion of the polynucleotide of interest into the variable recognition sequence.

It is recognized that the transformed plant may comprise multiple target sites, for example, but not limited to, multiple recognition sites capable of being cleaved by a double strand break inducing agent, as well as recombination sites such as FRT sites or LOX sites. Examples of recombination sites are known in the art and include FRT sites (See, for example, Schlake and Bode (1994) *Biochemistry* 33:12746-12751; Huang et al. (1991) *Nucleic Acids Research* 19:443-448).

Example 20

Capture of Cas Endonuclease Genomic Variant Recognition Sites & Generation of Libraries for Illumina Deep Sequencing To capture genomic DNA variant recognition sites for rare cutting DNA double-strand-break inducing agents where most of the cleaved products result in blunt-ended termini such as for the Cas endonucleases (Gasiunas et al. (2012) Proc. Natl. Acad. Sci. USA 109:E2579-86, Jinek et al. (2012) Science 337:816-21), the addition of an adenine to the 3' termini of cleaved genomic DNA variant recognition site(s) may be utilized. Adapters containing a complementary 3' thymine overhang may then be used to selectively ligate to and enrich for the blunt-ended termini resulting from cleavage by the Cas endonuclease.

To generate material for the capture of genomic variant recognition sites, in vitro digestion assays would be carried-out and purified essentially as described in Example 3 except purified Cas endonuclease protein and the nucleic acid component(s) need to form a functional Cas endonuclease complex capable of cleaving a DNA target site would be used instead of a meganuclease protein. In vitro reactions may be carried-out in a different buffer, at different temperatures and or length(s) of incubation to foster ideal Cas endonuclease cleavage conditions.

A single 3' adenine overhang will then be added to the Cas endonuclease cleaved blunt-ended termini by incubating the in vitro digested genomic DNA at 37° C. for 30 minutes in a 50 µl reaction containing ATP, 1× Klenow buffer (NEBnext), and 15 units Klenow (exo-) and purified. Non-phosphorylated or phosphoryalted biotinylated adapters synthesized and purified by HPLC containing a 3' thymine nucleotide overhang complementary to the adenine 3' nucleotide overhang may then be ligated to approximately 2 µg of the Cas endonuclease digested 3' adenine extended genomic DNA in a 100 µl T4 ligase reaction (NEB). The resulting adapter ligated Cas endonuclease intended and variant recognition sites may then be enriched for, sequenced and identified similar to that described in Examples 4, 6, 7 and 8.

What is claimed:

1. An in vitro method to identify a Cas endonuclease double strand break site in genomic DNA, said method comprising:
   a. contacting the genomic DNA with a Cas endonuclease-guide RNA complex, wherein the Cas endonuclease-guide RNA complex introduces a double-strand break in the genomic DNA, resulting in a blunt end;
   b. creating a nucleotide overhang from the blunt end of (a);
   c. ligating a first adapter to the nucleotide overhang of (b), resulting in a ligated DNA;
   d. obtaining fragments of the ligated DNA of (c) and ligating a second adapter to the DNA fragments to allow for the amplification and sequencing of the DNA fragments that each comprise the first adapter on one end and the second adapter on the other end;
   e. amplifying and sequencing the DNA fragments of (d);
   f. aligning nucleotide sequences of the DNA fragments of (e) with a reference DNA sequence; and,
   g. identifying the double-strand break site.

2. The method of claim 1 wherein the nucleotide overhang is a 3' nucleotide overhang.

3. The method of claim 1 wherein the nucleotide overhang is a 5' nucleotide overhang.

4. The method of claim 1 wherein the genomic DNA is selected from the group consisting of a prokaryotic DNA, eukaryotic DNA, and synthetic DNA.

5. The method of claim 4 wherein the eukaryotic DNA is isolated from a plant, yeast or animal.

6. The method of claim 5 wherein the plant is selected from the group consisting of soybean, sunflower, cotton, alfalfa, canola, tobacco, potato, *Arabidopsis*, safflower, maize, rice, sorghum, barley, wheat, millet, oats, sugarcane, turfgrass, and switch grass.

* * * * *